(12) United States Patent
Edwards et al.

(10) Patent No.: US 10,143,792 B2
(45) Date of Patent: Dec. 4, 2018

(54) MEDICAMENT DELIVERY DEVICE FOR ADMINISTRATION OF OPIOID ANTAGONISTS INCLUDING FORMULATIONS FOR NALOXONE

(71) Applicant: kaleo, Inc., Richmond, VA (US)

(72) Inventors: Eric S. Edwards, Moseley, VA (US); Evan T. Edwards, Charlottesville, VA (US); Mark J. Licata, Doswell, VA (US); Frank E. Blondino, Henrico, VA (US)

(73) Assignee: kaleo, Inc., Richmond, VA (US)

(*) Notice: Subject to any disclaimer, the term of this patent is extended or adjusted under 35 U.S.C. 154(b) by 85 days.

(21) Appl. No.: 15/331,073

(22) Filed: Oct. 21, 2016

(65) Prior Publication Data

US 2017/0035957 A1 Feb. 9, 2017

Related U.S. Application Data

(63) Continuation of application No. 14/694,725, filed on Apr. 23, 2015, now Pat. No. 9,474,869, which is a
(Continued)

(51) Int. Cl.
*A61M 5/00* (2006.01)
*A61M 5/20* (2006.01)
(Continued)

(52) U.S. Cl.
CPC ............ *A61M 5/002* (2013.01); *A61K 31/485* (2013.01); *A61M 5/2033* (2013.01);
(Continued)

(58) Field of Classification Search
CPC ... A61K 31/485; A61M 11/00; A61M 11/007; A61M 15/0001; A61M 15/08;
(Continued)

(56) References Cited

U.S. PATENT DOCUMENTS

| 2,960,087 A | 11/1960 | Uytenbogaart |
| 3,055,362 A | 9/1962 | Uytenbogaart |

(Continued)

FOREIGN PATENT DOCUMENTS

| CN | 101057830 | 10/2007 |
| EP | 0429039 B1 | 3/1995 |

(Continued)

OTHER PUBLICATIONS

"Solutions for Medical Devices," 3M Brochure, © 3M, (2006), 80-6201-3490-0, 8 pages.
(Continued)

*Primary Examiner* — Imani Hayman

(57) ABSTRACT

Medicament delivery devices for administration of opioid antagonists are described herein. In some embodiments, an apparatus includes a housing, a medicament container disposed within the housing and an energy storage member disposed within the housing. The medicament container is filled with a naloxone composition that includes naloxone or salts thereof, a tonicity-adjusting agent, and a pH adjusting agent, whereby the osmolality of the naloxone composition ranges from about 250-350 mOsm and the pH ranges from about 3-5. The energy storage member is configured to produce a force to deliver the naloxone composition.

26 Claims, 47 Drawing Sheets

Related U.S. Application Data continuation of application No. 14/153,575, filed on Jan. 13, 2014, now Pat. No. 9,022,022, which is a continuation of application No. 13/036,720, filed on Feb. 28, 2011, now Pat. No. 8,627,816.

(51) Int. Cl.

| | | |
|---|---|---|
| *A61M 5/32* | (2006.01) | |
| *A61M 11/00* | (2006.01) | |
| *A61M 15/08* | (2006.01) | |
| *A61M 15/00* | (2006.01) | |
| *A61K 31/485* | (2006.01) | |
| *A61M 5/50* | (2006.01) | |
| *A61M 5/24* | (2006.01) | |
| *G09B 5/04* | (2006.01) | |
| *G09B 19/24* | (2006.01) | |

(52) U.S. Cl.
CPC ........ *A61M 5/2046* (2013.01); *A61M 5/2459* (2013.01); *A61M 5/3232* (2013.01); *A61M 5/5086* (2013.01); *A61M 11/00* (2013.01); *A61M 11/007* (2014.02); *A61M 15/0001* (2014.02); *A61M 15/08* (2013.01); *G09B 5/04* (2013.01); *G09B 19/24* (2013.01); *A61M 2202/048* (2013.01); *A61M 2205/14* (2013.01); *A61M 2205/3584* (2013.01); *A61M 2205/581* (2013.01); *A61M 2205/583* (2013.01); *A61M 2205/80* (2013.01); *A61M 2205/8206* (2013.01); *A61M 2209/06* (2013.01); *A61M 2210/0618* (2013.01)

(58) Field of Classification Search
CPC ........ A61M 2202/048; A61M 2205/14; A61M 2205/3584; A61M 2205/581; A61M 2205/583; A61M 2205/80; A61M 2205/8206; A61M 2209/06; A61M 2210/0618; A61M 5/002; A61M 5/2033; A61M 5/2046; A61M 5/2459; A61M 5/3232; A61M 5/5086; G09B 19/24; G09B 5/04

See application file for complete search history.

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,031,889 A | 6/1977 | Pike |
| 4,108,177 A | 8/1978 | Pistor |
| 4,186,741 A | 2/1980 | Cesaro |
| 4,226,235 A | 10/1980 | Sarnoff et al. |
| 4,227,528 A | 10/1980 | Wardlaw |
| 4,258,713 A | 3/1981 | Wardlaw |
| 4,284,077 A | 8/1981 | Wagner |
| 4,360,019 A | 11/1982 | Portner et al. |
| 4,378,015 A | 3/1983 | Wardlaw |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,755,172 A | 7/1988 | Baldwin |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,874,382 A | 10/1989 | Lindemann et al. |
| 4,894,054 A | 1/1990 | Miskinyar |
| 4,906,235 A | 3/1990 | Roberts |
| 4,906,463 A | 3/1990 | Cleary |
| 4,915,695 A | 4/1990 | Koobs |
| 4,941,880 A | 7/1990 | Burns |
| 4,955,871 A | 9/1990 | Thomas |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,096,715 A | 3/1992 | Sinclair |
| 5,104,380 A | 4/1992 | Holman et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,271,527 A | 12/1993 | Haber et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,343,519 A | 8/1994 | Feldman |
| 5,344,407 A | 9/1994 | Ryan |
| 5,354,284 A | 10/1994 | Haber et al. |
| 5,354,286 A | 10/1994 | Mesa et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,399,163 A | 3/1995 | Peterson et al. |
| 5,405,362 A | 4/1995 | Kramer et al. |
| 5,417,660 A | 5/1995 | Martin |
| 5,451,210 A | 9/1995 | Kramer et al. |
| 5,466,217 A | 11/1995 | Myers et al. |
| 5,514,135 A | 5/1996 | Earle |
| 5,540,664 A | 7/1996 | Wyrick |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,587,381 A | 12/1996 | Sinclair |
| 5,610,992 A | 3/1997 | Hickman |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,681,292 A | 10/1997 | Tober et al. |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |

(56) References Cited

U.S. PATENT DOCUMENTS

| | | |
|---|---|---|
| 5,728,074 A | 3/1998 | Castellano et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,813,570 A | 9/1998 | Fuchs et al. |
| 5,814,020 A | 9/1998 | Gross |
| 5,823,346 A | 10/1998 | Weiner |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,866,154 A | 2/1999 | Bahal |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,050,977 A | 4/2000 | Adams |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,503 A | 8/2000 | Stradella |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,280,421 B1 | 8/2001 | Kirchhofer et al. |
| 6,284,765 B1 | 9/2001 | Caffrey |
| 6,312,412 B1 | 11/2001 | Saied et al. |
| 6,317,630 B1 | 11/2001 | Gross et al. |
| 6,321,070 B1 | 11/2001 | Clark et al. |
| 6,321,654 B1 | 11/2001 | Robinson |
| 6,321,942 B1 | 11/2001 | Krampen et al. |
| 6,323,780 B1 | 11/2001 | Morris |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,382,465 B1 | 5/2002 | Greiner-Perth |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,425,499 B1 | 7/2002 | Guiffray |
| 6,425,897 B2 | 7/2002 | Overes et al. |
| 6,428,517 B1 | 8/2002 | Hochman et al. |
| 6,428,528 B2 | 8/2002 | Sadowski |
| 6,446,839 B1 | 9/2002 | Ritsche |
| 6,475,181 B1 | 11/2002 | Potter et al. |
| 6,478,769 B1 | 11/2002 | Parker |
| 6,478,771 B1 | 11/2002 | Lavi et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,233 B1 | 4/2003 | Fukui et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,610,271 B2 | 8/2003 | Wermeling |
| 6,613,010 B2 | 9/2003 | Castellano |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,150 B2 | 12/2003 | Hill et al. |
| 6,673,035 B1 | 1/2004 | Rice et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,706,019 B1 | 3/2004 | Parker et al. |
| 6,707,763 B2 | 3/2004 | Osberg et al. |
| 6,708,050 B2 | 3/2004 | Carim |
| 6,708,846 B1 | 3/2004 | Fuchs et al. |
| 6,722,916 B2 | 4/2004 | Buccinna et al. |
| 6,723,077 B2 | 4/2004 | Pickup et al. |
| 6,726,657 B1 | 4/2004 | Dedig et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,784,798 B2 | 8/2004 | Morris |
| 6,786,875 B2 | 9/2004 | Barker et al. |
| 6,786,885 B2 | 9/2004 | Hochman et al. |
| 6,793,646 B1 | 9/2004 | Giambattista et al. |

(56) References Cited

U.S. PATENT DOCUMENTS

| | | | |
|---|---|---|---|
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,945,961 B2 | 9/2005 | Miller et al. |
| 6,946,299 B2 | 9/2005 | Neel et al. |
| 6,948,492 B2 | 9/2005 | Wermeling et al. |
| 6,949,082 B2 | 9/2005 | Langley et al. |
| 6,950,028 B2 | 9/2005 | Zweig |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,074,211 B1 | 7/2006 | Heiniger et al. |
| 7,093,595 B2 | 8/2006 | Nesbitt |
| 7,102,526 B2 | 9/2006 | Zweig |
| 7,104,972 B2 | 9/2006 | Moller et al. |
| 7,113,101 B2 | 9/2006 | Peterson et al. |
| 7,116,233 B2 | 10/2006 | Zhurin |
| 7,126,879 B2 | 10/2006 | Snyder |
| 7,158,011 B2 | 1/2007 | Brue |
| 7,158,040 B2 | 1/2007 | Morris |
| 7,190,988 B2 | 3/2007 | Say |
| 7,191,916 B2 | 3/2007 | Clifford et al. |
| 7,229,458 B2 | 6/2007 | Boecker et al. |
| 7,237,549 B2 | 7/2007 | Stradella |
| 7,299,981 B2 | 11/2007 | Hickle et al. |
| 7,343,914 B2 | 3/2008 | Abrams et al. |
| 7,357,790 B2 | 4/2008 | Hommann et al. |
| 7,416,540 B2 | 8/2008 | Edwards et al. |
| 7,465,294 B1 | 12/2008 | Vladimirsky |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,648,482 B2 | 1/2010 | Edwards et al. |
| 7,648,483 B2 | 1/2010 | Edwards et al. |
| 7,670,328 B2 | 3/2010 | Miller et al. |
| 7,674,246 B2 | 3/2010 | Gillespie et al. |
| 7,708,719 B2 | 5/2010 | Wilmot et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,806,866 B2 | 10/2010 | Hommann et al. |
| 7,850,662 B2 | 12/2010 | Veasey et al. |
| 7,901,377 B1 | 3/2011 | Harrison et al. |
| 7,910,599 B2 | 3/2011 | Sinclair |
| 7,918,823 B2 | 4/2011 | Edwards et al. |
| 7,918,832 B2 | 4/2011 | Veasey et al. |
| 7,938,802 B2 | 5/2011 | Bicknell et al. |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,021,344 B2 | 9/2011 | Edwards et al. |
| 8,123,719 B2 | 2/2012 | Edwards et al. |
| 8,162,886 B2 | 4/2012 | Sadowski et al. |
| 8,198,291 B2 | 6/2012 | Wermeling |
| 8,206,360 B2 | 6/2012 | Edwards et al. |
| 8,226,610 B2 | 7/2012 | Edwards et al. |
| 8,231,573 B2 | 7/2012 | Edwards et al. |
| 8,313,466 B2 | 11/2012 | Edwards et al. |
| 8,348,096 B2 | 1/2013 | Greiner-Perth |
| 8,361,029 B2 | 1/2013 | Edwards et al. |
| 8,361,035 B2 | 1/2013 | Thorley et al. |
| 8,419,706 B2 | 4/2013 | Heldt et al. |
| 8,425,462 B2 | 4/2013 | Edwards et al. |
| 8,544,645 B2 | 10/2013 | Edwards et al. |
| 8,567,390 B2 | 10/2013 | Stadelhofer |
| 8,627,816 B2 | 1/2014 | Edwards et al. |
| 8,647,306 B2 | 2/2014 | Schwirtz et al. |
| 8,690,827 B2 | 4/2014 | Edwards et al. |
| 8,734,392 B2 | 5/2014 | Stadelhofer |
| 8,734,394 B2 | 5/2014 | Adams et al. |
| 8,747,357 B2 | 6/2014 | Stamp et al. |
| 8,920,377 B2 | 12/2014 | Edwards et al. |
| 8,926,594 B2 | 1/2015 | Edwards et al. |
| 8,939,943 B2 | 1/2015 | Edwards et al. |
| 9,022,022 B2 | 5/2015 | Edwards et al. |
| 9,022,980 B2 | 5/2015 | Edwards et al. |
| 9,056,170 B2 | 6/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards et al. |
| 2001/0005781 A1 | 6/2001 | Bergens et al. |
| 2001/0037087 A1 | 11/2001 | Knauer |
| 2002/0042596 A1 | 4/2002 | Hartlaub et al. |
| 2002/0072784 A1 | 6/2002 | Sheppard, Jr. et al. |
| 2002/0076679 A1 | 6/2002 | Aman |
| 2002/0079326 A1 | 6/2002 | Fuchs |
| 2002/0095120 A1 | 7/2002 | Larsen et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0105430 A1 | 6/2003 | Lavi et al. |
| 2003/0106824 A1 | 6/2003 | Wilmot et al. |
| 2003/0120212 A1 | 6/2003 | Dedig et al. |
| 2003/0120222 A1 | 6/2003 | Vaillancourt |
| 2003/0233070 A1 | 12/2003 | De La Serna et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0084047 A1 | 5/2004 | Hickle |
| 2004/0092874 A1 | 5/2004 | Mazidji |
| 2004/0094146 A1 | 5/2004 | Schiewe et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0180916 A1* | 9/2004 | Levine ............... A61K 31/485 514/282 |
| 2004/0210199 A1 | 10/2004 | Atterbury et al. |
| 2004/0220524 A1 | 11/2004 | Sadowski et al. |
| 2004/0235731 A1 | 11/2004 | Lundgren et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0038062 A1 | 2/2005 | Burns et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0090782 A1 | 4/2005 | Marshall et al. |
| 2005/0092679 A1 | 5/2005 | Warby |
| 2005/0101912 A1 | 5/2005 | Faust et al. |
| 2005/0134433 A1 | 6/2005 | Sweeney, II |
| 2005/0148931 A1 | 7/2005 | Juhasz |

(56) References Cited

U.S. PATENT DOCUMENTS

| | | |
|---|---|---|
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0177111 A1 | 8/2005 | Ozeri et al. |
| 2005/0182358 A1 | 8/2005 | Veit et al. |
| 2005/0183982 A1 | 8/2005 | Giewercer |
| 2005/0186221 A1 | 8/2005 | Reynolds et al. |
| 2005/0192530 A1 | 9/2005 | Castellano |
| 2005/0197654 A1 | 9/2005 | Edman et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0083691 A1 | 4/2006 | Wermeling |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0233778 A1 | 10/2006 | Lundgren et al. |
| 2006/0235354 A1 | 10/2006 | Kaal et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0135767 A1 | 6/2007 | Gillespie, III et al. |
| 2007/0148097 A1 | 6/2007 | Finn et al. |
| 2007/0166187 A1 | 7/2007 | Song et al. |
| 2007/0184847 A1 | 8/2007 | Hansen et al. |
| 2007/0185053 A1 | 8/2007 | Linn |
| 2007/0210147 A1 | 9/2007 | Morrone et al. |
| 2007/0212307 A1 | 9/2007 | Wermeling et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0261695 A1 | 11/2007 | Kottayil et al. |
| 2007/0265568 A1 | 11/2007 | Tsals et al. |
| 2007/0293826 A1 | 12/2007 | Wall et al. |
| 2008/0111685 A1 | 5/2008 | Olson et al. |
| 2008/0171995 A1 | 7/2008 | Vitullo et al. |
| 2008/0188798 A1 | 8/2008 | Weber |
| 2008/0228143 A1 | 9/2008 | Stamp |
| 2008/0230057 A1 | 9/2008 | Sutherland |
| 2008/0255513 A1 | 10/2008 | Kaal et al. |
| 2008/0262443 A1 | 10/2008 | Hommann et al. |
| 2009/0093759 A1 | 4/2009 | Judd et al. |
| 2009/0143761 A1 | 6/2009 | Cantor et al. |
| 2009/0176834 A1 | 7/2009 | Kottayil et al. |
| 2009/0192486 A1 | 7/2009 | Wilmot et al. |
| 2009/0221962 A1 | 9/2009 | Kaal et al. |
| 2009/0240200 A1 | 9/2009 | Heneveld et al. |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0211005 A1 | 8/2010 | Edwards et al. |
| 2010/0212663 A1 | 8/2010 | Vedrine et al. |
| 2010/0286612 A1 | 11/2010 | Cirillo |
| 2010/0331354 A1 | 12/2010 | Wermeling et al. |
| 2011/0060274 A1 | 3/2011 | Kuhn |
| 2011/0077589 A1 | 3/2011 | Karlsson et al. |
| 2011/0092954 A1 | 4/2011 | Jennings |
| 2011/0098655 A1 | 4/2011 | Jennings et al. |
| 2011/0189259 A1 | 8/2011 | Vasisht et al. |
| 2011/0295215 A1 | 12/2011 | Nielsen et al. |
| 2012/0046613 A1 | 2/2012 | Plumptre |
| 2012/0070495 A1 | 3/2012 | Shah et al. |
| 2012/0091026 A1 | 4/2012 | Chacornac et al. |
| 2012/0107783 A1 | 5/2012 | Julian et al. |
| 2012/0116319 A1 | 5/2012 | Grunhut |
| 2012/0172818 A1 | 7/2012 | Harms et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0270895 A1 | 10/2012 | Wermeling |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0302966 A1 | 11/2012 | Vedrine et al. |
| 2012/0310168 A1 | 12/2012 | Plumptre et al. |
| 2012/0310206 A1 | 12/2012 | Kouyoumjian et al. |
| 2012/0325865 A1 | 12/2012 | Forstreuter et al. |
| 2012/0330244 A1 | 12/2012 | Helmer et al. |
| 2013/0030367 A1 | 1/2013 | Wotton et al. |
| 2013/0060231 A1 | 3/2013 | Adlon et al. |
| 2013/0060232 A1 | 3/2013 | Adlon et al. |
| 2013/0079718 A1 | 3/2013 | Shang et al. |
| 2013/0079725 A1 | 3/2013 | Shang et al. |
| 2013/0081953 A1 | 4/2013 | Bruna et al. |
| 2013/0110050 A1 | 5/2013 | Boyd et al. |
| 2013/0236872 A1 | 9/2013 | Laurusonis et al. |
| 2013/0266919 A1 | 10/2013 | Baker et al. |
| 2013/0317477 A1 | 11/2013 | Edwards et al. |
| 2015/0018379 A1 | 1/2015 | Strang et al. |
| 2015/0041496 A1 | 2/2015 | Kim et al. |
| 2015/0231336 A1 | 8/2015 | Edwards et al. |
| 2015/0297840 A1 | 10/2015 | Edwards et al. |
| 2016/0015895 A1 | 1/2016 | Edwards et al. |
| 2017/0232206 A1 | 8/2017 | Edwards et al. |
| 2017/0333422 A1* | 11/2017 | Silverman ............ C07D 221/28 |
| 2018/0126082 A1 | 5/2018 | Edwards et al. |

FOREIGN PATENT DOCUMENTS

| | | |
|---|---|---|
| EP | 0346830 B1 | 5/1995 |
| EP | 1084765 B1 | 3/2001 |
| EP | 1287840 A1 | 3/2003 |
| EP | 1462134 A1 | 9/2004 |
| EP | 1712178 A2 | 10/2006 |
| GB | 2195544 A1 | 4/1988 |
| WO | WO 91/04760 | 4/1991 |
| WO | WO 93/02720 | 2/1993 |
| WO | WO 95/13838 | 5/1995 |
| WO | WO 95/26009 | 9/1995 |
| WO | WO 95/35126 | 12/1995 |
| WO | WO 97/30742 | 8/1997 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |
| WO | WO 2001/093926 | 12/2001 |
| WO | WO 2002/011778 | 2/2002 |
| WO | WO 2002/024257 | 3/2002 |
| WO | WO 2002/051471 | 7/2002 |
| WO | WO 2002/083205 | 10/2002 |
| WO | WO 2002/083212 | 10/2002 |
| WO | WO 2003/011378 | 2/2003 |
| WO | WO 2003/013632 | 2/2003 |
| WO | WO 2003/057283 | 7/2003 |
| WO | WO 2003/070191 | 8/2003 |
| WO | WO 2003/095001 | 11/2003 |
| WO | WO 2003/097133 | 11/2003 |
| WO | WO 2004/041330 | 5/2004 |
| WO | WO 2004/047890 | 6/2004 |
| WO | WO 2004/047891 | 6/2004 |

(56) References Cited

FOREIGN PATENT DOCUMENTS

| | | |
|---|---|---|
| WO | WO 2004/047892 | 6/2004 |
| WO | WO 2004/047893 | 6/2004 |
| WO | WO 2004/054644 | 7/2004 |
| WO | WO 2005/020906 | 3/2005 |
| WO | WO 2005/050526 | 6/2005 |
| WO | WO 2005/070481 | 8/2005 |
| WO | WO 2005/077441 | 8/2005 |
| WO | WO 2006/045525 | 5/2006 |
| WO | WO 2006/085175 | 8/2006 |
| WO | WO 2006/085204 | 8/2006 |
| WO | WO 2006/109778 | 10/2006 |
| WO | WO 2006/125692 | 11/2006 |
| WO | WO 2007/032962 | 3/2007 |
| WO | WO 2007/083115 | 7/2007 |
| WO | WO 2007/088444 | 8/2007 |
| WO | WO 2008/005315 | 1/2008 |
| WO | WO 2008/034060 | 3/2008 |
| WO | WO 2008/148864 | 12/2008 |
| WO | WO 2009/040595 | 4/2009 |

OTHER PUBLICATIONS

Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947>, 3 pages.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >, 2 pages.

"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.

Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.

Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.

Heartsine Technology, samaritan™ PAD Accessories [online] [retrieved on Jun. 1, 2007] Retrieved from the Internet <URL: http://www.heartsine.com/aboutsam-accessories.htm>, 4 pages.

CliniSense Corporation, "Drug delivery devices a potentially harsh environment for drugs," Stability [online] [retrieved on Jun. 1, 2007] Retrieved from the Internet <URL: http://www.clinisense.com/devices.htm>, 2 pages.

CliniSense Corporation, "LifeTrack Technology a new method to detect improper storage." Stability [online] [retrieved on Jun. 1, 2007] Retrieved from the Internet <URL: http://www.clinisense.com/tech.htm>, 2 pages.

AED Professionals™ Brochure [online] [retrieved on Jun. 1, 2007] Retrieved from the Internet <URL: http://www.aedprofessionals.com>, 4 pages.

Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >, 8 pages.

O'Hagan, D. et al., "Novel approaches to pediatric vaccine delivery," Advanced Drug Delivery Reviews, 58:29-51 (2006).

Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.

Boseley, S., "Families to receive antidote to help drug users who overdose," Guardian News and Media, Jun. 25, 2009. [retrieved on May 27, 2011] Retrieved from the Internet <URL: http://www.guardian.co.uk/society/2009/jun/25/drug-overdose-antidote-naloxone-families>.

McDougall, L., "Addicts to be given personal supply of anti-overdose drug," The Herald Scotland, May, 28, 2006. Retrieved from the Internet <URL: http://www.heraldscotland.com/sport/spl/aberdeen/addicts-to-be-given-personal-supply-of-anti-overdose-drug-heroin-controversial-lifesaving-plan-projects-aim-to-cut-rising-death-toll-by-making-naloxone-treatment-more-readily-available-1.19181>, 3 pages.

BD Accuspray™ Nasal Spray System, 2004, Retrieved from the Internet <URL: http://www.bd.com/press/pds/flu/bd_accuspray.pdf>, 1 page.

Colliver, V., "Naloxone saves lives of overdosed opiate users," San Francisco Chronicle, Oct. 14, 2010 [retrieved Aug. 14, 2013] Retrieved from the Internet <URL: http://www.sfgate.com/health/article/Naloxone-saves-lives-of-overdosed-opiate-users-3249978.php>.

Terry, D., "A Shot That Saves the Lives of Addicts Is Now in Their Hands," The New York Times, Jul. 24, 2010 [retrieved Aug. 14, 2013] Retrieved from the Internet <URL: http://www.nytimes.com/2010/07/25/us/25cncnaloxone.html>.

Szalavitz, M., "Should an Overdose Antidote Be Made More Accessible?" Time, Dec. 9, 2010 [retrieved on Aug. 14, 2013] Retrieved from the Internet <URL: http://healthland.time.com/2010/12/09/should-an-overdose-antidote-be-made-more-accessible/>.

Okie, S., "A Flood of Opioids, a Rising Tide of Deaths," The New England Journal of Medicine, Nov. 18, 2010, 363:1981-1985 [online], [retrieved on Aug. 14, 2013] Retrieved from the Internet <URL: http://www.nejm.org/doi/full/10.1056/NEJMp1011512>.

Wermeling, D. P., "A response to the opioid overdose epidemic: naloxone nasal spray," Drug Deliv. and Transl. Res., 3:63-74 (2013).

Wermeling, D. P., "Opioid Harm Reduction Strategies: Focus on Expanded Access to Intranasal Naloxone," Pharmacotherapy, 30(7):627-631 (2010).

Djupesland, P. G., "Nasal drug delivery devices: characteristics and performance in a clinical perpsective—a review," Drug Deliv. and Transl. Res., Published online: Oct. 18, 2012, 21 pages.

"Martindale Pharma Launches Prenoxad Injection in UK for Emergency Treatment of Opioid Overdose," Pharmabiz.com, May 6, 2013 [online], [retrieved on Nov. 26, 2014] Retrieved from the Internet <URL: http://www.pharmabiz.com/NewsDetails.aspx?aid=75187&sid=2>, 1 page.

"Therapeutic Intranasal Drug Delivery: Needleless Treatment Options for Medical Problems," Intranasal.net [online], [retrieved on Dec. 16, 2010] Retrieved from the Internet <URL: http://intranasal.net/OpiateOverdose/>, 10 pages.

(56) References Cited

OTHER PUBLICATIONS

Prenoxad Injection: Client's Guide to Prenoxad Injection, Martindale Pharma, Apr. 2013, 16 pages.
Prenoxad Injection: Pharmacists's Guide, Martindale Pharma, Apr. 2013, 6 pages.
Prenoxad Injection: Packaging Leaflet: Information for the User, Martindale Pharma, Nov. 2012, 2 pages.
Prenoxad Injection: Summary of Product Characteristics, Martindale Pharma, Apr. 2013, 4 pages.
Edwards, E. S., Dissertation: "Development of a novel approach to assess qualitative and quantitative dynamics associated with the subcutaneous or intramuscular administration of pharmaceuticals and associated parenteral delivery systems," B.S. Biology, Virginia Commonwealth University (Dec. 2011), 316 pages.
Bennett, J. et al., "Subcutaneous administration of midazolam: A comparison of the bioject jet injector with the conventional syringe and needle," J Oral Maxillofac Surg, 56(11):1249-1254 (1998).
Brearley, C. et al., "Pharmacokinetics of recombinant human growth hormone administered by cool.clickTM 2, a new needle-free device, compared with subcutaneous administration using a conventional syringe and needle," BMC Clin Pharmacol, 7:10 (2007), 7 pages.
Simons, F. E. R. et al., "Epinephrine absorption in adults: intramuscular versus subcutaneous injection," J Allergy Clin Immunol, 108(5), 871-873 (2001).
Kerum, G. et al., "Blood glucose and free insulin levels after the administration of insulin by conventional syringe or jet injector in insulin treated type 2 diabetics," Horm. Metabol. Res., 19:422-425 (1987).
Halle, J.-P. et al., "Twice daily mixed regular and NPH insulin injections with new jet injector versus conventional syringes: pharmacokinetics of insulin absorption," Diabetes Care, 9(3):279-282 (1986).
Taylor, R. et al., "Plasma free insulin profiles after administration of insulin by jet and conventional syringe injection," Diabetes Care, 4(3):377-379 (1981).
Biocryst Pharmaceuticals, Inc., Biocryst Press Release, "Biocryst reports preliminary results from a phase II clinical trial of peramivir in subjects with acute influenza," Retrieved from the Internet: <http://investor.shareholder.com/biocryst/releasedetail.cfm?ReleaseID=264815> (Sep. 19, 2007), 3 pages.
Marx, D. et al., "Multi-Dose Container for Nasal and Ophthalmic Drugs: A Preservative Free Future?," Chapter 20 of Drug Development—A Case Study Based Insight into Modern Strategies, isBN: 978-953-307-257-9 (Nov. 2011).
Harm Reduction Coalition, "How to Give Nasal Spray Naloxone," [online], [retrieved on May 27, 2015] Retrieved from the Internet: <http://http://harmreduction.org/wp-content/uploads/2014/10/OD-Response-administer-naloxone-intranasal-instructions.pdf> (undated).

Elsemiek, E.C. et al., "Improved Pharmacokinetic and Pharmacodynamic Profile of Rapid-Acting Insulin Using Needle-Free Jet Injection Technology," Emerging Treatments and Technologies, *Diabetes Care* 34:1804-1808 (Aug. 2011).
Lewis, J. et al., "Needle-Free Subcutaneous Sumatriptan (Sumavel™ DosePro™ Bioequivalence and Ease of Use," *Headache*, 2009;49:1435-1444 (Nov./Dec. 2009).
Schram, J. et al., "Transdermal Drug Delivery by Jet Injectors: Energetics of Jet Formation and Penetration," *Pharmaceutical Research*, vol. 19, No. 11 (Nov. 2002).
Verhagen, A. et al., A1032:C1038 "Pharmacokinetics and pharmacodynamics of a single dose of recombinant human growth hormone after subcutaneous administration by jet-injection: comparison with conventional needle-injection," Eur J Clin Pharmacol 49:69-72 (Feb. 10, 1995).
Dahan, Albert et al., "Incidence, Reversal, and Prevention of Opioid-induced Respiratory Depression," *Anesthesiology* vol. 112, No. 1: 226-238 (Jan. 2010).
Clarke, S.F.J. et al., "Naloxone in Opioid Poisoning: Walking the tightrope," *Emerg Med J* vol. 22: 612-616 (2005).
International Search Report and Written Opinion for International Patent Application No. PCT/US06/03415, dated Jul. 13, 2006, 10 pages.
International Search Report and Written Opinion for International Patent Application No. PCT/US07/007626, dated Sep. 29, 2008.
Examination Report for Australian Patent Application No. 2011218756, dated Nov. 1, 2011.
Examination Report for Australian Patent Application No. 2011218756, dated Feb. 1, 2013.
Notice of Acceptance for Australian Patent Application No. 2011218756, dated Apr. 12, 2013.
Non-Final Office Action for U.S. Appl. No. 13/036,720, dated May 17, 2013.
Final Office Action for U.S. Appl. No. 13/036,720, dated Nov. 5, 2013.
International Search Report and Written Opinion for International Application No. PCT/US2012/026708, dated Jun. 7, 2012.
Non-Final Office Action for U.S. Appl. No. 14/062,516, dated Apr. 22, 2014.
Final Office Action for U.S. Appl. No. 14/062,516, dated Sep. 23, 2014.
Office Action for U.S. Appl. No. 14/153,575, dated Jan. 30, 2015.
Office Action for U.S. Appl. No. 14/335,490, dated May 8, 2015.
Office Action for U.S. Appl. No. 14/694,725, dated Dec. 17, 2015.
Office Action for British Patent Application No. 1315737.5, dated Feb. 28, 2017.
Search Report for European Patent Application No. 12751771.2, dated Jun. 13, 2017.
Office Action for U.S. Appl. No. 14/605,512, dated Aug. 10, 2017.

\* cited by examiner

MEDICAMENT DELIVERY DEVICE FOR ADMINISTRATION OF OPIOID ANTAGONISTS INCLUDING FORMULATIONS FOR NALOXONE

CROSS-REFERENCE TO RELATED APPLICATIONS

This application is a continuation of U.S. patent application Ser. No. 14/694,725, filed Apr. 23, 2015, which is a continuation of U.S. patent application Ser. No. 14/153,575, filed Jan. 13, 2014, now U.S. Pat. No. 9,022,022, which is a continuation of U.S. patent application Ser. No. 13/036,720, filed Feb. 28, 2011, now U.S. Pat. No. 8,627,816, each entitled "Medicament Delivery Device for Administration of Opioid Antagonists Including Formulations for Naloxone," and each of which is incorporated herein by reference in its entirety.

BACKGROUND

The embodiments described herein relate generally to medical device and pharmaceutical compositions, and more particularly to a medicament delivery device for administration of opioid antagonists, including formulations for naloxone.

Naloxone is a medicament that prevents and/or reverses the effects of opioids. Known formulations of naloxone can be used, for example, to treat respiratory depression and other indications that result from opioid toxicity. For example, known formulations for naloxone can be used to reverse and/or mitigate the effects of an overdose of a drug containing opioids, such as, for example, heroin. In such situations, it is desirable to deliver the naloxone formulation quickly and in a manner that will produce a rapid onset of action. Accordingly, known formulations of naloxone are often delivered either intranasally or via injection.

The delivery of naloxone intranasally or via injection, however, often involves completing a series of operations that, if not done properly, can limit the effectiveness of the naloxone formulation. For example, prior to delivering the naloxone, the user must first determine whether the patient's symptoms warrant the delivery of naloxone, and then couple a needle (or an atomizer) to a syringe containing the naloxone formulation. After the device is prepared for delivery, the user then selects the region of the body in which the naloxone is to be delivered, and manually produces a force to deliver the naloxone. In some situations, such as, for example, when the patient is in an ambulance or a hospital setting, the user then inserts an intravenous catheter to administer the naloxone. Additionally, after the delivery of the naloxone formulation, the user must dispose of the device properly (e.g., to prevent needle sticks in instances where the naloxone is injected) and seek further medical attention for the patient. Accordingly, known formulations of naloxone are often delivered by a healthcare provider in a controlled environment (e.g. a hospital, physician's office, clinic or the like). Access to emergency medical facilities and/or trained health care providers, however, is not always available when an individual is suffering from an overdose. Moreover, because naloxone is often administered during an emergency situation, even experienced and/or trained users may be subject to confusion and/or panic, thereby compromising the delivery of the naloxone formulation.

Known devices for delivering naloxone also require that the user manually generate the force and/or pressure required to convey the naloxone from the device into the body. For example, to deliver naloxone using known syringes, the user manually depresses a plunger into the syringe body. The force generated by manually depressing a plunger, however, can be sporadic, thus resulting in undesirable fluctuations in the flow of the naloxone and/or incomplete delivery of the full dose. Such fluctuations and variability can be particularly undesirable when the naloxone is being atomized for intranasal delivery. Moreover, in certain situations, the user may be unable to generate sufficient force to provide the desired flow rate and/or flow characteristics (e.g., for an atomizer) of the naloxone.

Additionally, because naloxone is often delivered by a healthcare provider in a controlled environment, known formulations of naloxone are generally stored under controlled conditions, and for limited periods of time. For example, known naloxone formulations are often formulated to be stored between 20 and 25 degrees Celsius. Accordingly, known naloxone formulations are not compatible for being carried by a patient or a third party (e.g., a relative of friend of the patient) for long periods of time.

Thus, a need exists for improved methods and devices for delivering opioid antagonists, such as, for example, devices that provide for the delivery of naloxone by untrained users. Additionally, a need exists for naloxone formulations that can be exposed to a wide range of environmental conditions for long periods of time.

SUMMARY

Medicament delivery devices for administration of opioid antagonists and chemical compositions used within such devices are described herein. In some embodiments, a naloxone composition can be formulated for use in a delivery device of the types shown and described herein. The naloxone composition includes an effective amount of naloxone i.e., 4,5-epoxy-3,14-dihydroxy-17-(2-propenyl) morphinan-6-one, or a pharmaceutically acceptable salt and/or ester thereof. As used herein, an "effective amount" is an amount sufficient to provide a desired therapeutic effect. In some embodiments, the naloxone composition can include a pH adjusting agent, such as, for example, at least one of hydrochloric acid, citric acid, acetic acid, phosphoric acid, or combinations thereof. In some embodiments, the naloxone composition can include one or more tonicity-adjusting agents, such as, for example, at least one of dextrose, glycerin, mannitol, potassium chloride, sodium chloride, or combinations thereof. Because the naloxone composition may be stored in the medicament container of a delivery device for extended periods of time under varying storage conditions, in some embodiments the naloxone composition can include stabilizers to prevent or inhibit decomposition of the naloxone during storage.

In some embodiments, an apparatus includes a housing, a medicament container disposed within the housing and an energy storage member disposed within the housing. The medicament container is filled with a naloxone composition that includes naloxone or salts thereof, a tonicity-adjusting agent, and a pH adjusting agent, whereby the osmolality of the naloxone composition ranges from about 250-350 mOsm and the pH ranges from about 3-5. The energy storage member is configured to produce a force to deliver the naloxone composition.

In some embodiments, the medicament delivery device can further include an elastomeric member disposed within the medicament container that is configured to be compatible with the naloxone composition. Said another way, in some embodiments, an elastomeric member disposed within the medicament container can be formulated to prevent undesired leaching and/or reaction with the naloxone composition. In some embodiments, the elastomeric member is formulated to include a polymer and a curing agent. The polymer includes at least one of bromobutyl or chlorobutyl, and the curing agent includes at least one of sulfur or metal compounds, e.g., metal oxides such as zinc oxide or magnesium oxide, etc.

In some embodiments, the medicament delivery device can include an electronic circuit system coupled to the housing. The electronic circuit system is configured to produce an output when the electronic circuit system is actuated. The output can be, for example, an audible or visual output related to the naloxone composition (e.g., an indication of the expiration date, the symptoms requirement treatment with naloxone or the like), the use of the medicament delivery device, and/or post-administration procedures (e.g., a prompt to call 911, instructions for the disposal of the device or the like).

DETAILED DESCRIPTION

Figure 1:
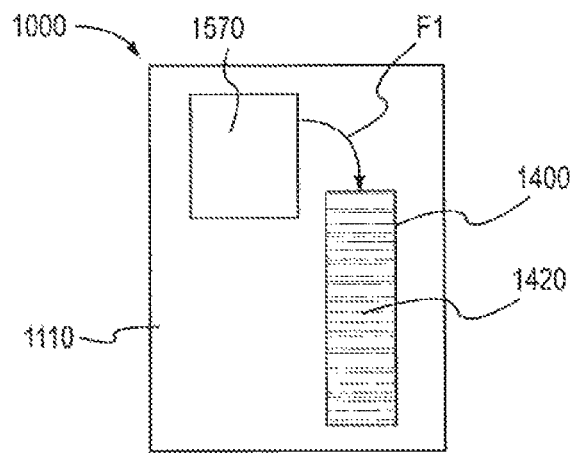
FIG. 1 is a schematic illustration of a medicament delivery device according to an embodiment.

Medicament delivery devices for administration of opioid antagonists and chemical compositions used within such devices are described herein. In some embodiments, a naloxone composition can be formulated for use in a delivery device of the types shown and described herein. The naloxone composition includes an effective amount of naloxone i.e., 4,5-epoxy-3,14-dihydroxy-17-(2-propenyl) morphinan-6-one, or a pharmaceutically acceptable salt and/or ester thereof. As used herein, an "effective amount" is an amount sufficient to provide a desired therapeutic effect. In some embodiments, the naloxone composition can include a pH adjusting agent, such as, for example, at least one of hydrochloric acid, citric acid, acetic acid, phosphoric acid, or combinations thereof. In some embodiments, the naloxone composition can include one or more tonicity-adjusting agents, such as, for example, at least one of dextrose, glycerin, mannitol, potassium chloride, sodium chloride, or combinations thereof. Because the naloxone composition may be stored in the medicament container of a delivery device for extended periods of time under varying storage conditions, in some embodiments the naloxone composition can include stabilizers to prevent or inhibit decomposition of the naloxone during storage.

In some embodiments, a medicament delivery device includes a housing, a medicament container disposed within the housing and an energy storage member disposed within the housing. The medicament container is filled with a naloxone composition that includes naloxone or salts thereof, a tonicity-adjusting agent, and a pH adjusting agent, whereby the osmolality of the naloxone composition ranges from about 250-350 mOsm and the pH ranges from about 3-5. The energy storage member is configured to produce a force to deliver the naloxone composition.

In some embodiments, the medicament delivery device can further include an elastomeric member disposed within the medicament container that is configured to be compatible with the naloxone composition. Said another way, in some embodiments, an elastomeric member disposed within the medicament container can be formulated to prevent undesired leaching and/or reaction with the naloxone composition. In some embodiments, the elastomeric member is formulated to include a polymer and a curing agent. The polymer includes at least one of bromobutyl or chlorobutyl, and the curing agent includes at least one of sulfur, zinc or magnesium.

In some embodiments, the medicament delivery device can include an electronic circuit system coupled to the housing. The electronic circuit system is configured to produce an output when the electronic circuit system is actuated. The output can be, for example, an audible or visual output related to the naloxone composition (e.g., an indication of the expiration date, the symptoms requirement treatment with naloxone or the like), the use of the medicament delivery device, and/or post-administration procedures (e.g., a prompt to call 911, instructions for the disposal of the device or the like).

In some embodiments, a medicament delivery device includes a housing, a medicament container disposed within the housing, a delivery member coupled to the medicament container, and an energy storage member. The medicament container is filled with a naloxone composition. The energy storage member is disposed within the housing, and is configured to produce a force to deliver the naloxone composition from the medicament container via the delivery member such that the delivery member atomizes the naloxone composition.

In some embodiments, a kit includes a case and a medicament container movably disposed within the case. The medicament container filled with a naloxone composition. The medicament container includes a delivery member coupled thereto. The delivery member can be, for example, a needle, an atomizer or any other mechanism through which the naloxone composition can be conveyed from the medicament container into a body.

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±7%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 70-70, etc.). Furthermore, all values within a given range may be an endpoint for the range encompassed thereby (e.g., the range 50-80 includes the ranges with endpoints such as 55-80, 50-75, etc.).

Throughout the present specification, the words "a" or "an" are understood to mean "one or more" unless explicitly stated otherwise. Further, the words "a" or "an" and the phrase "one or more" may be used interchangeably.

Compositions

In one aspect, the present disclosure relates to compositions comprising naloxone or a pharmaceutically acceptable salt thereof suitable for use in the medicament delivery devices disclosed herein. Accordingly, the present naloxone compositions may be adapted for various administration routes, depending on the apparatus in which such composition(s) are to be employed. For example, in some embodiments, the present compositions may be adapted for transmucosal administration as, e.g., a nasal spray, or alternatively as a sublingual or buccal spray. In other embodiments, the present naloxone compositions may be adapted for parenteral administration as, e.g., an injectable solution.

The present compositions generally comprise an effective amount of naloxone, i.e., 4,5-epoxy-3,14-dihydroxy-17-(2-propenyl) morphinan-6-one, or a pharmaceutically acceptable salt and/or ester thereof. As used herein, an "effective amount" is an amount sufficient to provide a desired therapeutic effect. For example, as described herein, the present naloxone compositions may be useful in treating respiratory depression and/or other indications associated with opioid toxicity. Accordingly, an effective amount of naloxone in the present compositions may be an amount sufficient to treat such respiratory depression and/or other indications associated with opioid toxicity. The present naloxone compositions typically have a concentration of 4,5-epoxy-3,14-dihydroxy-17-(2-propenyl)morphinan-6-one (or a salt and/or ester thereof) between about 0.01 mg/mL and about 10 mg/mL (e.g., between about 0.05 mg/mL and about 2 mg/mL, or any other value or range of values therein, including about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, or about 1.9 mg/mL).

In some embodiments, the present naloxone compositions comprise a pH adjusting agent. In some embodiments, the pH adjusting agent includes at least one of hydrochloric acid, citric acid, acetic acid, phosphoric acid, or combinations thereof. The pH adjusting agent may comprise an organic and/or inorganic acid or salt thereof (e.g., alkali metal salts [Li, Na, K, etc.], alkaline earth metal [e.g., Ca, Mg, etc.] salts, ammonium salts, etc.). In other embodiments, the pH adjusting agent includes mixtures of one or more acids and one or more salts thereof. e.g., citric acid and citrate salts, acetic acid and acetate salts, phosphoric acid and phosphate salts, etc. In certain embodiments, the pH adjusting agent is added in an amount sufficient to provide a pH of the present naloxone compositions of from about 3 to about 5 (for example a pH of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0). Accordingly, the present compositions may comprise naloxone salts of the pH adjusting agent employed. For example, in one embodiment, the pH adjusting agent is dilute aqueous hydrochloric acid, and the naloxone salt is naloxone.HCl (e.g., 4,5-epoxy-3,14-dihydroxy-17-(2-propenyl)-morphinan-6-one hydrochloride).

Solvents suitable for use in the present compositions are not particularly limited, provided they are pharmaceutically acceptable. Accordingly, any pharmaceutically acceptable solvent in which the components of the present compositions are soluble, and which does not adversely affect the stability of the present compositions and/or the naloxone and/or naloxone salts contained therein may be employed. For example, in a typical composition, the solvent is sterile water (e.g., USP grade water for injection [WFI]).

In some embodiments, the present compositions may also comprise one or more tonicity-adjusting agents. For example, the tonicity-adjusting agent may include at least one of dextrose, glycerin, mannitol, potassium chloride, sodium chloride, or combinations thereof. The tonicity-adjusting agent(s) may be present in an amount of from about 0.1 mg/mL to about 50 mg/mL (e.g., including about 0.5 mg/mL, about 1.0 mg/mL, about 2.0 mg/mL, about 3.0 mg/mL, about 4.0 mg/mL, about 5.0 mg/mL, about 10 mg/mL, about 15 mg/mL, about 20 mg/mL, about 25 mg/mL, about 30 mg/mL, about 35 mg/mL, about 40 mg/mL, or about 45 mg/mL). In one embodiment, the tonicity-adjusting agent is sodium chloride, and the concentration thereof is between about 0.1 mg/mL and about 20 mg/mL. Generally, in naloxone compositions as described herein which are adapted for injection and/or intranasal delivery, tonicity-adjusting agents are added to provide a desired osmolality. In some embodiments, the osmolality of the naloxone compositions described herein is from about 250 to about 350 mOsm.

Because the naloxone compositions disclosed herein may be stored in the medicament container of the devices described herein for extended periods of time under varying storage conditions, in some embodiments the present compositions may further comprise stabilizers to prevent or inhibit decomposition of the naloxone during storage. Various types of pharmaceutically acceptable stabilizers can be used, including antioxidants (e.g. substituted phenols such as BHT, TBHQ, BHA, or propyl gallate; ascorbates such as ascorboyl palmitate, sodium ascorbate, ascorbic acid), complexing agents (e.g., cyclodextrins); or chelating agents such as EDTA (and its salts), D-gluconic acid 6-lactone, sodium or potassium gluconate, sodium triphosphate, and sodium hexametaphosphate.

EXAMPLES

The chemical stability of several exemplary naloxone hydrochloride compositions were evaluated at various pH and temperature conditions. The formulation of six development lots was performed to evaluate pH and order of addition parameters for naloxone hydrochloride. Assay testing was performed on aliquots of bulk formulation solution sampled prior to the filtration process to determine if the filtration process contributed to any API losses.

Exemplary naloxone compositions were prepared according to the formulations set forth in Table 1, below:

TABLE 1

Exemplary Naloxone Formulations.

| Lot | Initial WFI (g) | Order of Addition | API Added (mg) | API Mix Time (seconds) | NaCl Added (g) | NaCl Mix Time (seconds) | Initial pH | Adjusted pH | Final pH | Volume of pH Adjuster (mL) | Final Weight (g) |
|---|---|---|---|---|---|---|---|---|---|---|---|
| 1 | 400.01 | A | 554.73 | 110 | 4.5000 | 98 | 5.52 | 3.01 | 2.99 | 4.1 | 500.00 |
| 2 | 400.15 | B | 555.10 | 86 | 4.5269 | 69 | 5.41 | 6.51 | 6.51 | 0.5 | 502.14 |
| 3 | 400.13 | A | 554.95 | 104 | 4.5033 | 58 | 5.39 | 4.47 | 4.47 | 0.2 | 502.17 |
| 4 | 400.00 | B | 554.53 | 82 | 4.4999 | 87 | 5.37 | 3.01 | 3.01 | 4.0 | 502.15 |
| 5 | 399.99 | A | 554.59 | 85 | 4.5513 | 74 | 5.40 | 6.49 | 6.49 | 0.2 | 502.16 |
| 6 | 400.02 | B | 554.81 | 68 | 4.5020 | 70 | 5.45 | 4.50 | 4.49 | 0.2 | 502.19 |

Final Formulation Solution Density = 1.0043 g/mL (Determined during the formulation process for Lot 1)
Order of Addition: A = Water, NaCl, naloxone hydrochloride, pH adjuster
B = Water, naloxone hydrochloride, NaCl, pH adjuster There were no noticeable differences between the formulations from lot to lot. The order of addition of the components had no observable impact on the dissolution times for either the API (Naloxone Hydrochloride) or the NaCl. Initial solution pH values indicated no observable differences between the solutions prior to final pH adjustment. The volumes required for the final pH adjustment were also consistent, indicating no significant differences between the lots.

Solutions were filtered after formulation to determine if filtration after formulation impacts overall solution API concentration. Pre-filtration assay values were consistent with the post-filtration (initial) assay results for each lot, as shown in Table 2, below:

TABLE 2

Filtration of Naloxone Formulations.

| Lot | Pre-Filtration Naloxone Hydrochloride (mg/mL) | Post-Filtration Naloxone Hydrochloride (mg/mL) |
|---|---|---|
| 1 | 1.02 | 1.02 |
| 2 | 1.00 | 1.00 |
| 3 | 1.01 | 1.00 |
| 4 | 1.02 | 1.01 |
| 5 | 1.00 | 0.99 |
| 6 | 1.01 | 0.99 |

Because the naloxone compositions described herein may be stored in the medicament container of the devices described herein for extended periods of time under varying storage conditions, initial testing was performed to support a stability study for the development lots of naloxone hydrochloride. Initial appearance, pH and assay results are shown in Table 3, below:

TABLE 3

Initial Appearance, pH and Assay Results

| Lot | Replicate | Appearance | Osmolality (mOsm) | pH | Assay (mg/mL) |
|---|---|---|---|---|---|
| 1 | 1 | Clear, colorless solution free of visible particulate matter | 295 | 3.09 | 1.02 |
|   | 2 | Clear, colorless solution free of visible particulate matter | 295 | 3.09 | 1.02 |
|   |   | Mean (n = 2) | 295 | 3.09 | 1.02 |
| 2 | 1 | Clear, colorless solution free of visible particulate matter | 294 | 6.54 | 1.00 |
|   | 2 | Clear, colorless solution free of visible particulate matter | 295 | 6.55 | 1.00 |
|   |   | Mean (n = 2) | 295 | 6.55 | 1.00 |
| 3 | 1 | Clear, colorless solution free of visible particulate matter | 292 | 4.92 | 1.00 |
|   | 2 | Clear, colorless solution free of visible particulate matter | 289 | 4.96 | 1.00 |
|   |   | Mean (n = 2) | 291 | 4.94 | 1.00 |
| 4 | 1 | Clear, colorless solution free of visible particulate matter | 294 | 3.13 | 1.01 |
|   | 2 | Clear, colorless solution free of visible particulate matter | 294 | 3.14 | 1.01 |
|   |   | Mean (n = 2) | 294 | 3.14 | 1.01 |
| 5 | 1 | Clear, colorless solution free of visible particulate matter | 295 | 6.57 | 0.99 |
|   | 2 | Clear, colorless solution free of visible particulate matter | 295 | 6.57 | 0.99 |
|   |   | Mean (n = 2) | 295 | 6.57 | 0.99 |
| 6 | 1 | Clear, colorless solution free of visible particulate matter | 292 | 4.95 | 0.99 |
|   | 2 | Clear, colorless solution free of visible particulate matter | 290 | 4.99 | 0.99 |
|   |   | Mean (n = 2) | 291 | 4.97 | 0.99 |

The pH analysis of Lots 3 and 7 exhibited increases of 0.4 and 0.5, respectively, in comparison to the pH values obtained during the formulation process. To verify the initial bulk pH, an aliquot of bulk formulation solution for Lot 7 was removed from storage at 5° C. and allowed to equilibrate to room temperature. The determined pH was 4.52, confirming the final pH obtained during the formulation process. Analysis of related substances was performed for each individual sample, as shown in Table 4, below:

TABLE 4

Initial Related Substance Screening Results

| Lot | Replicate | Unknown (Identified by RRT) | % Related Substance | Total Related Substances (%) | Mean of Total Related Substances (%) |
|---|---|---|---|---|---|
| 1 | 1 | NR | NR | NR | NR |
|   | 2 | NR | NR | NR |    |
| 2 | 1 | NR | NR | NR | NR |
|   | 2 | 0.559 | 0.05 | 0.05 |    |
| 3 | 1 | NR | NR | NR | NR |
|   | 2 | NR | NR | NR |    |
| 4 | 1 | NR | NR | NR | NR |
|   | 2 | NR | NR | NR |    |
| 5 | 1 | 0.160 | 0.11 | 0.17 | 0.09 |
|   |   | 0.559 | 0.06 |    |    |
|   | 2 | NR | NR | NR |    |
| 6 | 1 | NR | NR | NR | NR |
|   | 2 | NR | NR | NR |    |

NR = Not Reportable (<0.05% Impurity)

In Table 4, % Related Substance=(Related Substance Peak Area/Total Integrated Area)×100. Peaks greater than or equal to 0.05% were reported. Replicates that exhibited levels of related substances that were not reportable were treated as 0.00% for determination of mean total related substances.

One month stability testing was conducted as previously described, with the following additional analyses:
  pH analysis for all lots at the 25° C./60% RH condition
  pH analysis for lots 1 and 4 at the 40° C./75% RH condition Assay and Related Substances analysis for lots 1 and 4 at the 25° C./60% RH and 40° C./75% RH conditions

TABLE 5

One Month Stability Results - 70° C./75% RH

| Lot | Replicate | Appearance | pH | Assay (mg/mL) |
|---|---|---|---|---|
| 1 | 1 | Clear, colorless solution free of visible particulate matter | 3.28 | 1.02 |
|   | 2 | Clear, colorless solution free of visible particulate matter | 3.25 | 1.01 |
|   |   | Mean (n = 2) | 3.27 | 1.02 |
| 2 | 1 | Clear, colorless solution free of visible particulate matter | 6.05 | 0.94 |
|   | 2 | Clear, colorless solution free of visible particulate matter | 6.05 | 0.94 |
|   |   | Mean (n = 2) | 6.05 | 0.94 |
| 3 | 1 | Clear, colorless solution free of visible particulate matter | 5.32 | 0.97 |
|   | 2 | Clear, colorless solution free of visible particulate matter | 5.44 | 0.97 |
|   |   | Mean (n = 2) | 5.38 | 0.97 |
| 4 | 1 | Clear, colorless solution free of visible particulate matter | 3.28 | 1.01 |
|   | 2 | Clear, colorless solution free of visible particulate matter | 3.28 | 0.99 |
|   |   | Mean (n = 2) | 3.28 | 1.00 |
| 5 | 1 | Clear, colorless solution free of visible particulate matter | 6.06 | 0.94 |
|   | 2 | Clear, colorless solution free of visible particulate matter | 6.05 | 0.93 |
|   |   | Mean (n = 2) | 6.06 | 0.93 |
| 6 | 1 | Clear, colorless solution free of visible particulate matter | 5.41 | 0.95 |
|   | 2 | Clear, colorless solution free of visible particulate matter | 5.27 | 0.96 |
|   |   | Mean (n = 2) | 5.34 | 0.95 |

TABLE 7a

One Month Related Substances Results - 70° C./75% RH - Lots 1-3

| Lot | Replicate | Unknown (Identified by RRT) | % Related Substance | Total Related Substances (%) | Mean of Total Related Substances (%) |
|---|---|---|---|---|---|
| 1 | 1 | 0.038 | 0.11 | 0.42 | 0.46 |
|   |   | 0.404 | 0.19 |   |   |
|   |   | 0.597 | 0.12 |   |   |
|   | 2 | 0.038 | 0.13 | 0.50 |   |
|   |   | 0.404 | 0.23 |   |   |
|   |   | 0.597 | 0.14 |   |   |
| 2 | 1 | 0.034 | 0.08 | 4.94 | 4.77 |
|   |   | 0.038 | 0.21 |   |   |
|   |   | 0.089 | 0.08 |   |   |
|   |   | 0.118 | 0.08 |   |   |
|   |   | 0.136 | 4.23 |   |   |
|   |   | 0.403 | 0.11 |   |   |
|   |   | 1.029 | 0.15 |   |   |
|   | 2 | 0.034 | 0.07 | 4.59 |   |
|   |   | 0.038 | 0.17 |   |   |
|   |   | 0.089 | 0.08 |   |   |
|   |   | 0.136 | 4.04 |   |   |
|   |   | 0.403 | 0.10 |   |   |
|   |   | 1.028 | 0.13 |   |   |
| 3 | 1 | 0.038 | 0.19 | 2.79 | 2.94 |
|   |   | 0.118 | 0.06 |   |   |
|   |   | 0.136 | 2.17 |   |   |
|   |   | 0.403 | 0.15 |   |   |
|   |   | 0.596 | 0.06 |   |   |
|   |   | 1.026 | 0.17 |   |   |
|   | 2 | 0.038 | 0.19 | 3.09 |   |
|   |   | 0.117 | 0.05 |   |   |
|   |   | 0.136 | 2.46 |   |   |
|   |   | 0.403 | 0.15 |   |   |
|   |   | 0.596 | 0.05 |   |   |
|   |   | 1.024 | 0.19 |   |   |

TABLE 7b

One Month Related Substances Results - 70° C./75% RH - Lots 4-6

| Lot | Replicate | Unknown (Identified by RRT) | % Related Substance | Total Related Substances (%) | Mean of Total Related Substances (%) |
|---|---|---|---|---|---|
| 4 | 1 | 0.038 | 0.11 | 0.44 | 0.79 |
|   |   | 0.403 | 0.20 |   |   |
|   |   | 0.596 | 0.13 |   |   |
|   | 2 | 0.039 | 0.22 | 1.13 |   |
|   |   | 0.116 | 0.09 |   |   |
|   |   | 0.135 | 0.09 |   |   |
|   |   | 0.403 | 0.46 |   |   |
|   |   | 0.596 | 0.28 |   |   |
| 5 | 1 | 0.039 | 0.18 | 4.60 | 4.80 |
|   |   | 0.089 | 0.07 |   |   |
|   |   | 0.115 | 0.05 |   |   |
|   |   | 0.133 | 4.20 |   |   |
|   |   | 0.403 | 0.10 |   |   |
|   | 2 | 0.039 | 0.18 | 5.00 |   |
|   |   | 0.089 | 0.09 |   |   |
|   |   | 0.132 | 4.64 |   |   |
|   |   | 0.402 | 0.08 |   |   |
| 6 | 1 | 0.038 | 0.17 | 2.85 | 2.76 |
|   |   | 0.132 | 2.55 |   |   |
|   |   | 0.403 | 0.13 |   |   |
|   | 2 | 0.038 | 0.17 | 2.66 |   |
|   |   | 0.114 | 0.06 |   |   |
|   |   | 0.132 | 2.31 |   |   |
|   |   | 0.402 | 0.13 |   |   |

TABLE 7

One Month Stability Results - 40° C./75% RH

| Lot | Replicate | pH | Assay (mg/mL) |
|---|---|---|---|
| 1 | 1 | 3.14 | 1.01 |
|   | 2 | 3.13 | 1.01 |
|   | Mean (n = 2) | 3.14 | 1.01 |
| 4 | 1 | 3.16 | 1.01 |
|   | 2 | 3.16 | 1.00 |
|   | Mean (n = 2) | 3.16 | 1.00 |

TABLE 8

One Month Related Substances Results - 40° C./75% RH

| Lot | Replicate | Unknown (Identified by RRT) | % Related Substance | Total Related Substances (%) | Mean of Total Related Substances (%) |
|---|---|---|---|---|---|
| 1 | 1 | NR | NR | NR | NR |
|   | 2 | NR | NR | NR |   |

TABLE 8-continued

One Month Related Substances Results - 40° C./75% RH

| Lot | Replicate | Unknown (Identified by RRT) | % Related Substance | Total Related Substances (%) | Mean of Total Related Substances (%) |
|---|---|---|---|---|---|
| 4 | 1 | 0.592 | 0.05 | 0.05 | 0.22 |
|   | 2 | 0.040 | 0.12 | 0.38 |   |
|   |   | 0.115 | 0.06 |   |   |
|   |   | 0.592 | 0.19 |   |   |

TABLE 9

One Month Stability Results - 25° C./60% RH

| Lot | Replicate | pH | Assay (mg/mL) |
|---|---|---|---|
| 1 | 1 | 3.11 | 1.01 |
|   | 2 | 3.16 | 1.01 |
|   | Mean (n = 2) | 3.14 | 1.01 |
| 2 | 1 | 6.33 | No analysis performed |
|   | 2 | 6.41 |   |
|   | Mean (n = 2) | 6.37 |   |
| 3 | 1 | 5.20 | No analysis performed |
|   | 2 | 5.21 |   |
|   | Mean (n = 2) | 5.21 |   |
| 4 | 1 | 3.19 | 1.01 |
|   | 2 | 3.17 | 1.01 |
|   | Mean (n = 2) | 3.18 | 1.01 |
| 5 | 1 | 6.32 | No analysis performed |
|   | 2 | 6.40 |   |
|   | Mean (n = 2) | 6.36 |   |
| 6 | 1 | 5.23 | No analysis performed |
|   | 2 | 5.24 |   |
|   | Mean (n = 2) | 5.24 |   |

TABLE 10

One Month Related Substances Results - 25° C./60% RH

| Lot | Replicate | Unknown (Identified by RRT) | % Related Substances | Total Related Substances (%) | Mean of Total Related Substances (%) |
|---|---|---|---|---|---|
| 1 | 1 | NR | NR | NR | NR |
|   | 2 | NR | NR | NR |   |
| 4 | 1 | NR | NR | NR | NR |
|   | 2 | NR | NR | NR |   |

Three month stability testing was conducted as previously described, including the following measurements:
- pH analysis for all lots at the 25° C./60% RH condition
- pH analysis for lots 1 and 4 at the 40° C./75% RH condition
- Assay and Related Substances analysis for lots 1 and 4 at the 25° C./60% RH and 40° C./75% RH conditions

TABLE 11

Three Month Stability Results - 70° C./75% RH

| Lot | Replicate | Appearance | pH | Assay (mg/mL) |
|---|---|---|---|---|
| 1 | 1 | Clear, colorless solution free of visible particulate matter | 3.70 | 1.00 |
|   | 2 | Clear, colorless solution free of visible particulate matter | 3.70 | 1.00 |
|   |   | Mean (n = 2) | 3.70 | 1.00 |
| 4 | 1 | Clear, colorless solution free of visible particulate matter | 3.74 | 0.96 |

TABLE 11-continued

Three Month Stability Results - 70° C./75% RH

| Lot | Replicate | Appearance | pH | Assay (mg/mL) |
|---|---|---|---|---|
|   | 2 | Clear, colorless solution free of visible particulate matter | 3.77 | 0.94 |
|   |   | Mean (n = 2) | 3.76 | 0.95 |

TABLE 12a

Three Month Related Substances Results - 70° C./75% RH - Lot 1

| Lot | Replicate | Unknown (Identified by RRT) | % Related Substance | Total Related Substances (%) | Mean of Total Related Substances (%) |
|---|---|---|---|---|---|
| 1 | 1 | 0.039 | 0.36 | 1.70 | 1.74 |
|   |   | 0.096 | 0.14 |   |   |
|   |   | 0.136 | 0.05 |   |   |
|   |   | 0.165 | 0.34 |   |   |
|   |   | 0.364 | 0.50 |   |   |
|   |   | 0.384 | 0.06 |   |   |
|   |   | 0.555 | 0.19 |   |   |
|   |   | 1.112 | 0.06 |   |   |
|   | 2 | 0.039 | 0.39 | 1.79 |   |
|   |   | 0.096 | 0.15 |   |   |
|   |   | 0.136 | 0.05 |   |   |
|   |   | 0.165 | 0.41 |   |   |
|   |   | 0.364 | 0.47 |   |   |
|   |   | 0.384 | 0.06 |   |   |
|   |   | 0.555 | 0.18 |   |   |
|   |   | 1.112 | 0.07 |   |   |

TABLE 12b

Three Month Related Substances Results - 70° C./75% RH - Lot 4

| Lot | Replicate | Unknown (Identified by RRT) | % Related Substance | Total Related Substances (%) | Mean of Total Related Substances (%) |
|---|---|---|---|---|---|
| 4 | 1 | 0.039 | 0.78 | 3.44 | 4.34 |
|   |   | 0.095 | 0.38 |   |   |
|   |   | 0.112 | 0.06 |   |   |
|   |   | 0.135 | 0.13 |   |   |
|   |   | 0.155 | 0.06 |   |   |
|   |   | 0.164 | 0.66 |   |   |
|   |   | 0.312 | 0.07 |   |   |
|   |   | 0.363 | 0.76 |   |   |
|   |   | 0.383 | 0.10 |   |   |
|   |   | 0.554 | 0.29 |   |   |
|   |   | 1.111 | 0.14 |   |   |
|   | 2 | 0.039 | 1.16 | 5.23 |   |
|   |   | 0.096 | 0.58 |   |   |
|   |   | 0.112 | 0.11 |   |   |
|   |   | 0.135 | 0.21 |   |   |
|   |   | 0.155 | 0.07 |   |   |
|   |   | 0.164 | 0.96 |   |   |
|   |   | 0.312 | 0.11 |   |   |
|   |   | 0.363 | 1.19 |   |   |
|   |   | 0.383 | 0.14 |   |   |
|   |   | 0.553 | 0.46 |   |   |
|   |   | 1.110 | 0.24 |   |   |

TABLE 13

Three Month Stability Results - 40° C./75% RH

| Lot | Replicate | Appearance | pH | Assay (mg/mL) |
|---|---|---|---|---|
| 1 | 1 | Clear, colorless solution free of visible particulate matter | 3.21 | 1.01 |
|   | 2 | Clear, colorless solution free of visible particulate matter | 3.23 | 1.01 |
|   |   | Mean (n = 2) | 3.22 | 1.01 |
| 4 | 1 | Clear, colorless solution free of visible particulate matter | 3.31 | 1.01 |
|   | 2 | Clear, colorless solution free of visible particulate matter | 3.33 | 1.01 |
|   |   | Mean (n = 2) | 3.32 | 1.01 |

TABLE 14

Three Month Related Substances Results - 40° C./75% RH

| Lot | Replicate | Unknown (Identified by RRT) | % Related Substance | Total Related Substances (%) | Mean of Total Related Substances (%) |
|---|---|---|---|---|---|
| 1 | 1 | 0.039 | 0.06 | 0.23 | 0.17 |
|   |   | 0.364 | 0.06 |  |  |
|   |   | 0.555 | 0.11 |  |  |
|   | 2 | 0.555 | 0.10 | 0.10 |  |
| 4 | 1 | 0.039 | 0.08 | 0.25 | 0.20 |
|   |   | 0.363 | 0.06 |  |  |
|   |   | 0.554 | 0.11 |  |  |
|   | 2 | 0.039 | 0.05 | 0.14 |  |
|   |   | 0.554 | 0.09 |  |  |

TABLE 15

Three Month Stability Results - 25° C./60% RH

| Lot | Replicate | Appearance | pH | Assay (mg/mL) |
|---|---|---|---|---|
| 1 | 1 | Clear, colorless solution free of visible particulate matter | 3.18 | 1.01 |
|   | 2 | Clear, colorless solution free of visible particulate matter | 3.18 | 1.01 |
|   |   | Mean (n = 2) | 3.18 | 1.01 |
| 4 | 1 | Clear, colorless solution free of visible particulate matter | 3.21 | 1.01 |
|   | 2 | Clear, colorless solution free of visible particulate matter | 3.19 | 1.01 |
|   |   | Mean (n = 2) | 3.20 | 1.01 |

TABLE 16

Three Month Related Substances Results - 25° C./60% RH

| Lot | Replicate | Unknown (Identified by RRT) | % Related Substance | Total Related Substances (%) | Mean of Total Related Substances (%) |
|---|---|---|---|---|---|
| 1 | 1 | NR | NR | NR | NR |
|   | 2 | NR | NR | NR |  |
| 4 | 1 | NR | NR | NR | NR |
|   | 2 | NR | NR | NR |  |

Medicament Delivery Devices

The naloxone compositions described herein can be included in any suitable medicament delivery device. For example, in some embodiments, a medicament delivery device configured for self-administration (or administration by an untrained user, such a person accompanying the patient) can include any of the naloxone compositions described herein. Such medicament delivery devices can include, for example, an auto-injector, an intranasal delivery device, a pre-filled syringe, an inhaler or the like. In this manner, the medicament delivery device (including the naloxone composition) can be used by the patient (or an untrained user) in any setting (e.g., the patient's home, in a public venue or the like).

In some embodiments, a medicament delivery device can be configured to automatically deliver any of the naloxone compositions described herein. Similarly stated, in some embodiments, a medicament delivery device, after being actuated by the user, can automatically produce (i.e., produce without any further human intervention) a force to deliver the naloxone composition. In this manner, the force with which the naloxone composition is delivered is within a desired range, and is repeatable between different devices, users or the like.

One example of such a medicament delivery device is provided in FIG. 1, which is a schematic illustration of a medicament delivery device 1000 according to an embodiment. The medicament delivery device 1000 includes a housing 1110, a medicament container 1400 and an energy storage member 1570. The medicament container 1400 is disposed within the housing 1110, and contains (i.e., is filled or partially filled with) a naloxone composition 1420. The energy storage member 1570 is disposed within the housing 1110, and is configured to produce a force F1 to deliver the naloxone composition 1420 (e.g., from the medicament container 1400 to a body).

The naloxone composition 1420 can be any of the naloxone compositions described herein. In particular, the naloxone composition 1420 can include an effective amount of naloxone or salts thereof, a tonicity-adjusting agent, and a pH adjusting agent. The naloxone composition 1420 can be formulated such that the osmolality of the naloxone composition 1420 ranges from about 250-350 mOsm and the pH ranges from about 3-5.

In some embodiments, the naloxone composition 1420 can include any suitable concentration of 4,5-epoxy-3,14-dihydroxy-17-(2-propenyl) morphinan-6-one. In some embodiments, for example, the naloxone composition 1420 has a concentration of 4,5-epoxy-3,14-dihydroxy-17-(2-propenyl)morphinan-6-one between approximately 0.01 mg/mL and approximately 10 mg/mL. In other embodiments, the naloxone composition 1420 has a concentration of 4,5-epoxy-3,14-dihydroxy-17-(2-propenyl)morphinan-6-one between approximately 0.05 mg/mL and approximately 2 mg/mL.

The tonicity-adjusting agent can be any of the tonicity-adjusting agents described herein, and can be included within the naloxone composition 1420 in any suitable amount and/or concentration. For example, in some embodiments, the tonicity-adjusting agent includes at least one of dextrose, glycerin, mannitol, potassium chloride or sodium chloride. In other embodiments, the tonicity-adjusting agent includes sodium chloride in an amount such that a concentration of sodium chloride is between approximately 0.1 mg/mL and approximately 20 mg/mL.

The pH adjusting agent can be any of the pH adjusting agents described herein, and can be included within the naloxone composition 1420 in any suitable amount and/or concentration. For example, in some embodiments, the pH adjusting agent includes at least one of hydrochloric acid, citric acid, citrate salts, acetic acid, acetate salts, phosphoric acid or phosphate salts. In other embodiments, the pH adjusting agent includes a dilute hydrochloric acid.

The medicament container 1400 can be any container suitable for storing the naloxone composition 1420. In some embodiments, the medicament container 1400 can be, for example, a pre-filled syringe, a pre-filled cartridge, a vial, an ampule or the like. In other embodiments, the medicament container 1400 can be a container having a flexible wall, such as, for example, a bladder.

The energy storage member 1570 can be any suitable device or mechanism that, when actuated, produces a force F1 to deliver the naloxone composition 1420. Similarly stated, the energy storage member 1570 can be any suitable device or mechanism that produces the force F1 such that the naloxone composition 1420 is conveyed from the medicament container 1400 into a body of a patient. The naloxone composition 1420 can be conveyed into a body via any suitable mechanism, such as, for example, by injection, intranasally, via inhalation or the like. By employing the energy storage member 1570 to produce the force F1, rather than relying on a user to manually produce the delivery force, the naloxone composition 1420 can be delivered into the body at the desired pressure and/or flow rate, and with the desired characteristics. Moreover, this arrangement reduces the likelihood of partial delivery (e.g., that may result if the user is interrupted or otherwise rendered unable to complete the delivery).

In some embodiments, the energy storage member 1570 can be a mechanical energy storage member, such as a spring, a device containing compressed gas, a device containing a vapor pressure-based propellant or the like. In other embodiments, the energy storage member 1570 can be an electrical energy storage member, such as a battery, a capacitor, a magnetic energy storage member or the like. In yet other embodiments, the energy storage member 1570 can be a chemical energy storage member, such as a container containing two substances that, when mixed, react to produce energy.

As shown in FIG. 1, the energy storage member 1570 can be in any position and/or orientation relative to the medicament container 1400. In some embodiments, for example, the energy storage member 1570 can be positioned within the housing 1110 spaced apart from the medicament container 1400. Moreover, in some embodiments, the energy storage member 1570 can be positioned such that a longitudinal axis of the energy storage member 1570 is offset from the medicament container 1400. In other embodiments, the energy storage member 1570 can substantially surround the medicament container 1400.

Moreover, the energy storage member 1570 can be operably coupled to the medicament container 1400 and/or the naloxone composition 1420 therein such that the force F1 delivers the naloxone composition 1420. In some embodiments, for example, the force F1 can be transmitted to the naloxone composition 1420 via a piston or plunger (not shown in FIG. 1). In other embodiments, the force F1 can be transmitted to the naloxone composition 1420 via a hydraulic or pneumatic coupling. In yet other embodiments, the force F1 can be transmitted to the naloxone composition 1420 electrically. In still other embodiments, the force F1 can be transmitted to the naloxone composition 1420 via a combination of any of the above.

Figure 2:
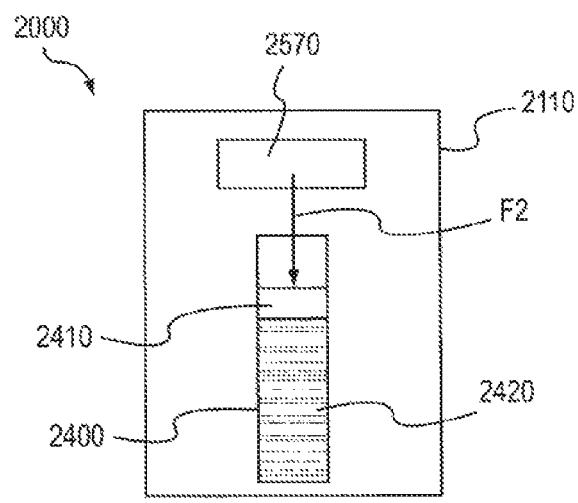
FIG. 2 is a schematic illustration of a medicament delivery device according to an embodiment.

In some embodiments, a medicament container can include an elastomeric member, such that the force produced by an energy storage member is transferred to the naloxone composition by the elastomeric member. For example, FIG. 2 is a schematic illustration of a medicament delivery device 2000 according to an embodiment. The medicament delivery device 2000 includes a housing 2110, a medicament container 2400, an elastomeric member 2410 and an energy storage member 2570. The medicament container 2400 is disposed within the housing 2110, and contains (i.e., is filled or partially filled with) a naloxone composition 2420. The naloxone composition 2420 can be any of the naloxone compositions described herein. The energy storage member 2570 is disposed within the housing 2110, and is configured to produce a force F2 to deliver the naloxone composition 2420, as described herein.

The elastomeric member 2410 is disposed within the medicament container 2400 to seal an end portion of the medicament container 2400. The elastomeric member 2410 can be disposed within the medicament container 2400 during the fill process, and can form a substantially fluid-tight seal to prevent leakage of the naloxone composition 2420 from the medicament container 2400. Moreover, the elastomeric member 2410 is operatively coupled to the energy storage member 2570 such that, in use the force F2 acts upon the elastomeric member 2410 to deliver the naloxone composition 2420 from the medicament container 2400.

The elastomeric member 2410 is formulated to be compatible with the naloxone composition 2420. Similarly stated, the elastomeric member 2410 is formulated to minimize any reduction in the efficacy of the naloxone composition 2420 that may result from contact (either direct or indirect) between the elastomeric member 2410 and the naloxone composition 2420. For example, in some embodiments, the elastomeric member 2410 can be formulated to minimize any leaching or out-gassing of compositions that may have an undesired effect on the naloxone composition 2420. In other embodiments, the elastomeric member 2410 can be formulated to maintain its chemical stability, flexibility and/or sealing properties when in contact (either direct or indirect) with naloxone over a long period of time (e.g., for up to six months, one year, two years, five years or longer).

In some embodiments, the elastomeric member 2410 can be formulated to include a polymer and a curing agent. In such embodiments, the polymer can include at least one of bromobutyl or chlorobutyl. In such embodiments, the curing agent can include at least one of sulfur, zinc or magnesium.

In some embodiments, the elastomeric member 2410 can be constructed from multiple different materials. For example, in some embodiments, at least a portion of the elastomeric member 2410 can be coated. Such coatings can include, for example, polydimethylsiloxane. In some embodiments, at least a portion of the elastomeric member 2410 can be coated with polydimethylsiloxane in an amount of between approximately 0.02 mg/cm$^2$ and approximately 0.80 mg/cm$^2$.

Figure 3:
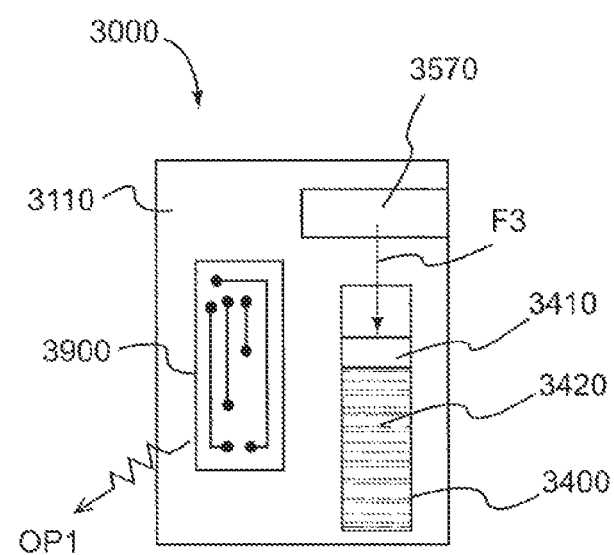
FIG. 3 is a schematic illustration of a medicament delivery device according to an embodiment.

A medicament delivery device configured for delivery of a naloxone composition can include an electronic circuit system that produces an output. Such output can include, for example, any output to assist the user and/or patient in administering the dose of the naloxone composition. For example, FIG. 3 is a schematic illustration of a medicament delivery device 3000 according to an embodiment. The medicament delivery device 3000 includes a housing 3110, a medicament container 3400, an elastomeric member 3410, an energy storage member 3570 and an electronic circuit system 3900. The medicament container 3400 is disposed within the housing 3110, and contains (i.e., is filled or partially filled with) a naloxone composition 3420. The naloxone composition 3420 can be any of the naloxone compositions described herein. For example, in some embodiments, the naloxone composition 3420 can include an effective amount of naloxone or salts thereof, a tonicity-adjusting agent, and a pH adjusting agent. The naloxone composition can be formulated such that the osmolality of the naloxone composition ranges from about 250-350 mOsm and the pH ranges from about 3-5.

The energy storage member 3570 is disposed within the housing 3110, and is configured to produce a force F2 to deliver the naloxone composition 3420, as described herein. The elastomeric member 3410 is disposed within the medicament container 3400 to seal an end portion of the medicament container 3400. Moreover, the elastomeric member 3410 is operatively coupled to the energy storage member 3570 such that, in use the force F2 acts upon the elastomeric member 3410 to deliver the naloxone composition 3420 from the medicament container 3400.

The electronic circuit system 3900 is configured to produce an output OP1 when the electronic circuit system 3900 is actuated. The output can be, for example, an audible or visual output related to the naloxone composition (e.g., an indication of the expiration date, the symptoms requirement treatment with naloxone or the like), the use of the medicament delivery device, and/or post-administration procedures (e.g., a prompt to call 911, instructions for the disposal of the device or the like).

For example, in some embodiments, the electronic output OP1 can be associated with an instruction for using the medicament delivery device 3000. In other embodiments, the electronic output OP1 can be a post-use instruction, such as, for example, a recorded message notifying the user that the delivery of the naloxone composition 3420 is complete, instructing the user on post-use disposal of the medicament delivery device 3000 (e.g., post-use safety procedures), instructing the user to seek post-use medical treatment, and/or the like. In yet other embodiments, the electronic output OP1 can be associated with the patient's compliance in using medicament delivery device 3000.

The electronic output OP1 can be, for example, a visual output such as, for example, a text message to display on a screen (not shown), and/or an LED. In some embodiments, the electronic output OP1 can be an audio output, such as, for example, recorded speech, a series of tones, and/or the like. In other embodiments, the electronic output OP1 can be a wireless signal configured to be received by a remote device.

As described in more detail herein, the electronic circuit system 3900 can include any suitable electronic components operatively coupled to produce and/or output the electronic output OP1 and/or to perform the functions described herein. The electronic circuit system 3900 can be similar to the electronic circuit systems described in U.S. Pat. No. 7,731,686, entitled "Devices, Systems and Methods for Medicament Delivery," filed Jan. 9, 2007, which is incorporated herein by reference in its entirety.

The electronic circuit system 3900 can be actuated to produce the electronic output OP1 in any suitable manner. For example, in some embodiments, the electronic circuit system 3900 can be associated with an actuation of the medicament delivery device 3000. Said another way, the electronic circuit system 3900 can be configured to output the electronic output OP1 in response to actuation of the medicament delivery device 3000. In other embodiments, the electronic circuit system 3900 can be actuated manually by a switch (not shown in FIG. 3). Such a switch can be actuated (i.e., to actuated the electronic circuit system 3900) by a push button, by removing the medicament delivery device 3000 from a case or cover (not shown in FIG. 3), by receiving a signal from a remote electronic device, and/or any other suitable mechanism. In yet other embodiments, the electronic circuit system 3900 can be actuated by receiving input from the user via a voice prompt system.

The electronic circuit system 3900 can be coupled to and/or disposed within the housing 3110 in any suitable arrangement. For example, in some embodiments, the electronic circuit system 3900 can be coupled to an exterior or outer surface of the housing 3110. In other embodiments, at least a portion of the electronic circuit system 3900 can be disposed within the housing 3110. Moreover, in some embodiments, a portion of the electronic circuit system 1900 is disposed within the housing 3110 such that the portion of the electronic circuit system 3900 is fluidically and/or physically isolated from the medicament container 3400.

Figure 4:
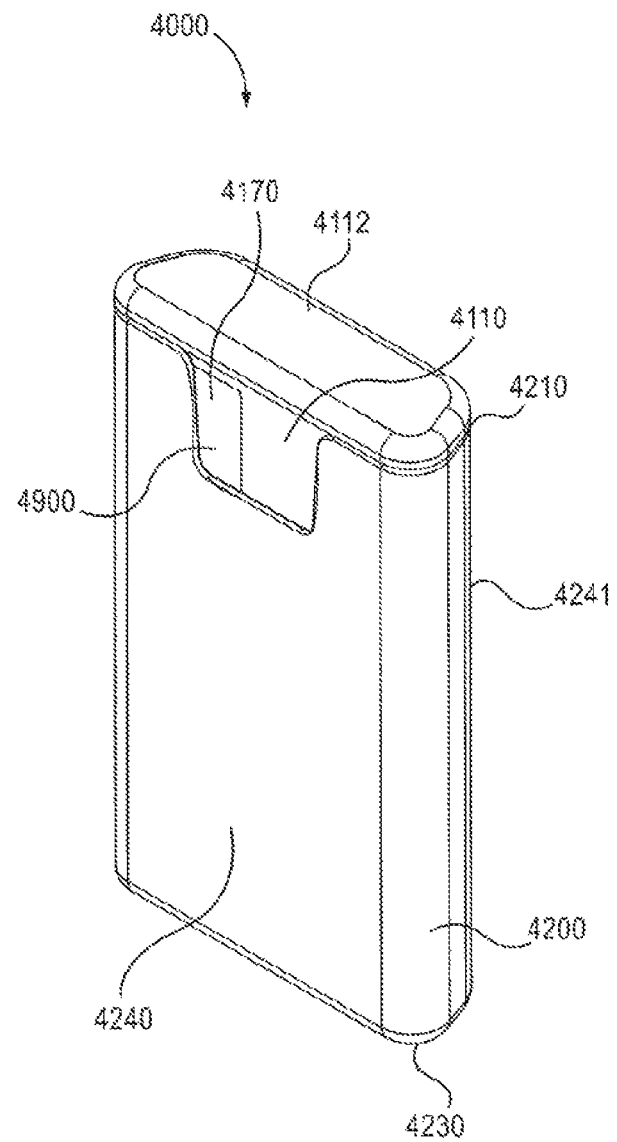
FIGS. 4 and 5 are perspective views of a medical injector according to an embodiment, in a first configuration.
Figure 5:
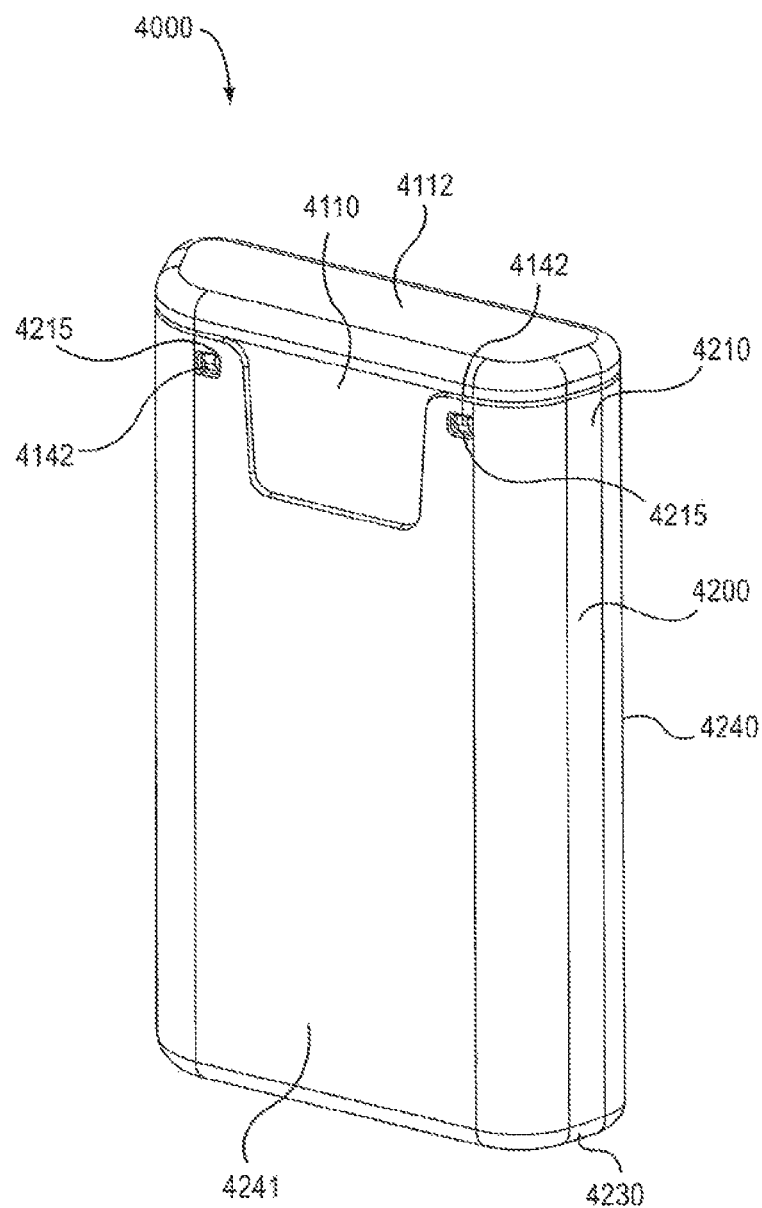
Figure 6:
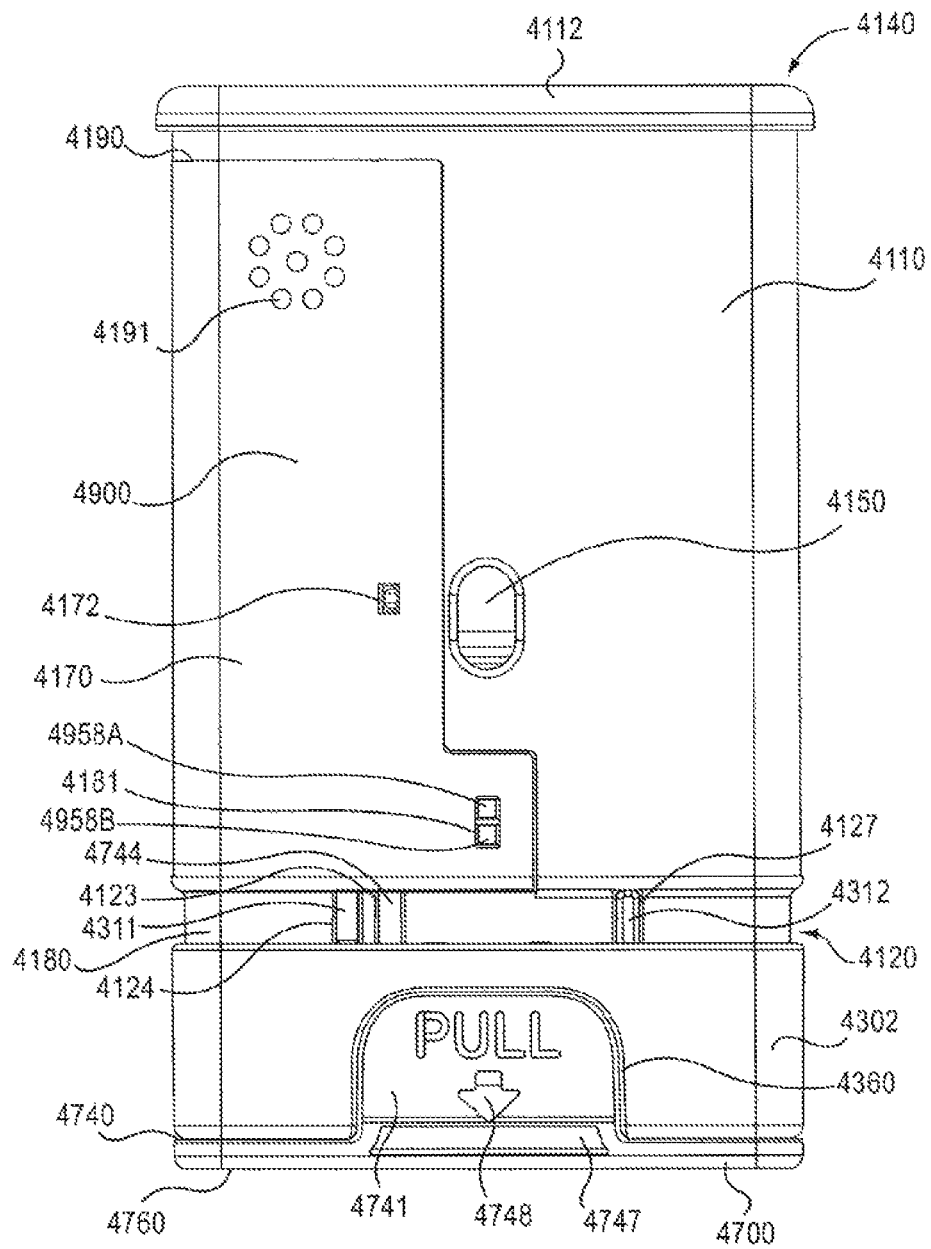
FIG. 6 is a front view of the medical injector illustrated in FIG. 4 with the cover removed.
Figure 29:
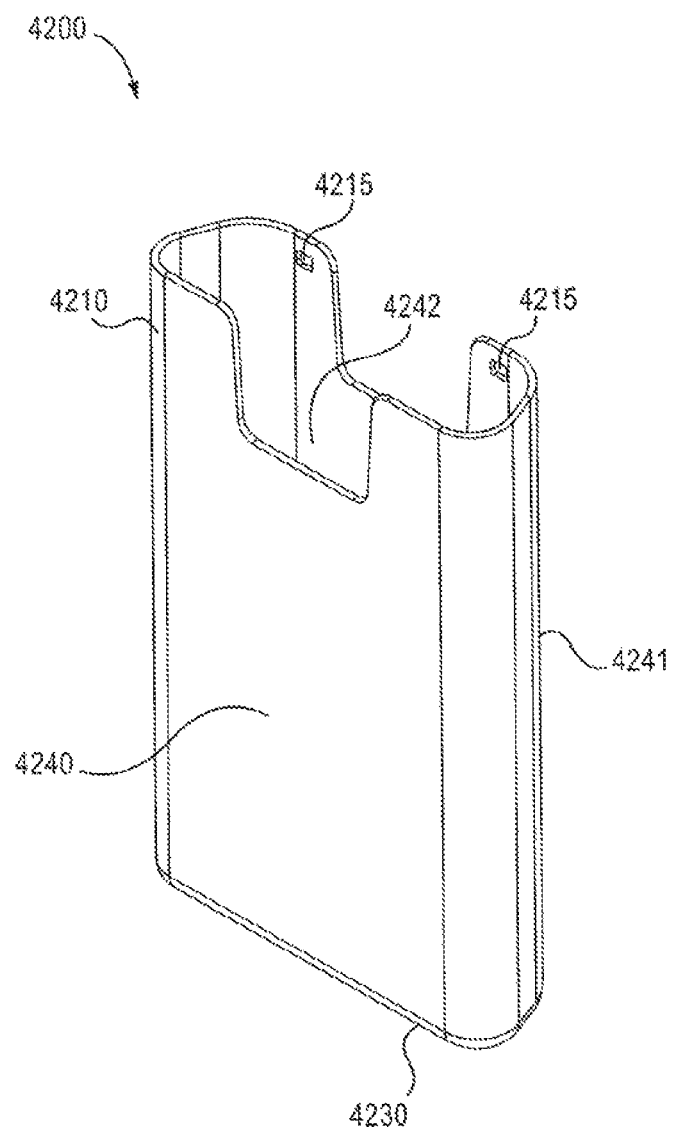
FIGS. 29 and 30 are perspective views of a cover of the medical injector illustrated in FIG. 4.
Figure 30:
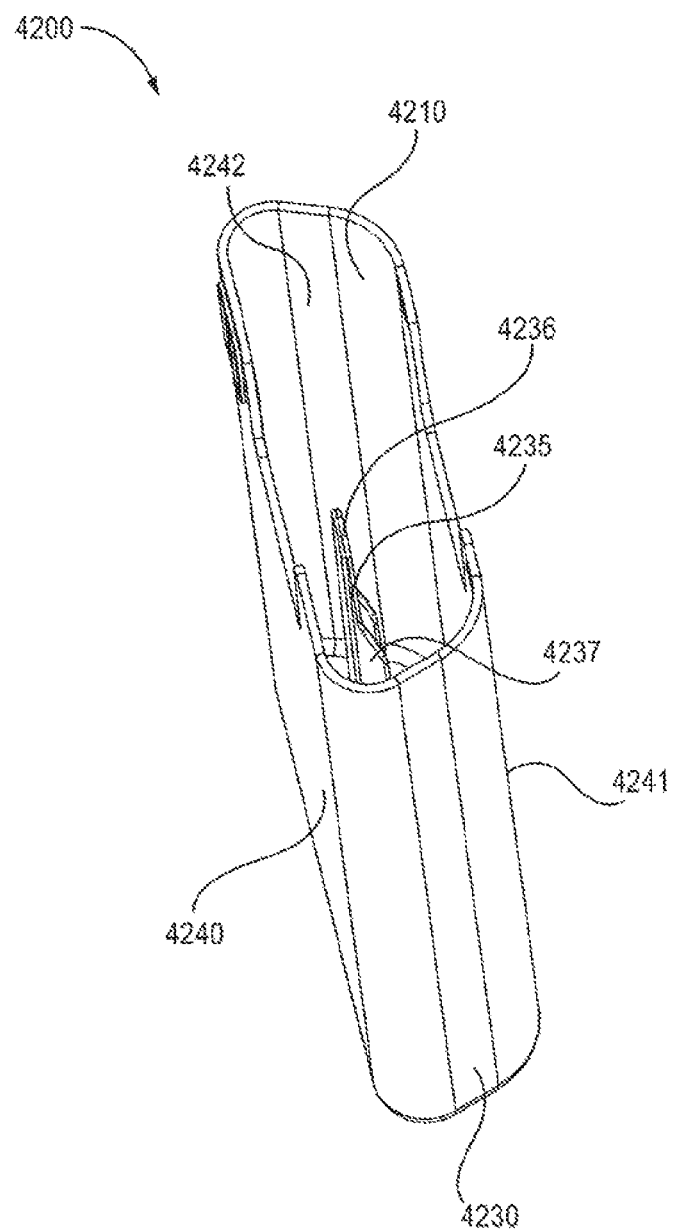
Figure 31:
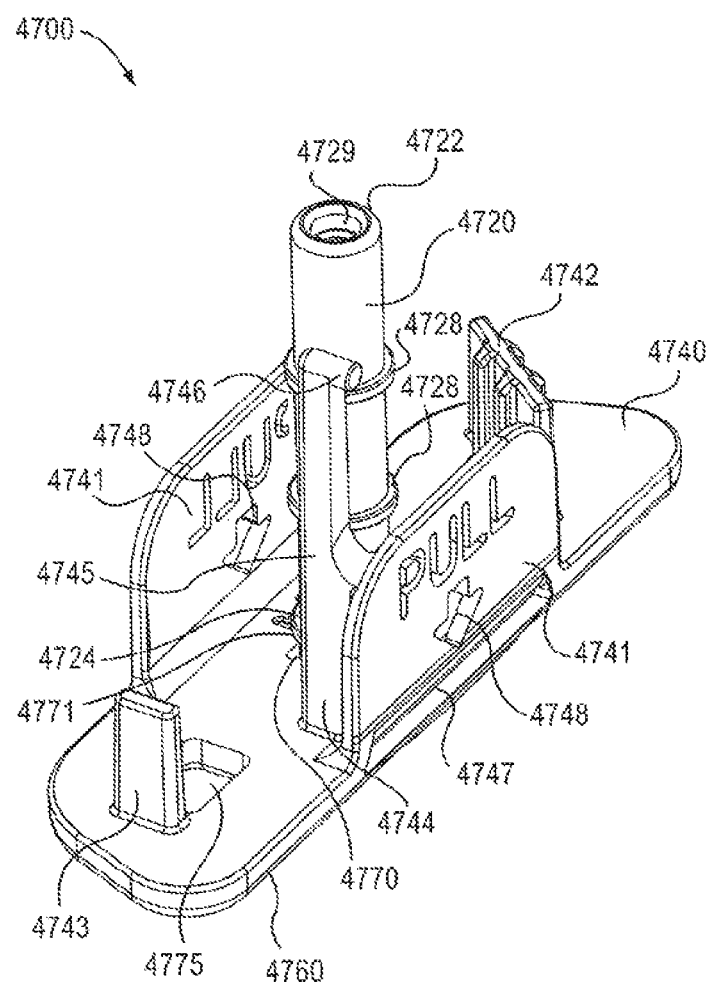
FIG. 31 is a perspective view of a safety lock of the medical injector illustrated in FIG. 4.
Figure 32:
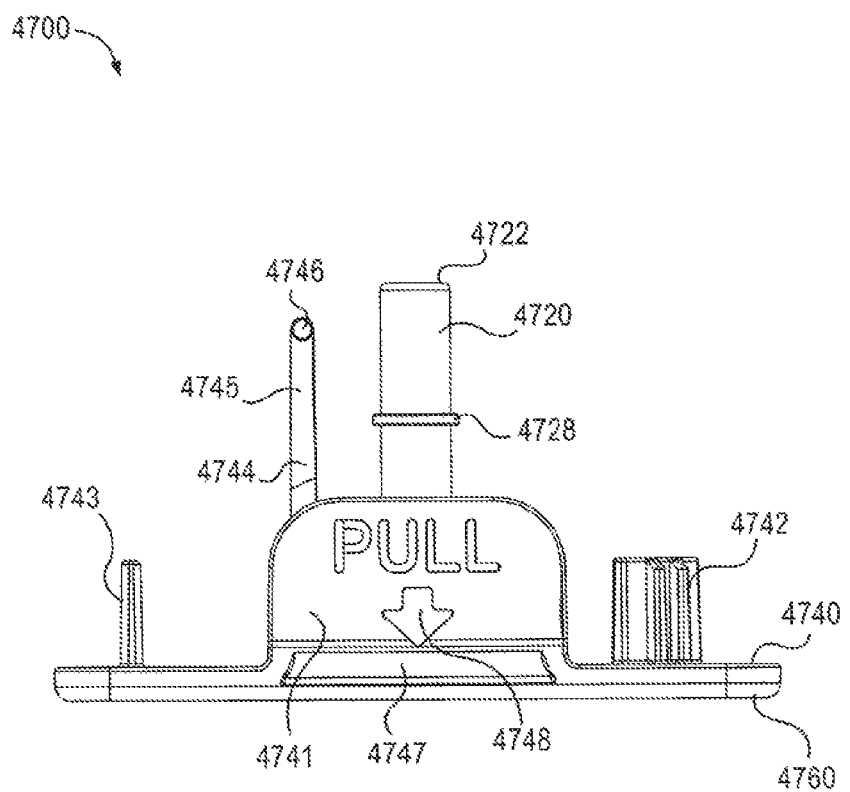
FIG. 32 is a front view of the safety lock of the medical injector illustrated in FIG. 31.

The medicament delivery device 3000 can be any suitable device for automatically delivering any of the naloxone compositions described herein. In some embodiments, the medicament delivery device can be a medical injector configured to automatically deliver a naloxone composition. For example, FIGS. 4-42 show a medical injector 4000, according to an embodiment. FIGS. 4-5 are perspective views of the medical injector 4000 in a first configuration (i.e., prior to use). The medical injector 4000 includes a housing 4110, a delivery mechanism 4500 (see e.g., FIGS. 13-14), a medicament container 4400 containing a naloxone composition 4420 (see e.g., FIG. 16), an electronic circuit system 4900 (see e.g., FIGS. 18-28), a cover 4200 (see e.g., FIGS. 29-30), a safety lock 4700 (see e.g., FIGS. 31-34) and a system actuator assembly 4300 (see e.g., FIGS. 13, 15, 35 and 36). A discussion of the components of the medical injector 4000 will be followed by a discussion of the operation of the medical injector 4000.

As shown in FIGS. 6-12, the housing 4110 has a proximal end portion 4140 and a distal end portion 4120. The housing 4110 defines a first status indicator aperture 4150 and a second status indicator aperture 4151. The first status indicator aperture 4150 defined by the housing 4110 is located on a first side of the housing 4110, and the second status indicator aperture 4151 of the housing 4110 is located on a second side of the housing 4110. The status indicator apertures 4150, 4151 can allow a patient to monitor the status and/or contents of the medicament container 4400 contained within the housing 4110. For example, by visually inspecting the status indicator apertures 4150, 4151, a patient can determine whether the medicament container 4400 contains a medicament and/or whether a medicament has been dispensed.

Figure 10:
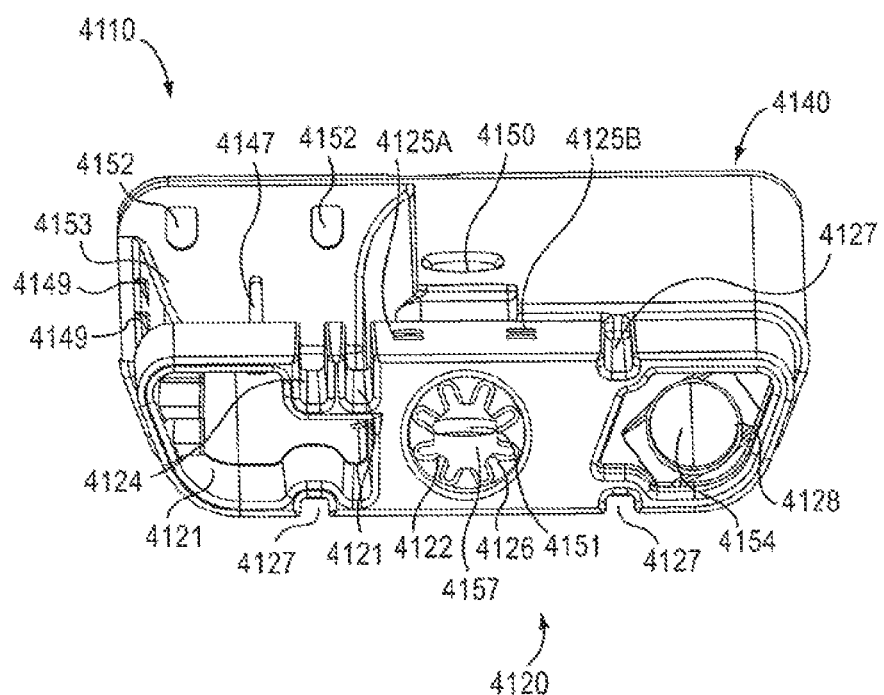
FIG. 10 is a bottom perspective view of a housing of the medical injector illustrated in FIG. 4.
Figure 11:
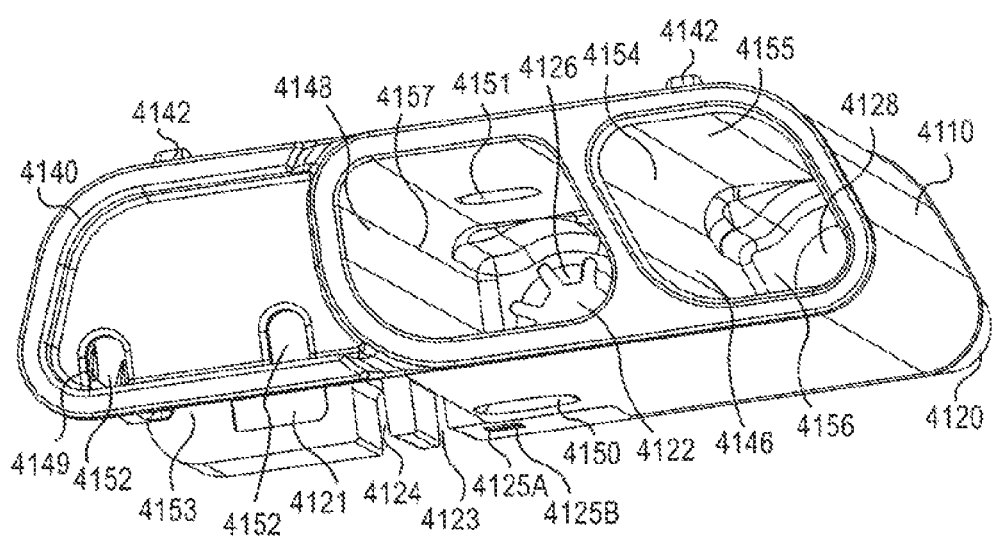
FIG. 11 is a top perspective view of a housing of the medical injector illustrated in FIG. 4.
Figure 13:
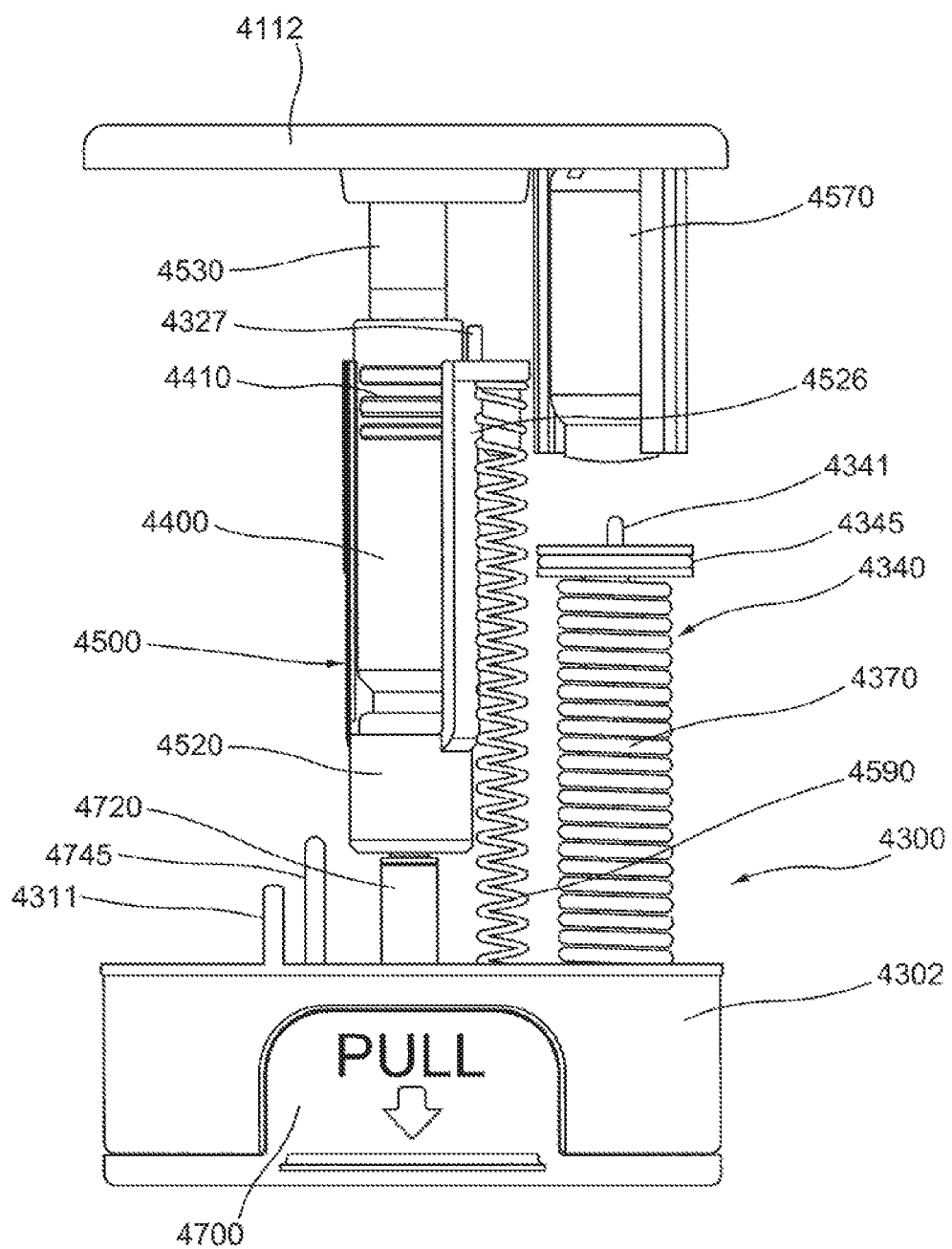
FIGS. 13 and 14 are a front views of a medicament delivery mechanism of the medical injector illustrated in FIG. 4.
Figure 14:
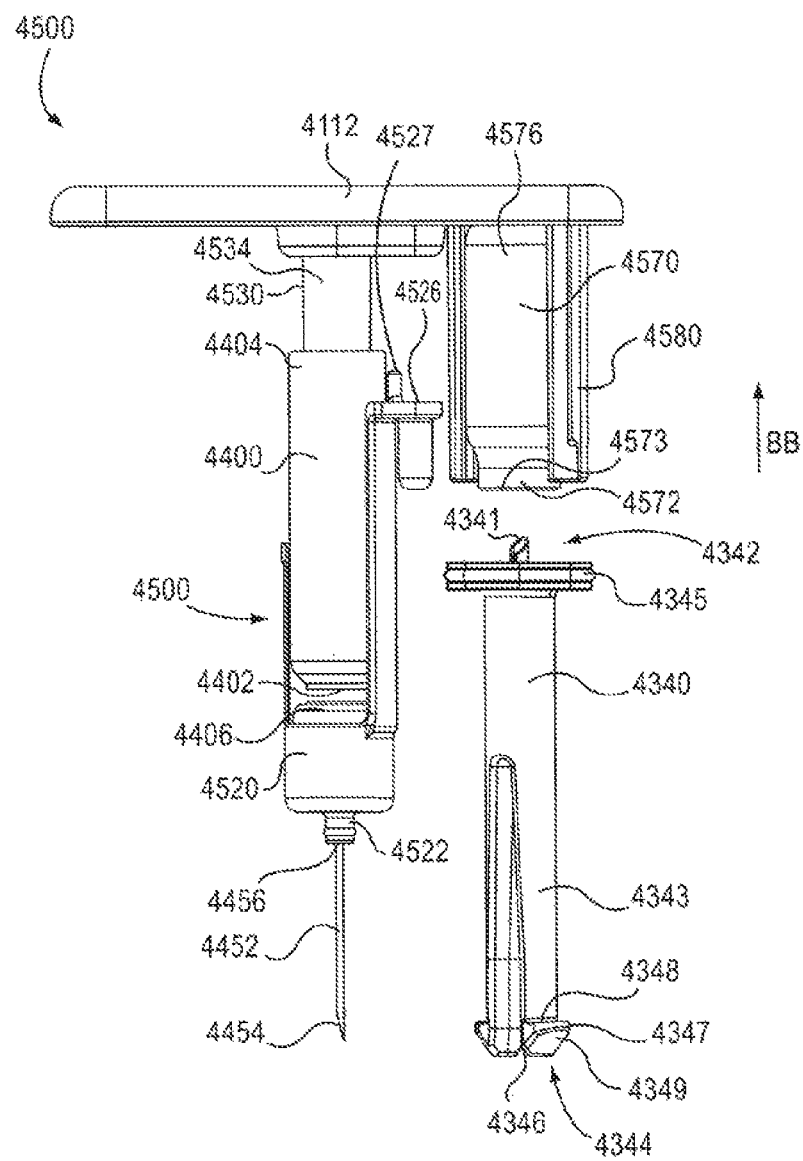

As shown in FIGS. 10 and 11, the housing 4110 defines a gas cavity 4154, a medicament cavity 4157 and an electronic circuit system cavity 4153. The gas cavity 4154 has a proximal end portion 4155 and a distal end portion 4156. The gas cavity 4154 is configured to receive the gas container 4570 and a portion of the system actuator assembly 4300 (e.g., the release member 4340 and the spring 4370, as shown in FIGS. 13 and 14) as described in further detail herein. The proximal end portion 4155 of the gas cavity 4154 is configured to receive the gas container retention member 4580 of the proximal cap 4112 of the housing 4110, as described in further detail herein. The gas cavity 4154 is in fluid communication with the medicament cavity 4157 via a gas passageway 4144 (see e.g., FIG. 12), as described in further detail herein, and the gas cavity 4154 is in fluid communication with a region outside the housing 4110 via a safety lock aperture 4128 (see e.g., FIGS. 10 and 11).

The medicament cavity 4157 is configured to receive the medicament container 4400 and a portion of the delivery mechanism 4500. In particular, the carrier 4520 and the moveable member 4530 of the medicament delivery mechanism 4500 are movably disposed in the medicament cavity 4157. The medicament cavity 4157 is in fluid communication with a region outside the housing 4110 via a needle aperture 4122 (see e.g., FIGS. 10 and 11).

The electronic circuit system cavity 4153 is configured to receive the electronic circuit system 4900. The housing 4110 has protrusions 4149 (see e.g., FIG. 9) configured to stabilize the electronic circuit system 4900 when the electronic circuit system 4900 is disposed within the electronic circuit system cavity 4153. The housing 4110 also defines connection apertures 4152 configured to receive connection protrusions 4171 of the electronic circuit system 4900, and aperture 4145 (see e.g., FIG. 7) configured to receive a portion of a protrusion 4174 of the electronic circuit system 4900. In this manner, the electronic circuit system 4900 can be coupled to the housing 4110 within the electronic circuit system cavity 4153. In other embodiments, the electronic circuit system 4900 can be coupled within the electronic circuit system cavity 4153 by other suitable means such as an adhesive, a clip, a label and/or the like.

The electronic circuit system cavity 4153 is fluidically and/or physically isolated from the gas cavity 4154 and/or the medicament cavity 4157 by a sidewall 4148. The sidewall 4148 can be any suitable structure to isolate the electronic circuit system cavity 4153 within the housing 4110 from the gas cavity 4154 and/or the medicament cavity 4157 within the housing 4110. Similarly, the gas cavity 4154 and the medicament cavity 4157 are separated by a sidewall 4146. In some embodiments, sidewall 4146 can be similar to the sidewall 4148, which isolates the gas cavity 4154 and the medicament cavity 4157 from the electronic circuit system cavity 4153. In other embodiments the gas cavity 4154 can be fluidically and/or physically isolated from the medicament cavity 4157.

Figure 7:
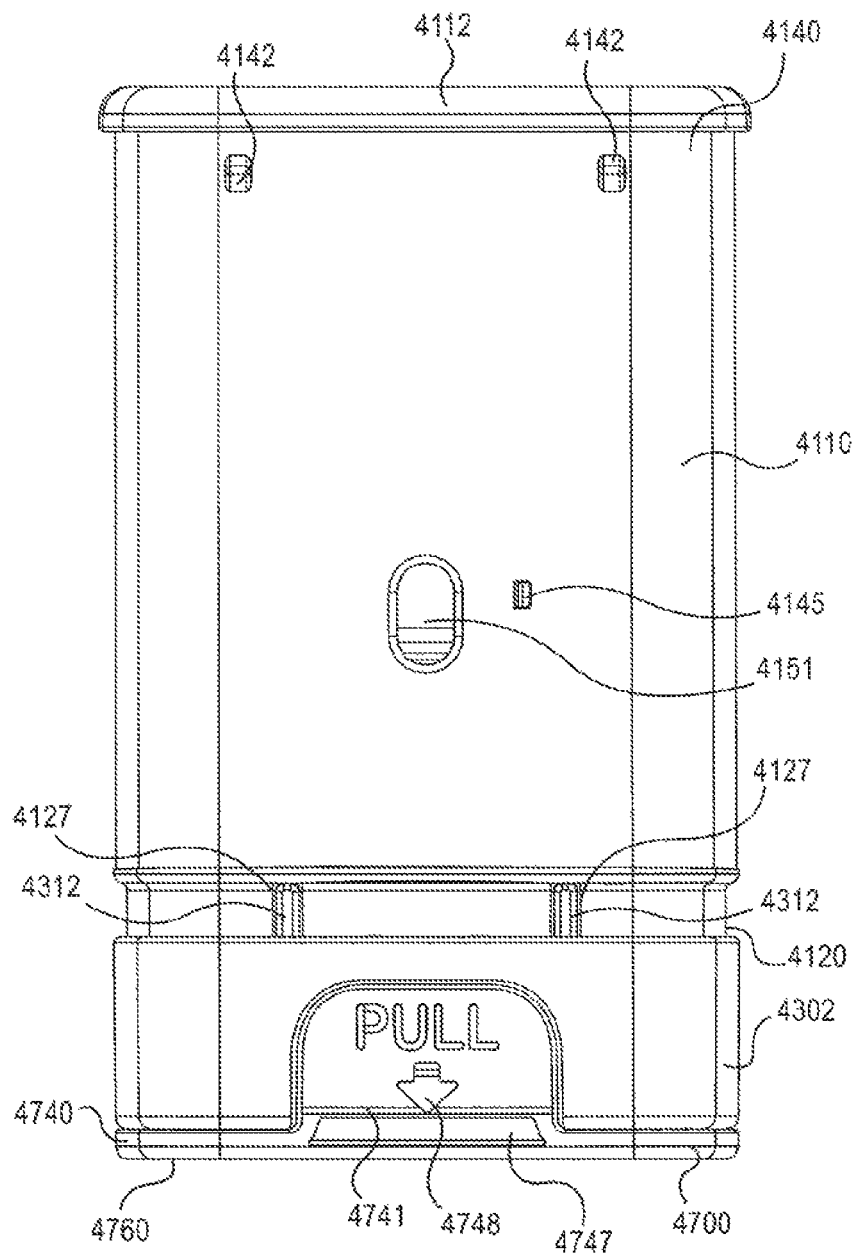
FIG. 7 is a back view of the medical injector illustrated in FIG. 4 with the cover removed.

The proximal end portion 4140 of the housing 4110 includes a proximal cap 4112, a speaker protrusion 4147 (see e.g., FIGS. 9 and 10), and cover retention protrusions 4142 (see e.g., FIGS. 5 and 7). The speaker protrusion 4147 is configured to maintain a position of an audio output device 4956 of the electronic circuit system 4900 relative to the housing 4110 when the electronic circuit system 4900 is attached to the housing 4110, as described herein. Cover retention protrusions 4142 are configured to be received within corresponding openings 4215 on the cover 4200. In this manner, as described in more detail herein, the cover 4200 can be removably coupled to and disposed about at least a portion of the housing 4110.

Figure 12:
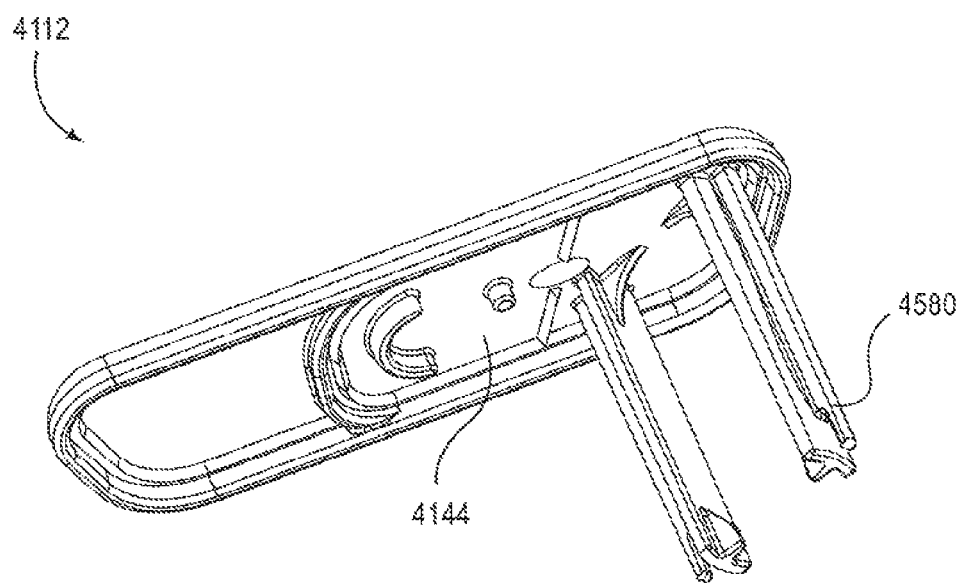
FIG. 12 is a perspective view of a proximal cap of the medical injector illustrated in FIG. 4.

As shown in FIG. 12, the proximal cap 4112 includes a gas container retention member 4580 and defines a gas passageway 4144. The gas container retention member 4580 is configured to receive and/or retain a gas container 4570 that can contain a pressurized gas. The gas passageway 4144 is configured to allow for the passage of gas contained in the gas container 4570 from the gas cavity 4154 to the medicament cavity 4157, as further described herein. Said another way, the gas passageway 4144 places the gas cavity 4154 in fluid communication with the medicament cavity 4157.

Figure 8:
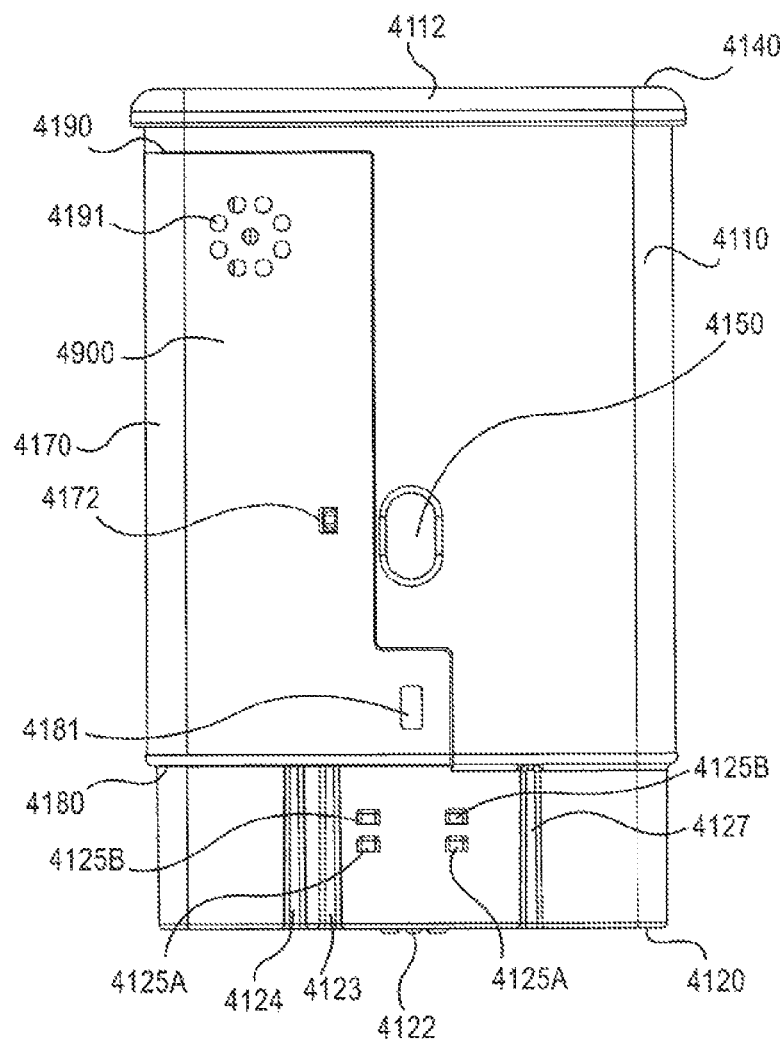
FIG. 8 is a front view of a portion of the medical injector illustrated in FIG. 4.
Figure 9:
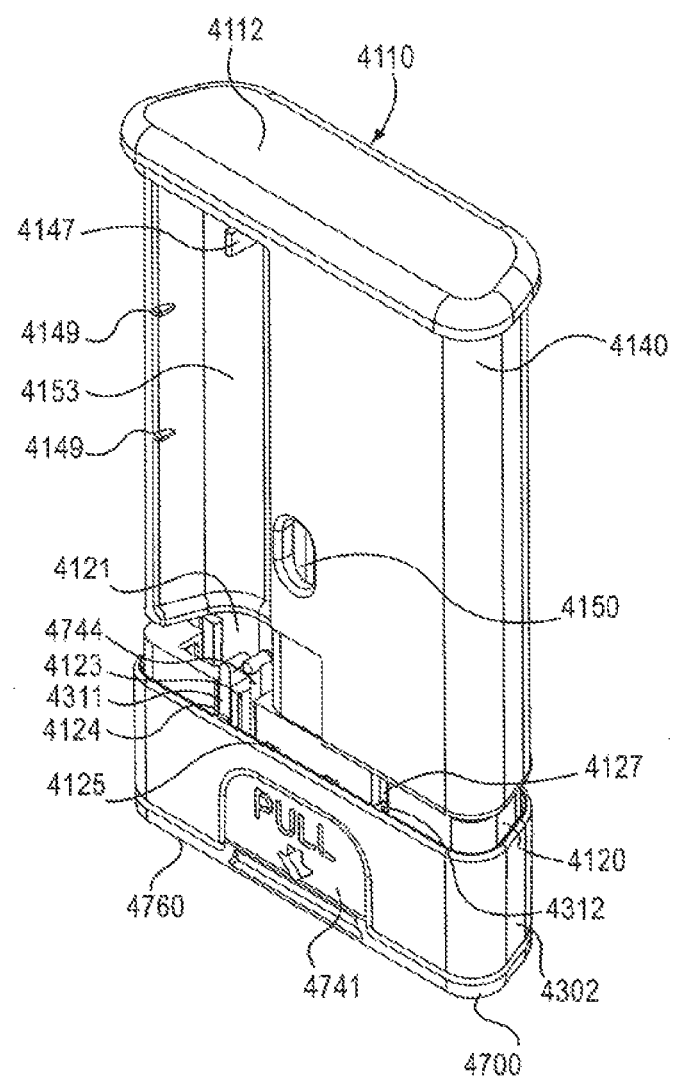
FIG. 9 is a perspective view of a portion of the medical injector illustrated in FIG. 4.

As shown in FIGS. 8 and 10, the distal end portion 4120 of the housing 4110 defines a battery isolation protrusion aperture 4121, a needle aperture 4122, a safety lock actuator groove 4123, a safety lock aperture 4128, a base actuator groove 4124, base retention recesses 4125A, 4125B, and base rail grooves 4127. The battery isolation protrusion aperture 4121 is configured to receive the battery isolation protrusion 4235 of the cover 4200 (see e.g., FIG. 30), as described in further detail herein.

The needle aperture 4122 is configured to allow the needle 4452 (see e.g., FIGS. 13, 39 and 40) to exit the housing 4110 when the medical injector 4000 is actuated. The portion of the sidewall of the housing 4110 that defines the needle aperture 4122 includes multiple sheath retention protrusions 4126. In some embodiments, the sheath retention protrusions can interact with a plurality of ribs 4728 of the needle sheath 4720 (see e.g. FIG. 34) to maintain a position of the needle sheath 4720 relative to the safety lock 4700 when the safety lock 4700 is coupled to the housing 4110 and/or when the safety lock 4700 is being removed from the housing 4110.

The safety lock actuator groove 4123 is configured to receive an actuator 4744 of the safety lock 4700. As described in more detail herein, the actuator 4744 is configured to engage and/or activate the electronic circuit system 4900 when the safety lock 4700 is moved with respect to the housing 4110. The safety lock aperture 4128 is configured to receive a safety lock protrusion 4742 (see e.g., FIGS. 30 and 31). As described in more detail below, when the medical injector is in the first configuration (i.e., when the safety lock 4700 is in place prior to use), the safety lock protrusion 4742 is disposed within an opening 4346 between extensions 4343 of a release member 4340 (see e.g., FIGS. 14 and 15) such that activation of the medical injector 4000 is prevented. The safety lock 4700, its components and functions are further described herein.

The distal base retention recesses 4125A are configured to receive the base connection knobs 4358 of the actuator 4302 (also referred to herein as "base 4302," see e.g., FIG. 35) when the base 4302 is in a first position relative to the housing 4110. The proximal base retention recesses 4125B are configured to receive the base connection knobs 4358 of the base 4302 when the base 4302 is in a second position relative to the housing 4110. The base retention recesses 4125A, 4125B have a tapered proximal sidewall and a non-tapered distal sidewall. This allows the base retention recesses 4125A, 4125B to receive the base connection knobs 4358 such that the base 4302 can move proximally relative to the housing 4110, but cannot move distally relative to the housing 4110. Said another way, the distal base retention recesses 4125A are configured to prevent the base 4302 from moving distally when the base 4302 is in a first position and the proximal base retention recesses 4125B are configured to prevent the base 4302 from moving distally when the base 4302 is in a second position. Similarly stated, the proximal base retention recesses 4125B and the base connection knobs 4358 cooperatively prevent "kickback" after the medical injector 4000 is actuated.

The base actuator groove 4124 is configured to receive an actuator 4311 of the base 4302. As described in more detail herein, the actuator 4311 of the base 4302 is configured to engage the electronic circuit system 4900 when the base 4302 is moved with respect to the housing 4110. The base rail grooves 4127 are configured to receive the guide members 4312 of the base 4302. The guide members 4312 of the base 4302 and the base rail grooves 4127 of the housing 4110 engage each other in a way that allows the guide members 4312 of the base 4302 to slide in a proximal and/or distal direction within the base rail grooves 4127 while limiting lateral movement of the guide members 4312. This arrangement allows the base 4302 to move in a proximal and/or distal direction with respect to the housing 4110 but prevents the base 4302 from moving in a lateral direction with respect to the housing 4110.

FIGS. 13-16 show the medicament container 4400, the system actuator assembly 4300 and the medicament delivery mechanism 4500 of the medical injector 4000. The medical injector 4000 is similar to the auto-injectors described in U.S. Pat. No. 7,648,482, entitled "Devices, Systems and Methods for Medicament Delivery," filed Nov. 21, 2006, which is incorporated herein by reference in its entirety.

Figure 16:
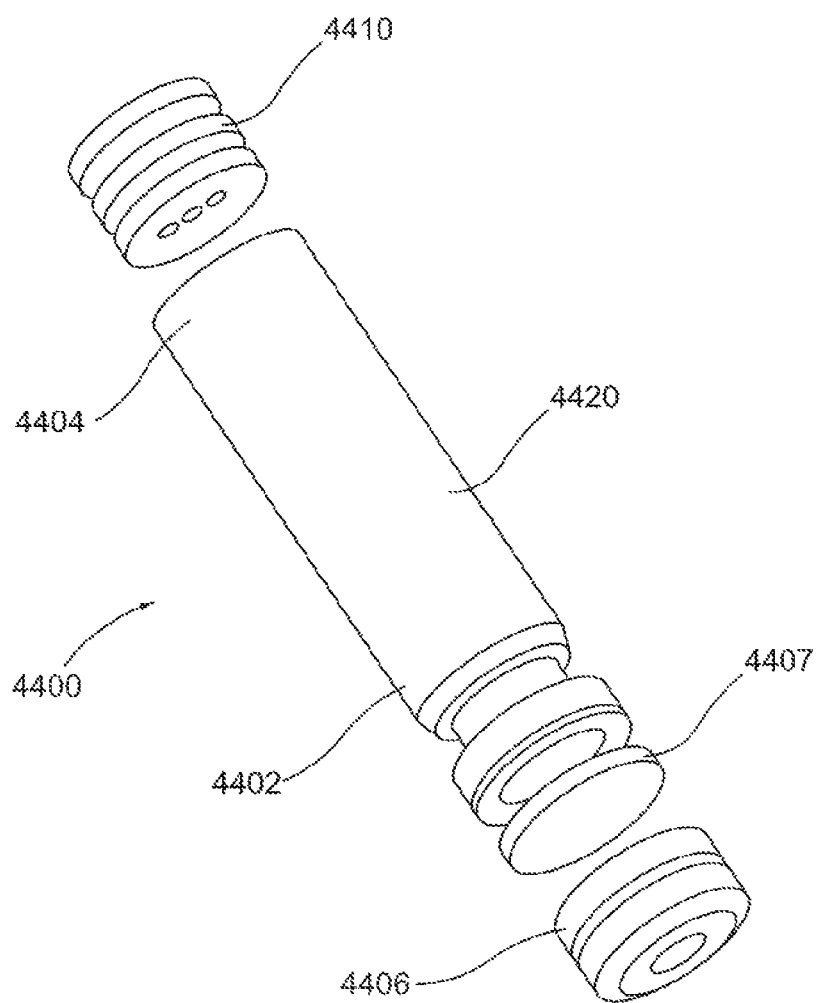
FIG. 16 is an exploded view of a medicament container of the medical injector illustrated in FIG. 4.
Figure 17:
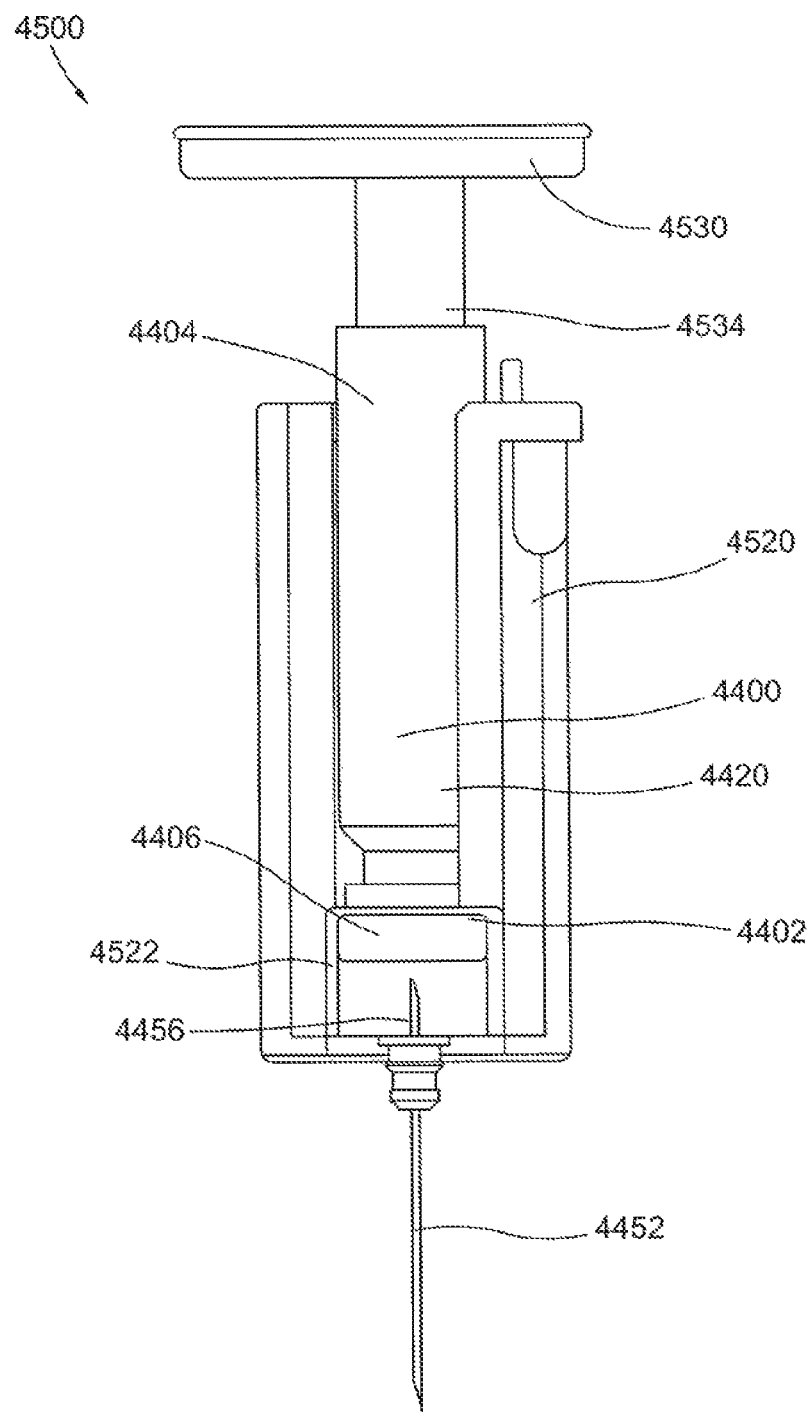
FIG. 17 is a front view of a portion of the medical injector illustrated in FIG. 4.
Figure 18:
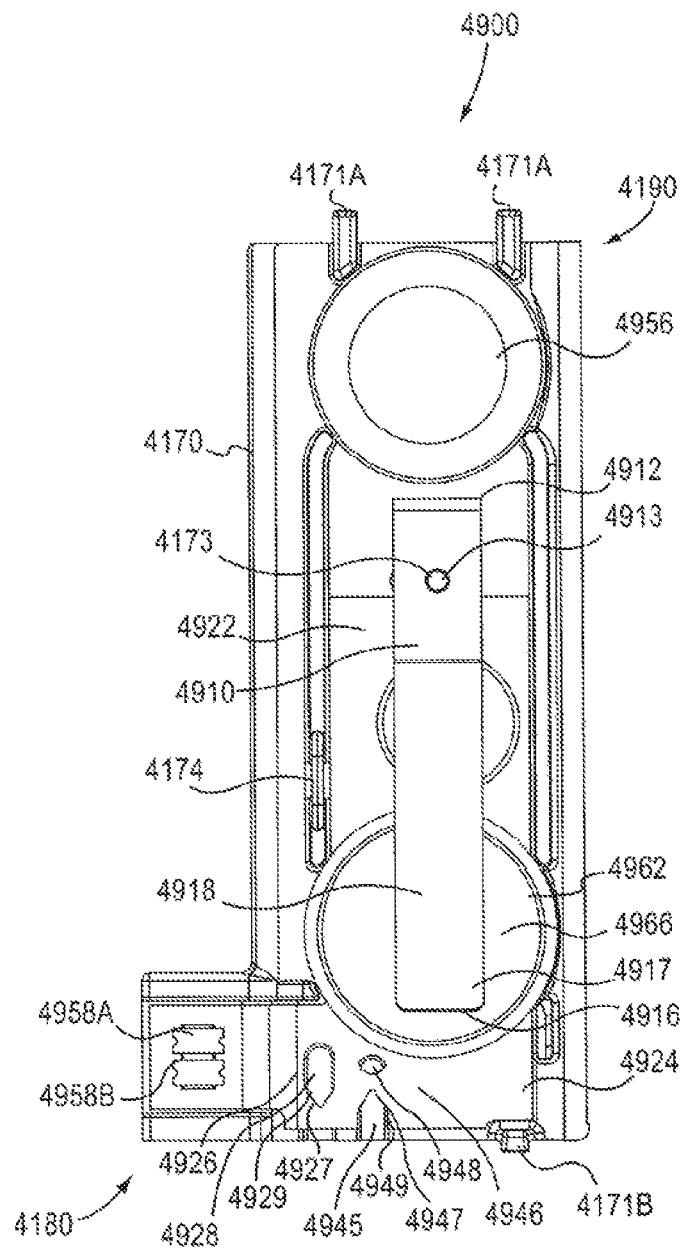
FIG. 18 is a back view of an electronic circuit system of the medical injector illustrated in FIG. 4.
Figure 19:
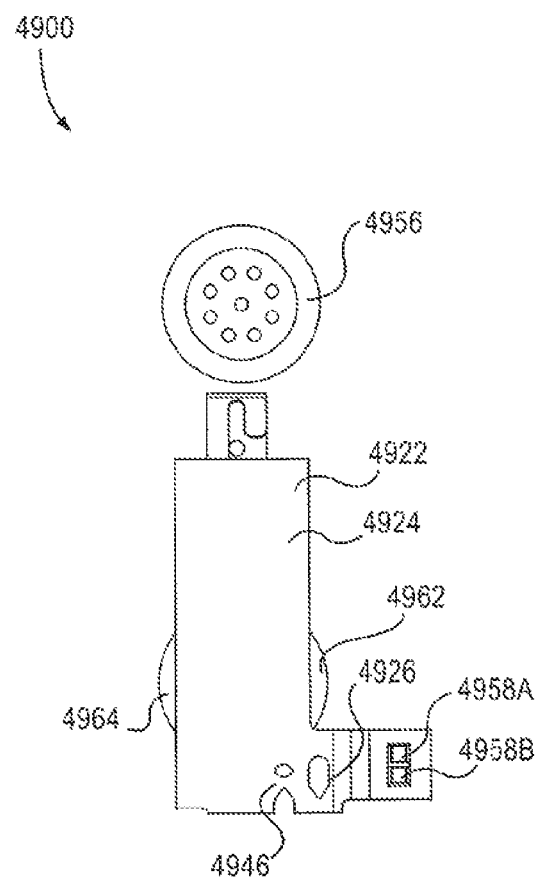
FIG. 19 is a front view of a portion of the electronic circuit system of the medical injector illustrated in FIG. 18.
Figure 20:
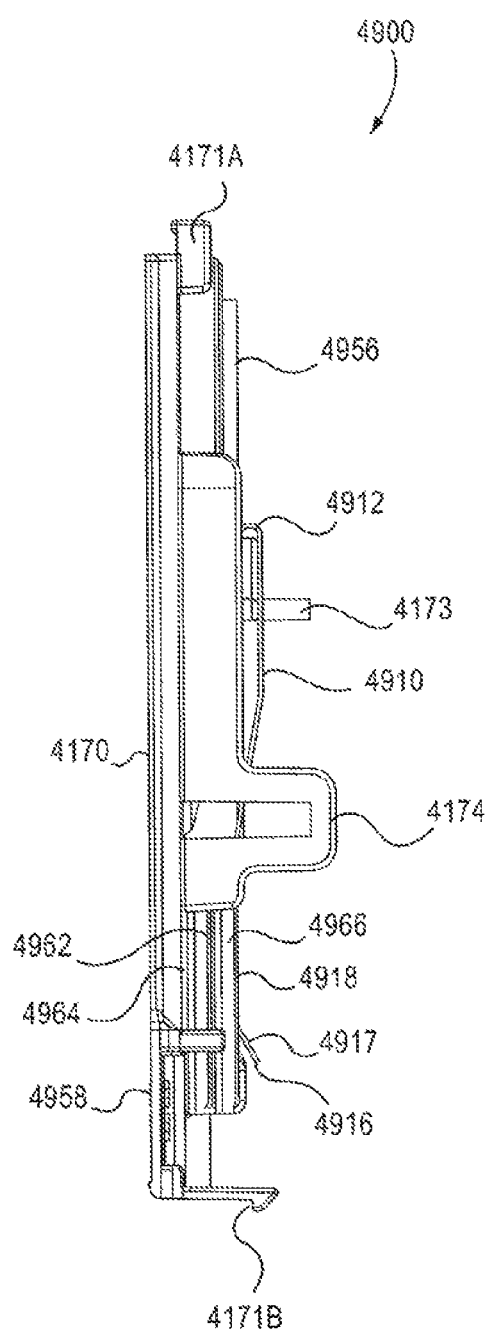
FIG. 20 is a side view of the electronic circuit system of the medical injector illustrated in FIG. 18.

The medicament container 4400 of the medicament delivery mechanism 4500 has a distal end portion 4402 and a proximal end portion 4404, and contains (i.e., is filled with or partially filled with) a naloxone composition 4420 (see, e.g., FIG. 16). The distal end portion 4402 of the medicament container 4400 contains a seal 4406. The seal 4406, which can be, for example, an 8-I crimp seal, is configured to burst when punctured by the proximal end 4456 of the needle 4452, as described below. The proximal end portion 4404 of the medicament container 4400 includes an elastomeric member 4410, and is configured to receive a piston portion 4534 of the movable member 4530. Although the medicament container 4400 is shown in FIG. 16 as including a liner 4407, in other embodiments, the medicament container 4400 need not include the liner 4407.

The medicament container 4400 can have any suitable size (e.g., length and/or diameter) and can contain any suitable volume of the naloxone composition 4420. Moreover, the medicament container 4400 and the movable member 4530 can be collectively configured such that the movable member 4530 travels a desired distance within the medicament container 4400 (i.e., the "stroke") during an injection event. In this manner, the medicament container 4400, the volume of the naloxone composition 4420 within the medicament container 4400 and the movable member 4530 can be collectively configured to provide a desired fill volume and delivery volume. In some embodiments, for example, the size of the medicament container 4400 and the length of the movable member 4530 can be such that the fill volume of the naloxone composition 4420 is approximately 0.76 ml and the delivery volume of the naloxone composition 4420 is approximately 0.30 ml (providing a delivery volume to fill volume ratio of approximately 0.4). In other embodiments, for example, the size of the medicament container 4400 and the length of the movable member 4530 can be such that the fill volume of the naloxone composition 4420 is approximately 0.66 ml and the delivery volume of the naloxone composition 4420 is approximately 0.40 ml (providing a delivery volume to fill volume ratio of approximately 0.6).

Moreover, the length of the medicament container 4400 and the length of the movable member 4530 can be configured such that the medicament delivery mechanism 4500 can fit in the same housing 4110 regardless of the fill volume, the delivery volume and/or the ratio of the fill volume to the delivery volume. In this manner, the same housing and production tooling can be used to produce devices having various dosages of the naloxone composition. For example, in a first embodiment (e.g., having a fill volume to delivery volume ratio of 0.4), the medicament container has a first length and the movable member has a first length. In a second embodiment (e.g., having a fill volume to delivery volume ratio of 0.6), the medicament container has a second length shorter than the first length, and the movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

The naloxone composition 4420 contained within the medicament container 4400 can be any of the naloxone compositions described herein. In particular, the naloxone composition 4420 can include an effective amount of naloxone or salts thereof, a tonicity-adjusting agent, and a pH adjusting agent. The naloxone composition 4420 can be formulated such that the osmolality of the naloxone composition 4420 ranges from about 250-350 mOsm and the pH ranges from about 3-5.

In some embodiments, the naloxone composition 4420 can include any suitable concentration of 4,5-epoxy-3,14-dihydroxy-17-(2-propenyl) morphinan-6-one. In some embodiments, for example, the naloxone composition 4420 has a concentration of 4,5-epoxy-3,14-dihydroxy-17-(2-propenyl)morphinan-6-one between approximately 0.01 mg/mL and approximately 10 mg/mL. In other embodiments, the naloxone composition 4420 has a concentration of 4,5-epoxy-3,14-dihydroxy-17-(2-propenyl)morphinan-6-one between approximately 0.05 mg/mL and approximately 2 mg/mL.

The tonicity-adjusting agent can be any of the tonicity-adjusting agents described herein, and can be included within the naloxone composition 4420 in any suitable amount and/or concentration. For example, in some embodiments, the tonicity-adjusting agent includes at least one of dextrose, glycerin, mannitol, potassium chloride or sodium chloride. In other embodiments, the tonicity-adjusting agent includes sodium chloride in an amount such that a concentration of sodium chloride is between approximately 0.1 mg/mL and approximately 20 mg/mL.

The pH adjusting agent can be any of the pH adjusting agents described herein, and can be included within the naloxone composition 4420 in any suitable amount and/or concentration. For example, in some embodiments, the pH adjusting agent includes at least one of hydrochloric acid, citric acid, citrate salts, acetic acid, acetate salts, phosphoric acid or phosphate salts. In other embodiments, the pH adjusting agent includes a dilute hydrochloric acid.

The elastomeric member 4410 can be of any design or formulation suitable for contact with the naloxone composition 4420. For example, the elastomeric member 4410 can be formulated to minimize any reduction in the efficacy of the naloxone composition 4420 that may result from contact (either direct or indirect) between the elastomeric member 4410 and the naloxone composition 4420. For example, in some embodiments, the elastomeric member 4410 can be formulated to minimize any leaching or out-gassing of compositions that may have an undesired effect on the naloxone composition 4420. In other embodiments, the elastomeric member 4410 can be formulated to maintain its chemical stability, flexibility and/or sealing properties when in contact (either direct or indirect) with naloxone over a long period of time (e.g., for up to six months, one year, two years, five years or longer).

In some embodiments, the elastomeric member 4410 can be formulated to include a polymer and a curing agent. In such embodiments, the polymer can include at least one of bromobutyl or chlorobutyl. In such embodiments, the curing agent can include at least one of sulfur, zinc or magnesium.

In some embodiments, the elastomeric member 4410 can be constructed from multiple different materials. For example, in some embodiments, at least a portion of the elastomeric member 4410 can be coated. Such coatings can include, for example, polydimethylsiloxane. In some embodiments, at least a portion of the elastomeric member 4410 can be coated with polydimethylsiloxane in an amount of between approximately 0.02 mg/cm$^2$ and approximately 0.80 mg/cm$^2$.

As shown in FIG. 13, the system actuator 4300 includes the base 4302, a release member 4340 and a spring 4370. FIG. 14 shows certain of the internal components of the medical injector 4000 without the base 4302 and the spring 4370 so that the release member 4340 can be more clearly shown.

The release member 4340 has a proximal end portion 4342 and a distal end portion 4344, and is movably disposed within the distal end portion 4156 of the gas cavity 4154. The proximal end portion 4342 of the release member 4340 includes a sealing member 4345 and a puncturer 4341. The sealing member 4345 is configured to engage the sidewall of the housing 4110 defining the gas cavity 4154 such that the proximal end portion 4155 of the gas cavity 4154 is fluidically isolated from the distal end portion 4156 of the gas cavity 4154. In this manner, when gas is released from the gas container 4570, the gas contained in the proximal end portion 4155 of the gas cavity 4154 is unable to enter the distal end portion 4156 of the gas cavity 4154. The puncturer 4341 of the proximal end portion 4342 of the release member 4340 is configured to contact and puncture a frangible seal 4573 on the gas container 4570 when the release member 4340 moves proximally within the gas cavity 4154, as shown by the arrow BB in FIG. 14.

Figure 15:
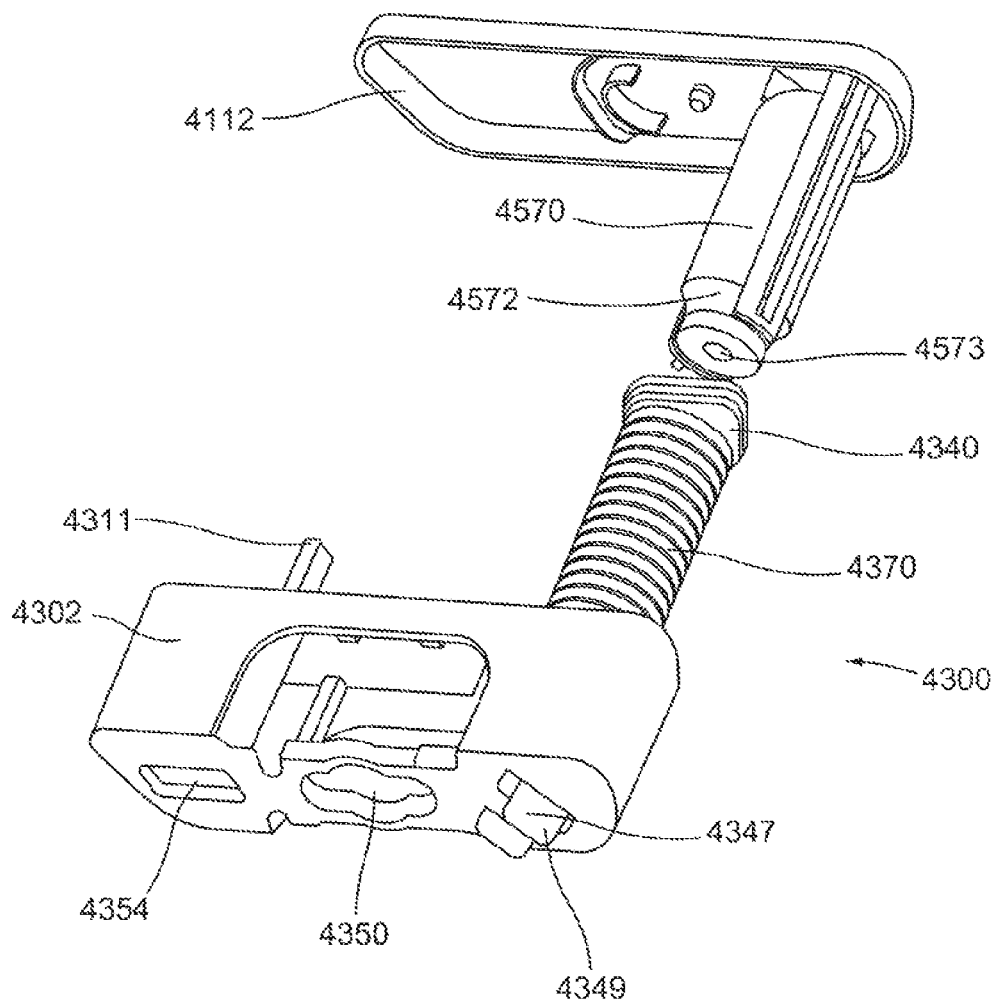
FIG. 15 is a perspective view of a portion of the medical injector illustrated in FIG. 4.

The distal end portion 4344 of the release member 4340 includes extensions 4343. The extensions 4343 include projections 4347 that include tapered surfaces 4349 and engagement surfaces 4348. Further, the extensions 4343 define an opening 4346 between the extensions 4343. The engagement surfaces 4348 of the projections 4347 are configured to extend through the safety lock aperture 4128 of the housing 4110 and contact a distal surface of the housing 4110, as shown in FIG. 15. In this manner, the engagement surfaces 4348 of the projections 4347 limit proximal movement of the release member 4340 when the engagement surfaces 4348 are in contact with the distal surface of the housing 4110.

Figure 27:
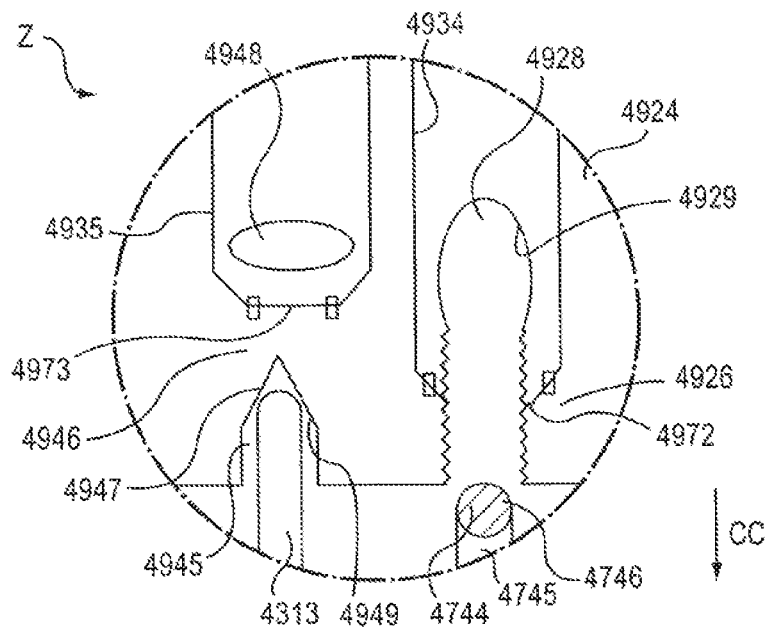

The opening 4346 defined by the extensions 4343 is configured to receive the safety lock protrusion 4742 of the safety lock 4700 (see e.g., FIGS. 15 and 27). The safety lock protrusion 4742 is configured to prevent the extensions 4343 from moving closer to each other. Said another way, the safety lock protrusion 4742 is configured to ensure that the extensions 4343 remain apart and the engagement surfaces 4348 of the projections 4347 remain in contact with the distal end portion 4120 of the housing 4110. In some embodiments, for example, the release member 4340 and/or the extensions 4343 can be constructed from any suitable material configured to withstand deformation that may occur when exposed to a load over an extended period of time. In some embodiments, for example, the release member 4340 and/or the extensions 4343 can be constructed from brass.

The tapered surfaces 4349 of the projections 4347 are configured to contact protrusions 4313 on a proximal surface 4310 of the base 4302 (see e.g., FIG. 35) when the base 4302 is moved proximally relative to the housing 4110. Accordingly, when the base 4302 is moved proximally relative to the housing 4110, the extensions 4343 are moved together by the contact protrusions 4313. The inward movement of the extensions 4343 causes the release member 4340 to become disengaged from the distal end portion of the housing 4110, thereby allowing the release member 4340 to be moved proximally along its longitudinal axis as the spring 4370 expands.

The medicament delivery mechanism 4500 includes a gas container 4570, a carrier 4520, a movable member 4530, and a retraction spring 4590. As described above, the carrier 4520 and the movable member 4530 are disposed within the medicament cavity 4157 of the housing 4110. The gas container 4570 is disposed within the gas cavity 4154 of the housing 4110.

The gas container 4570 includes a distal end portion 4572 and a proximal end portion 4576, and is configured to contain a pressurized gas. The distal end portion 4572 of the gas container 4570 contains a frangible seal 4573 configured to break when the puncturer 4341 of the proximal end portion 4342 of the release member 4340 contacts the frangible seal 4573. The gas container retention member 4580 of the proximal cap 4112 of the housing 4110 is configured to receive and/or retain the proximal end portion 4576 of the gas container 4570. Said another way, the position of the gas container 4570 within the gas cavity 4154 is maintained by the gas container retention member 4580.

The movable member 4530 of the medicament delivery mechanism 4500 is movably disposed within the medicament cavity 4157. The movable member 4530 includes a piston portion 4534 having a plunger at the distal end portion of the piston portion 4534. The piston portion 4534 is configured to move within the medicament container 4400. In this manner, the piston portion 4534 of the movable member 4530 can apply a force to the elastomeric member 4410 to convey the naloxone composition 4420 contained in the medicament container 4400. The piston portion 4534 can be constructed of a resilient, durable, and/or sealing material, such as a rubber.

The carrier 4520 of the medicament delivery mechanism 4500 includes a distal end portion 4522 and a proximal end portion 4526. The medicament container 4400 is coupled to the carrier 4520 via a "snap-fit" connection (not shown) such that the medicament container 4400 can move relative to the carrier 4520 between a first configuration and a second configuration during an injection event. In the first configuration, the carrier 4520 is configured to move within the medicament cavity 4157 such that movement of the carrier 4520 within the medicament cavity 4157 causes contemporaneous movement of the medicament container 4400 within the medicament cavity 4157. The proximal end portion 4456 of the needle 4452 is spaced apart from the seal 4406 of the medicament container 4400 when the carrier 4520 and the medicament container 4400 are collectively in the first configuration (e.g., during needle insertion). When the carrier 4520 and the medicament container 4400 are moved to the second configuration, the medicament container 4400 releases from the "snap-fit" causing the medicament container 4400 to move distally with respect to the carrier 4520, causing the proximal end portion 4456 of the needle 4452 to pierce the seal 4406. In this manner, the needle 4452 can be selectively placed in fluid communication with the medicament container 4400 to define a medicament delivery path (not shown).

Figure 41:
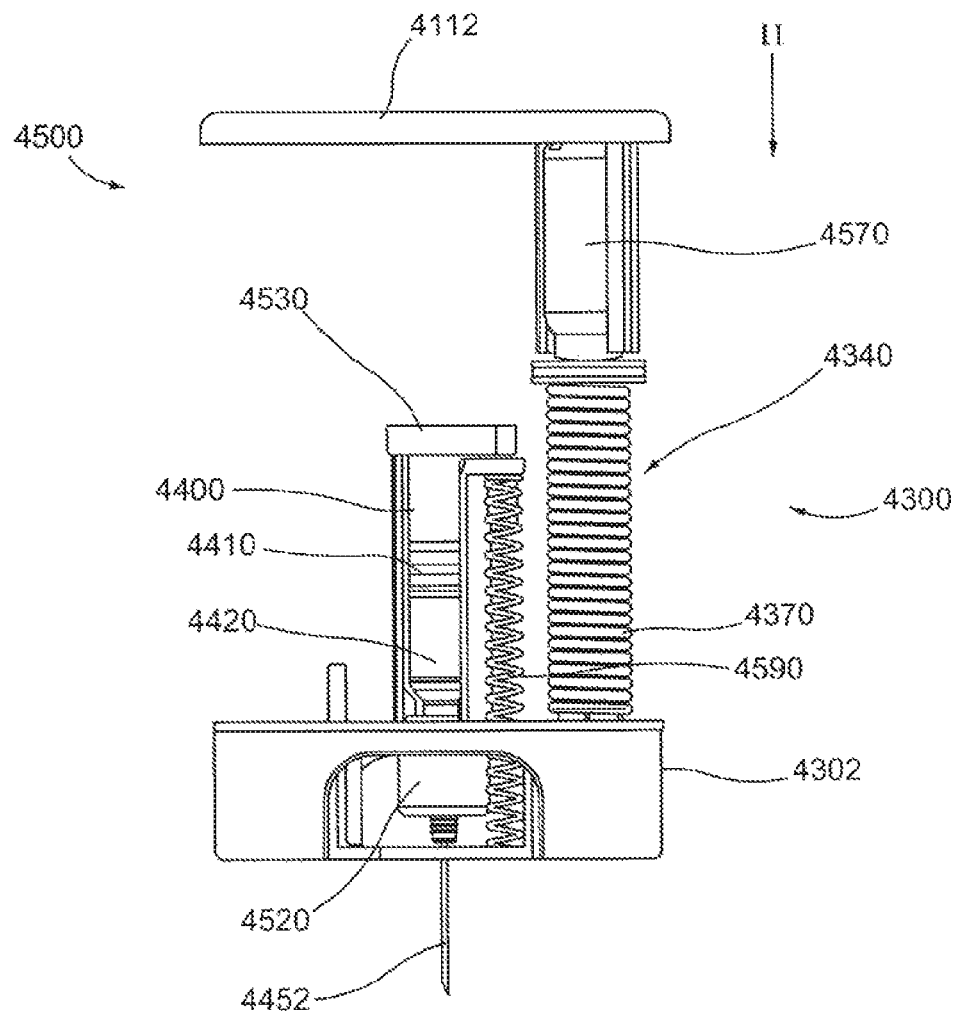
FIG. 41 is a front view of the medical injector illustrated in FIG. 4 in a fifth configuration (i.e., the injection configuration).

As shown in FIGS. 13, 14 and 41, the proximal end portion 4526 of the carrier 4520 includes a gas valve actuator 4527. The gas valve actuator 4527 is configured to engage a gas relief valve (not shown) of the movable member 4530 to allow the pressurized gas contained within the gas chamber (i.e., the volume within the medicament cavity 4157 between the proximal end of the housing 4110 and the proximal end of the movable member 5530) to escape when the injection event is complete. Thus, after the gas pressure within the medicament cavity 4157 decreases below a certain level, the force exerted by the retraction spring 4590 on the carrier 4520 can be sufficient to cause the carrier 4520 to move proximally within the housing 4110 (i.e., to retract). In addition, this arrangement results in there being substantially no residual force within the housing, which decreases stress on the components after the injection event.

Figure 24:
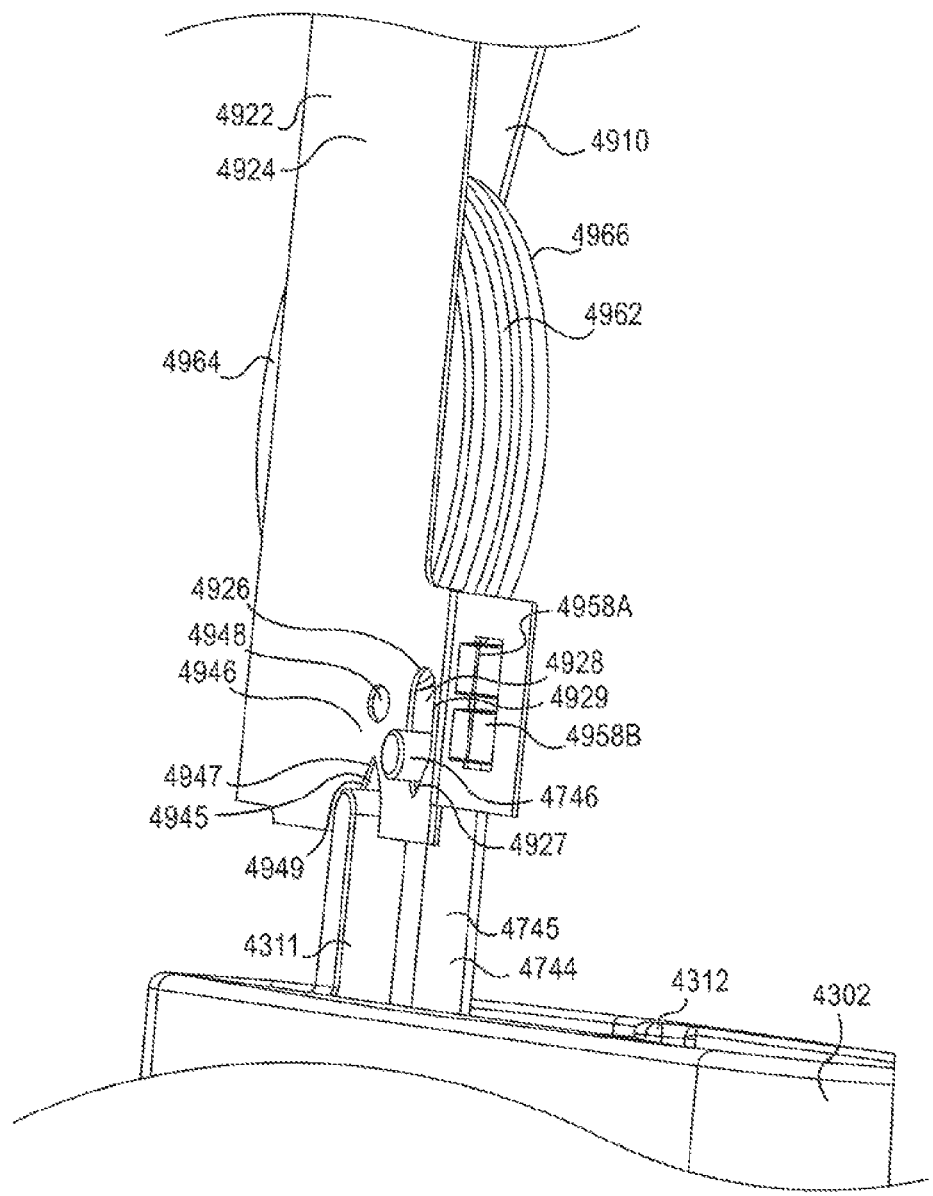
FIG. 24 is a perspective view of a portion of an electronic circuit system of the medical injector illustrated in FIG. 4, in a first configuration.
Figure 25:
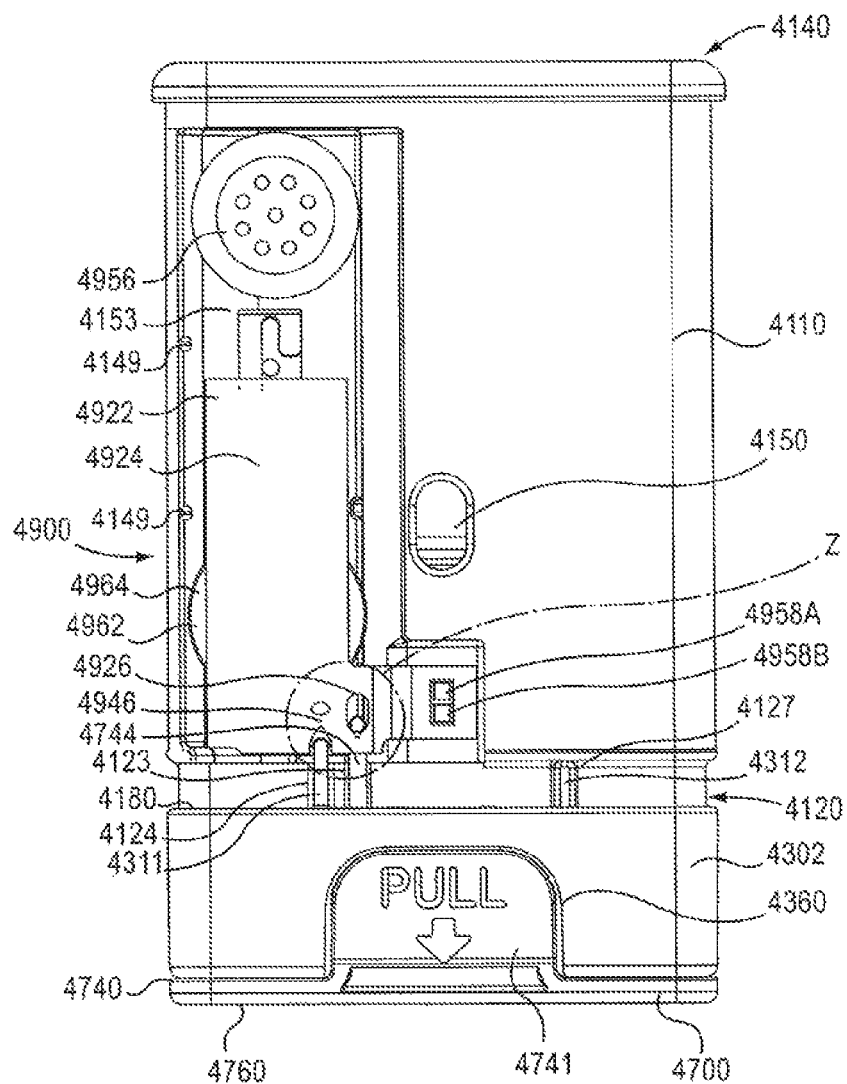
FIG. 25 is a front view of the medical injector illustrated in FIG. 4 in a first configuration showing the electronic circuit system.

FIGS. 18-28 show the electronic circuit system 4900. The electronic circuit system 4900 of the medical injector 4000 includes an electronic circuit system housing 4170, a printed circuit board 4922, a battery assembly 4962, an audio output device 4956, two light emitting diodes (LEDs) 4958A, 4958B and a battery clip 4910. As shown in FIG. 25, the electronic circuit system 4900 is configured to fit within the electronic circuit system cavity 4153 of the housing 4110. Accordingly, as described above, the electronic circuit system 4900 is physically and/or fluidically isolated from the medicament cavity 4157, the gas cavity 4154 and/or the medicament delivery device 4500. As described herein, the electronic circuit system 4900 is configured to output an electronic output associated with the use of the medical injector 4000.

The electronic circuit system housing 4170 of the electronic circuit system 4900 includes a distal end portion 4180 and a proximal end portion 4190. The proximal end portion 4190 includes connection protrusions 4171A and a battery clip protrusion 4173. The connection protrusions 4171A extend from the proximal end portion 4190 of the electronic circuit system housing 4170, and are configured to be disposed within the connection apertures 4152 of the housing 4110, as described above. In this manner, the electronic circuit system 4900 can be coupled to the housing 4110 within the electronic circuit system cavity 4153. In other embodiments, the electronic circuit system 4900 can be coupled to the housing 4110 by other suitable means such as an adhesive, a clip, a label and/or the like. As described in more detail herein, the battery clip protrusion 4173 is configured to hold the battery clip 4910 in place.

The proximal end portion 4190 of the electronic circuit system housing 4170 defines multiple sound apertures 4191. The audible output device 4956 is disposed against the proximal end portion 4190 of the electronic circuit system housing 4170 such that the front face of the audible output device 4956 is disposed adjacent the sound apertures 4191. In this manner, the sound apertures 4191 are configured to allow sound from an audio output device 4956 to pass from the audio output device 4956 to a region outside of the housing 4110.

Figure 21:
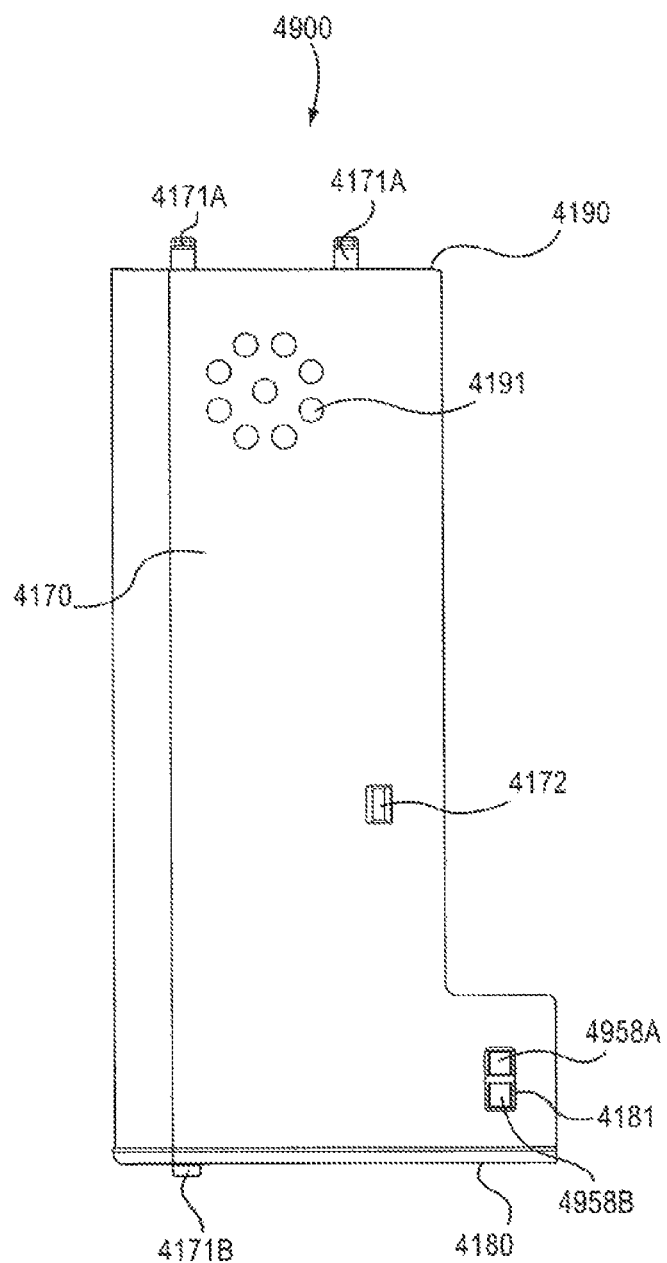
FIG. 21 is a front view of an electronic circuit system housing of the electronic circuit system illustrated in FIG. 18.
Figure 22:
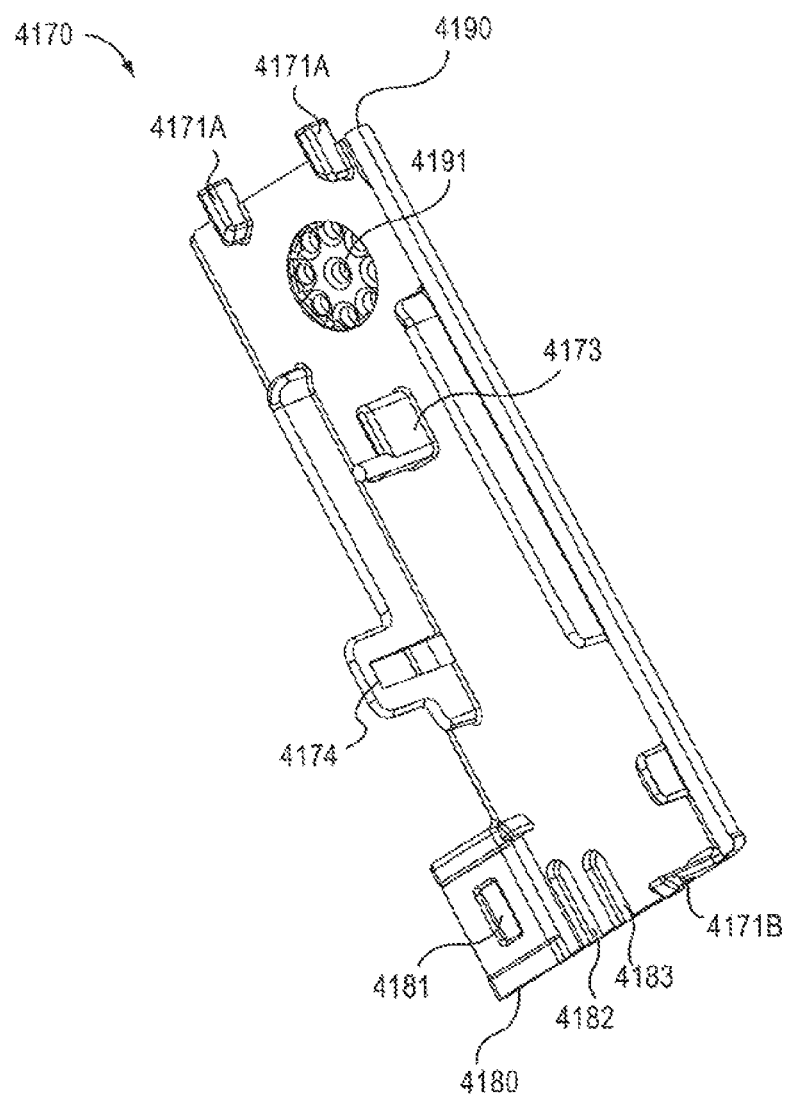
FIG. 22 is a perspective view of the electronic circuit system housing of the electronic circuit system illustrated in FIG. 21.
Figure 23:
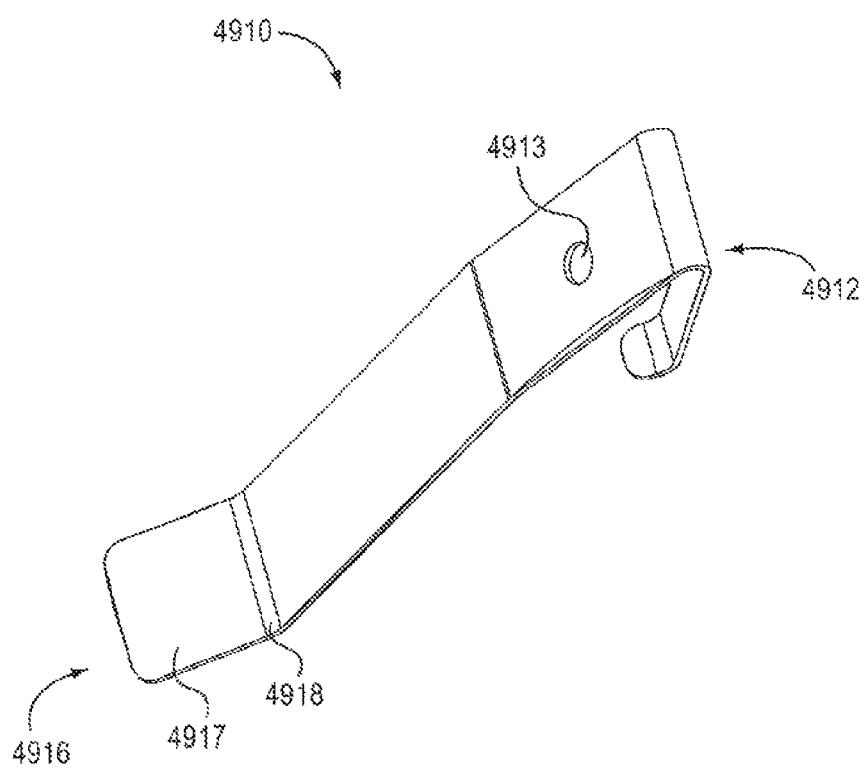
FIG. 23 is a perspective view of a battery clip of the electronic circuit system illustrated in FIG. 18.

As shown in FIGS. 21 and 22, the distal end portion 4180 of the electronic circuit system housing 4170 includes a connection protrusion 4171B, a stiffening protrusion 4174, and defines an LED aperture 4181, an aperture 4172, a safety lock actuator groove 4182, and a base actuator groove 4183. The LED aperture 4181 is configured to receive the LEDs 4958A, 4958B such that a user can view the LEDs 4958A, 4958B, which are described in more detail herein.

The connection protrusion 4171B extends from the distal end portion 4180 of the electronic circuit system housing 4170, and is configured to attach the electronic circuit system 4900 to the housing 4110, as described above. The stiffening protrusion 4174 is configured to have at least a portion received within and/or accessible via the aperture 4145 in the housing 4110 (see e.g., FIG. 7). The stiffening protrusion 4174 is configured to limit the bending (e.g., buckling) of the electronic circuit system housing 4170 when the electronic circuit system housing 4170 is coupled to the housing 4110. Moreover, a user can access the stiffening protrusion 4174 via the aperture 4172. In this manner, for example, the user can disengage the stiffening protrusion 4174 from the aperture 4145.

The safety lock actuator groove 4182 of the electronic circuit system housing 4170 is configured to be disposed adjacent the safety lock actuator groove 4123 of the distal end portion 4120 of the housing 4110. In this manner, the safety lock actuator groove 4182 of the electronic circuit system housing 4170 and the safety lock actuator groove 4123 of the distal end portion 4120 of the housing 4110 collectively receive the actuator 4744 of the safety lock 4700, which is described in more detail herein. Similarly, the base actuator groove 4183 of the electronic circuit system housing 4170 is configured to be disposed about the base actuator groove 4124 of the distal end portion 4120 of the housing 4110. The base actuator groove 4183 of the electronic circuit system housing 4170 and the base actuator groove 4124 of the distal end portion 4120 of the housing 4110 collectively receive the actuator 4311 of the base 4302, which is described in more detail herein.

The printed circuit board 4922 of the electronic circuit system 4900 includes a substrate 4924, a first actuation portion 4926 and a second actuation portion 4946. The substrate 4924 of the printed circuit board 4922 includes the electrical components necessary for the electronic circuit system 4900 to operate as desired. For example, the electrical components can be resistors, capacitors, inductors, switches, microcontrollers, microprocessors and/or the like. The printed circuit board may also be constructed of materials other than a flexible substrate such as a FR4 standard board (rigid circuit board).

Figure 26:
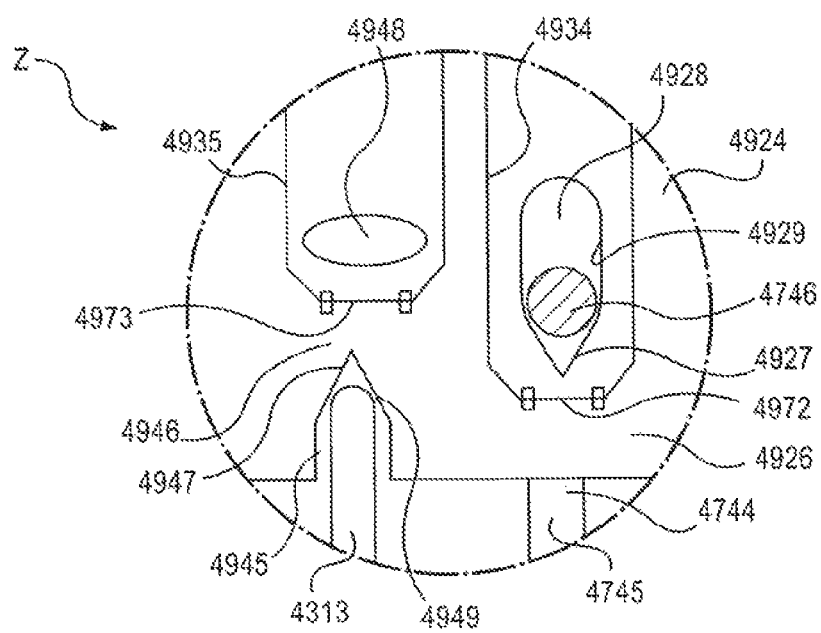
FIGS. 26-28 are front views of a portion of the electronic circuit system of the medical injector labeled as Region Z in FIG. 25 in a first configuration, a second configuration, and a third configuration, respectively.
Figure 28:
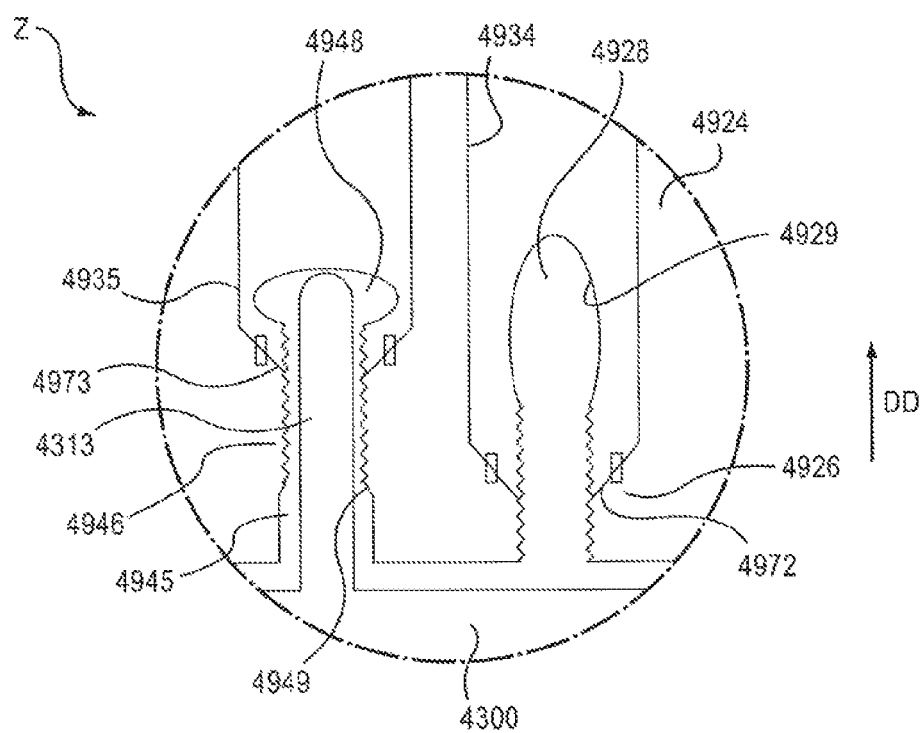

As shown in FIGS. 26-28, the first actuation portion 4926 includes a first electrical conductor 4934 and defines an opening 4928 having a boundary 4929. The opening 4928 of the first actuation portion 4926 is configured to receive a protrusion 4746 of the actuator 4744 of the safety lock 4700. The boundary 4929 of the first opening 4928 has a discontinuous shape, such as, for example, a teardrop shape, that includes a stress concentration riser 4927. The discontinuity and/or the stress concentration riser 4927 of the boundary 4929 can be of any suitable shape to cause the substrate 4924 to deform in a predetermined direction when the protrusion 4746 of the actuator 4744 of the safety lock 4700 is moved relative to the opening 4928, as shown by the arrow CC in FIG. 27.

The opening 4928 is defined adjacent the first electrical conductor 4934 that electronically couples the components included in the electronic circuit system 4900. The first electrical conductor 4934 includes a first switch 4972, which can be, for example a frangible portion of the first electrical conductor 4934. In use, when the safety lock 4700 is moved from a first position (see e.g., FIG. 26) to a second position (see e.g., FIG. 27), the actuator 4744 moves in a direction substantially parallel to a plane defined by a surface of the first actuation portion 4926 of the substrate 4924. The movement of the actuator 4744 causes the protrusion 4746 to move within the first opening 4928, as indicated by the arrow CC in FIG. 27. The movement of the protrusion 4746 tears the first actuation portion 4926 of the substrate 4924, thereby separating the portion of the first electrical conductor 4934 including the first switch 4972. Said another way, when the safety lock 4700 is moved from its first position to its second position (see e.g., FIG. 38), the actuator 4744 moves irreversibly the first switch 4972 from a first state (e.g., a state of electrical continuity) to a second state (e.g., a state of electrical discontinuity). Said yet another way, when the safety lock 4700 is moved from its first position to its second position, the actuator 4744 disrupts the first electrical conductor 4934.

The second actuation portion 4946 includes a second electrical conductor 4935 and defines an opening 4945, having a boundary 4949 and a tear propagation limit aperture 4948. As shown in FIGS. 25-28, the opening 4945 of the second actuation portion 4946 is configured to receive a portion of an actuator 4311 of the base 4302. The boundary 4949 of the opening 4945 has a discontinuous shape that includes a stress concentration riser 4947. The discontinuity and/or the stress concentration riser 4947 of the boundary 4949 can be of any suitable shape to cause the substrate 4924 to deform in a predetermined direction when the actuator 4311 of the base 4302 is moved in a proximal direction relative to the opening 4945, as shown by the arrow DD in FIG. 23.

The second electrical conductor 4935 includes a second switch 4973 disposed between the opening 4945 and the tear propagation limit aperture 4948, which can be, for example, a frangible portion of the second electrical conductor 4935. In use, when the base 4302 is moved from its first position to its second position (see e.g., FIG. 39), the actuator 4311 moves in a proximal direction, substantially parallel to a plane defined by a surface of the second actuation portion 4946 of the substrate 4924. The proximal movement of the actuator 4311 tears the second actuation portion 4946 of the substrate 4924, thereby separating the portion of the second electrical conductor 4935 including the second switch 4973. Said another way, when the base 4302 is moved from its first position to its second position, the actuator 4311 moves irreversibly the second switch 4973 from a first state (e.g., a state of electrical continuity) to a second state (e.g., a state of electrical discontinuity). The tear propagation limit aperture 4948 is configured to limit the propagation of the tear in the substrate 4924 in the proximal direction. Said another way, the tear propagation limit aperture 4948 is configured to ensure that the tear in the substrate 4924 does not extend beyond the tear propagation limit aperture 4948. The tear propagation limit aperture 4948 can be any shape configured to stop the propagation of a tear and/or disruption of the substrate 4924. For example, the tear propagation limit aperture 4948 can be oval shaped. In other embodiments, the proximal boundary of the tear propagation limit aperture 4948 can be reinforced to ensure that the tear in the substrate 4924 does not extend beyond the tear propagation limit aperture 4948.

In some embodiments, the safety lock 4700 and base 4302 can be configured to interact with mechanical and/or optical switches to produce an electronic output in a reversible manner.

The battery assembly 4962 of the electronic circuit system 4900 includes two batteries stacked on top of one another. In other embodiments, the electronic circuit system can include any number of batteries and/or any suitable type of power source. In some embodiments, for example, the battery assembly can include Lithium batteries such as, for example, CR1616, CR2016s, type AAA or the like. The battery assembly 4962 has a first surface 4964 and a second surface 4966. The first surface 4964 of the battery assembly 4962 can contact an electrical contact (not shown) disposed on the substrate 4924. The second surface 4966 of the battery assembly 4962 is configured to contact a contact portion 4918 of a distal end portion 4916 of a battery clip 4910. When both the electrical contact of the substrate 4924 and the contact portion 4918 of the distal end portion 4916 of the battery clip 4910 contact the battery assembly 4962, the batteries of the battery assembly 4962 are placed in electrical communication with the electronic circuit system 4900. Said another way, when the electrical contact of the substrate 4924 and the contact portion 4918 of the distal end portion 4916 of the battery clip 4910 contact the battery assembly 4962, the battery assembly 4962 is configured to supply power to the electronic circuit system 4900.

The battery clip 4910 (shown in FIG. 23) includes a proximal end portion 4912 and a distal end portion 4916. The proximal end portion 4912 defines a retention aperture 4913. The retention aperture 4913 is configured to receive the battery clip protrusion 4173 of the electronic circuit system housing 4170. In this manner, the battery clip protrusion 4173 maintains the position of the battery clip 4910 with respect to the electronic circuit system housing 4170 and/or the battery assembly 4962.

The distal end portion 4916 of the battery clip 4910 includes a contact portion 4918 and an angled portion 4917. As described above, the contact portion 4918 is configured to contact the second surface 4966 of the battery assembly 4962 to place the battery assembly 4962 in electrical communication with the electronic circuit system 4900. The angled portion 4917 of the distal end portion 4916 of the battery clip 4910 is configured to allow a proximal end portion 4236 of a battery isolation protrusion 4235 (see e.g., FIG. 30) to be disposed between the second surface 4966 of the battery assembly 4962 and the contact portion 4918 of the distal end portion 4916 of the battery clip 4910. When the battery isolation protrusion 4235 is disposed between the second surface 4966 of the battery assembly 4962 and the contact portion 4918 of the distal end portion 4916 of the battery clip 4910, the electrical path between the battery assembly 4962 and the remainder of the electrical circuit system 4900 is severed, thereby removing power from the electronic circuit system 4900. The contact portion 4918 of the distal end portion 4916 of the battery clip 4910 is biased such that when the battery isolation protrusion 4235 is removed, the contact portion 4918 will move into contact the second surface 4966 of the battery assembly 4962, thereby restoring electrical communication between the battery assembly 4962 and the electronic circuit system 4900. In some embodiments, the battery isolation protrusion 4235 can be repeatedly removed from between the second surface 4966 of the battery assembly 4962 and the contact portion 4918 of the distal end portion 4916 of the battery clip 4910 and reinserted. Said another way, the battery isolation protrusion 4235 and the battery clip 4910 collectively form a reversible on/off switch.

The audio output device 4956 of the electronic circuit system 4900 is configured to output audible sound to a user in response to a use of the medical injector 4000. In some embodiments, the audible output device 4956 can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 4000 can have a network interface device (not shown) configured to operatively connect the electronic circuit system 4900 to a remote device (not shown) and/or a communications network (not shown). In this manner, the electronic circuit system 4900 can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 4900. In some embodiments, for example, the electronic circuit system 4900 can download information associated with a medical injector 4000, such as an expiration date, a recall notice, updated use instructions or the like. Similarly, in some embodiments, the electronic circuit system 4900 can upload compliance information associated with the use of the medical injector 4000 via the network interface device.

FIGS. 24 and 25 show the cover 4200 of the medical injector 4000. The cover 4200 includes a proximal end portion 4210 and a distal end portion 4230, and defines a cavity 4242. The cavity 4242 of the cover 4200 is configured to receive at least a portion of the housing 4110. Thus, when the portion of the housing 4110 is disposed within the cover 4200, the cover 4200 blocks an optical pathway between the medicament container 4400 and a region outside of the housing 4110. Similarly stated, when the portion of the housing 4110 is disposed within the cover 4200, the cover 4200 is obstructs the first status indicator aperture 4150 and/or the second status indicator aperture 4151 of the housing 4110 to reduce the amount of light transmitted to the naloxone composition 4420 within the medicament container 4400. In this manner, the life of the naloxone composition 4420 can extended by the prevention and/or reduction of degradation to the naloxone that may be caused by ultra-violet radiation.

The proximal end portion 4210 of the cover 4200 defines apertures 4215 configured to receive the cover retention protrusions 4142 of the housing 4110 (shown in FIGS. 5 and 7). In this manner, the apertures 4215 and the cover retention protrusions 4142 of the housing 4110 removably retain the cover 4200 about at least a portion of the housing 4110. Said another way, the apertures 4215 and the cover retention protrusions 4142 of the housing 4110 are configured such that the cover 4200 can be removed from a portion of the housing 4110 and then replaced about the portion of the housing 4110.

As described above, the electronic circuit system 4900 can be actuated when the housing 4110 is at least partially removed from the cover 4200. More particularly, the distal end portion 4230 of the cover 4200 includes a battery isolation protrusion 4235. The battery isolation protrusion 4235 includes a proximal end portion 4236 and a tapered portion 4237. The proximal end portion 4236 of the battery isolation protrusion 4235 is configured to be removably disposed between the second surface 4966 of the battery assembly 4962 and the contact portion 4918 of the distal end portion 4916 of the battery clip 4910, as described above.

FIGS. 31-34 show the safety lock 4700 of the medical injector 4000. The safety lock 4700 of the medical injector 4000 includes a proximal surface 4740, a distal surface 4760 opposite the proximal surface 4740 and a needle sheath 4720. The safety lock 4700 defines a needle sheath aperture 4770 and a battery isolation protrusion aperture 4775. The battery isolation protrusion aperture 4775 is configured to receive the battery isolation protrusion 4235 of the cover 4200 such that the battery isolation protrusion 4235 can be disposed within the electronic circuit system cavity 4153 or the electronic circuit system 4900, as described above. Similarly stated, the battery isolation protrusion aperture 4775 of the safety lock 4700 is aligned with the battery isolation protrusion aperture 4121 of the housing 4110, such that the battery isolation protrusion 4235 can be disposed within the electronic circuit system cavity 4153 when the cover 4200 is disposed about a portion of the housing 4110.

The proximal surface 4740 of the safety lock 4700 includes a safety lock protrusion 4742, a stopper 4743, an actuator 4744 and two opposing pull tabs 4741. As described above, when the safety lock 4700 is in a first (locked) position, the safety lock protrusion 4742 is configured to be disposed in the opening 4346 defined by the extensions 4343 of the distal end portion 4344 of the release member 4340 (see also FIG. 15). Accordingly, the safety lock protrusion 4742 is configured to prevent the extensions 4343 from moving closer to each other, thereby preventing proximal movement of the release member 4340 of the medicament delivery mechanism 4500 and/or delivery of the naloxone composition 4420. The stopper 4743 of the safety lock 4700 is a protrusion extending from the proximal surface 4740 of the safety lock 4700. The stopper 4743 is configured to contact a portion of the housing 4110 to limit the proximal movement of the safety lock 4700 relative to the housing 4110. In other embodiments, the stopper 4743 can be any structure configured to limit the proximal movement of the safety lock 4700.

The actuator 4744 of the safety lock 4700 has an elongated portion 4745 and a protrusion 4746. The elongated portion 4745 extends in a proximal direction from the proximal surface 4740. In this manner, the elongated portion 4745 can extend through a safety lock actuator opening 4356 of the base 4302 (see e.g., FIG. 35) and within the safety lock actuator groove 4123 of the housing 4110 and the safety lock actuator groove 4182 of the electronic circuit system housing 4170. The protrusion 4746 extends in a direction substantially transverse to the elongated portion 4745 and/or substantially parallel to the proximal surface 4740 of the safety lock 4700. As described above, the opening 4928 of the first actuation portion 4926 is configured to receive the protrusion 4746 of the actuator 4744 of the safety lock 4700.

The pull tabs 4741 of the safety lock 4700 include a grip portion 4747 and indicia 4748. The grip portion 4747 of the pull tabs 4741 provides an area for the user to grip and/or remove the safety lock 4700 from the rest of the medicament delivery system 4700. The indicia 4748 provides instruction on how to remove the safety lock 4700. In some embodiments, for example, the indicia 4748 can indicate the direction the user should pull the safety lock 4700 to remove the safety lock 4700.

Figure 33:
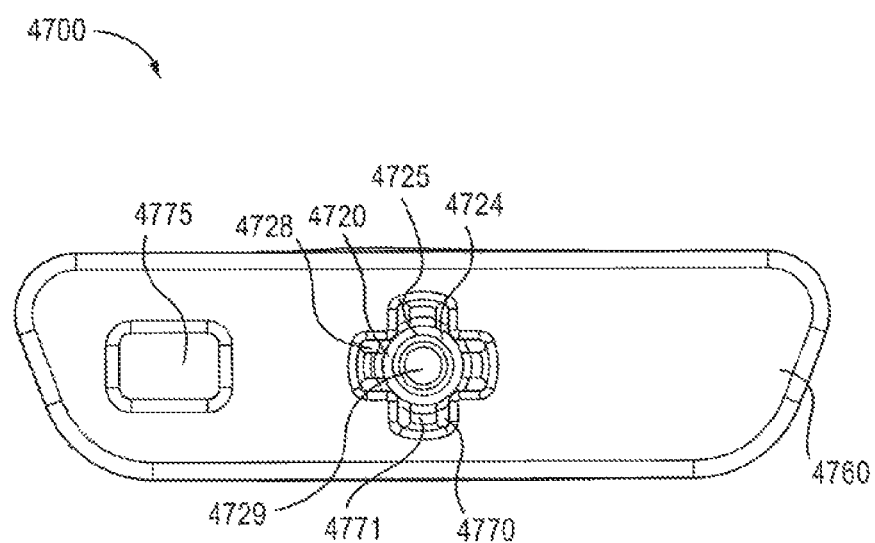
FIG. 33 is a bottom view of the safety lock of the medical injector illustrated in FIG. 31.
Figure 34:
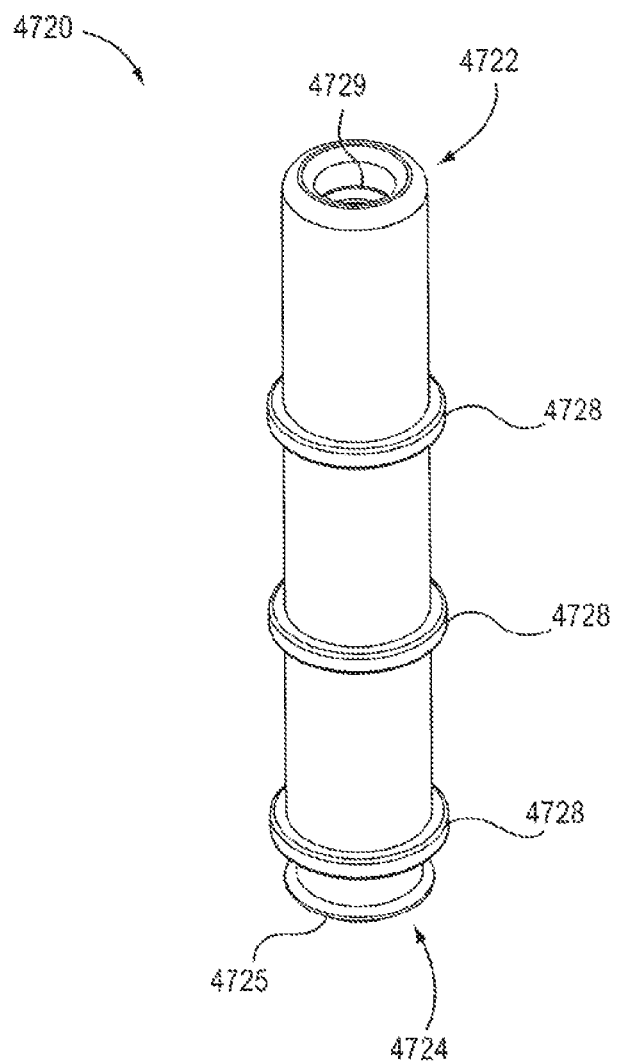
FIG. 34 is a perspective view of a needle sheath of the safety lock of the medical injector illustrated in FIG. 31.

As shown in FIG. 33, the needle sheath 4720 of the safety lock 4700 includes a distal end portion 4724, a proximal end portion 4722 and a plurality of ribs 4728. The needle sheath 4720 can also define a lumen 4729. The lumen 4729 of the safety lock 4700 is configured to receive the needle 4452. In this manner, the needle sheath 4720 can protect the user from the needle 4452 and/or can keep the needle 4452 sterile before the user actuates the medical injector 4000. The proximal end portion 4722 of the needle sheath is configured to contact the distal end portion 4522 of the carrier 4520 of the medicament delivery mechanism 4500.

The distal end portion 4724 of the needle sheath 4720 has an angled ridge 4725. The angled ridge 4725 is configured to allow the proximal end portion 4722 of the needle sheath 4720 to irreversibly move through the needle sheath aperture 4770 of the safety lock 4700 in a distal direction. Said another way, the angled ridge 4725 can be configured in such a way as to allow the proximal end portion 4722 of the needle sheath 4720 to move through the needle sheath aperture 4770 in a distal direction, but not in a proximal direction. The needle sheath aperture 4770 has retaining tabs 4771 configured to engage the proximal end of the angled ridge 4725 when the needle sheath 4720 is moved in a proximal direction. In this manner, the retaining tabs 4771 prevent the proximal movement of the needle sheath with respect to the safety lock 4700. Further, the retaining tabs 4771 are configured to engage the proximal end of the angled ridge 4725 when the safety lock 4700 is moved in a distal direction. Said another way, as shown in FIG. 33, the needle sheath 4720 is removed from the needle 4452 when the safety lock 4700 is moved in a distal direction with respect to the housing 4110.

Figure 35:
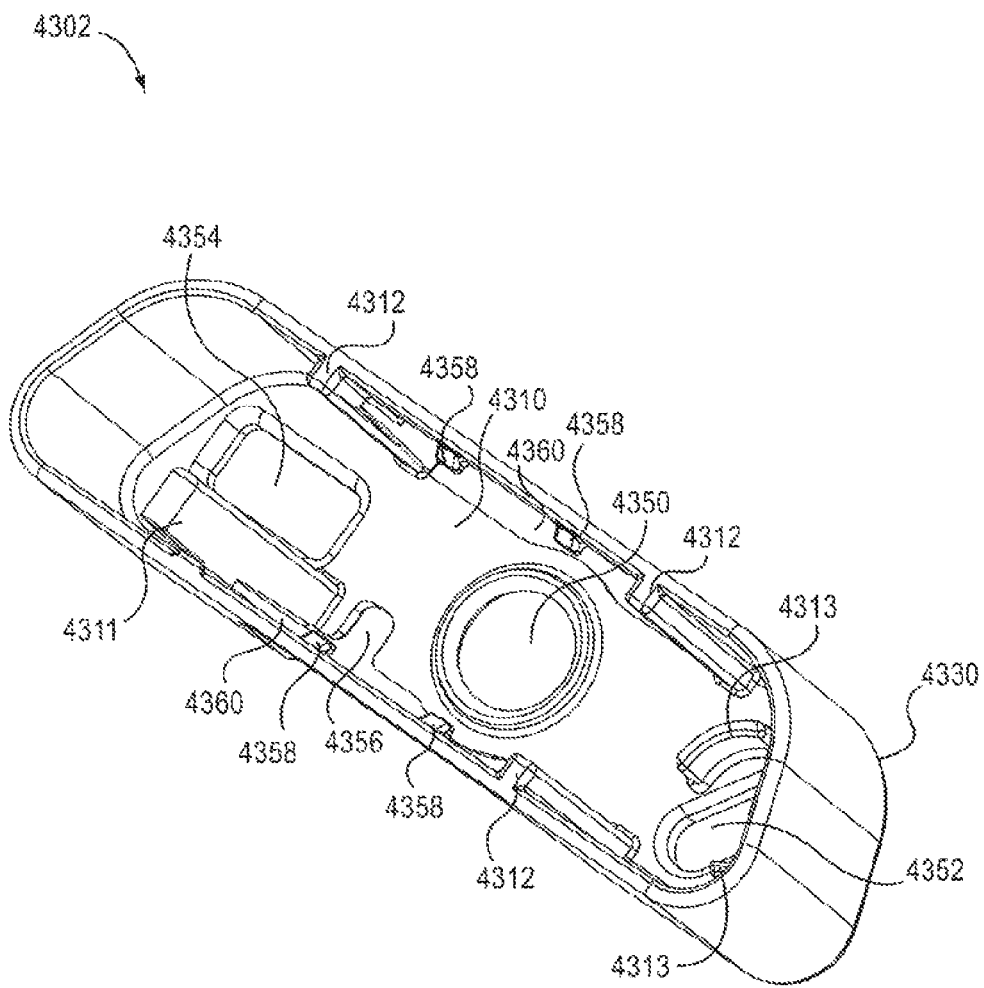
FIG. 35 is a perspective view of a base of the medical injector illustrated in FIG. 4.
Figure 36:
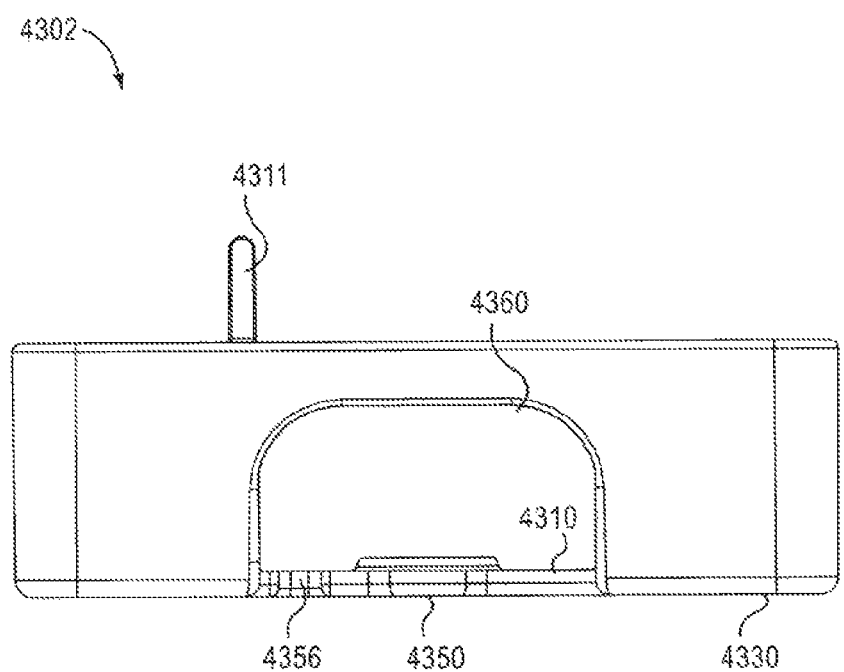
FIG. 36 is a front view of the medical injector illustrated in FIG. 4.

FIGS. 35 and 36 show the base 4302 of the medical injector 4000. The base 4302 includes a proximal surface 4310, a distal surface 4330 and base connection knobs 4358. The base 4302 defines a needle aperture 4350, a safety lock protrusion aperture 4352, a battery isolation protrusion aperture 4354, a safety lock actuator opening 4356, and pull tab openings 4360. The needle aperture 4350 is configured to receive the needle 4452 when the medical injector 4000 is actuated. The safety lock protrusion aperture 4352 of the base 4302 receives the safety lock protrusion 4742 of the safety lock 4700. The battery isolation protrusion aperture 4354 of the base 4302 receives the battery isolation protrusion 4235 of the cover 4200 and the stopper 4743 of the safety lock 4700. The safety lock actuator opening 4356 receives the safety lock actuator 4744 of the safety lock 4700. The pull tab openings 4360 are configured to receive the pull tabs 4741 of the safety lock 4700.

The proximal surface 4310 of the base 4302 includes an actuator 4311, guide members 4312, and protrusions 4313. The actuator 4311 is an elongate member configured to engage the substrate 4924 of the electronic circuit system 4900. As described above, the opening 4945 of the second actuation portion 4946 is configured to receive the actuator 4311 of the base 4302. The guide members 4312 of the base 4302 are configured to engage and/or slide within the base rail grooves 4127 of the housing 4110, as described above. The protrusions 4313 of the base 4302 are configured to engage the tapered surfaces 4349 of the extensions 4343 of the release member 4340. As described in further detail herein, when the safety lock 4700 is removed and the base 4302 is moved in a proximal direction with respect to the housing 4110, the protrusion 4313 of the base 4302 are configured to move the extensions 4343 of the release member 4340 closer to each other, actuating the medicament delivery mechanism 4500. As described above, the base connection knobs 4358 are configured to engage the base retention recesses 4125A, 4125B in a way that allows proximal movement of the base 4302 but limits distal movement of the base 4302.

Figure 37:
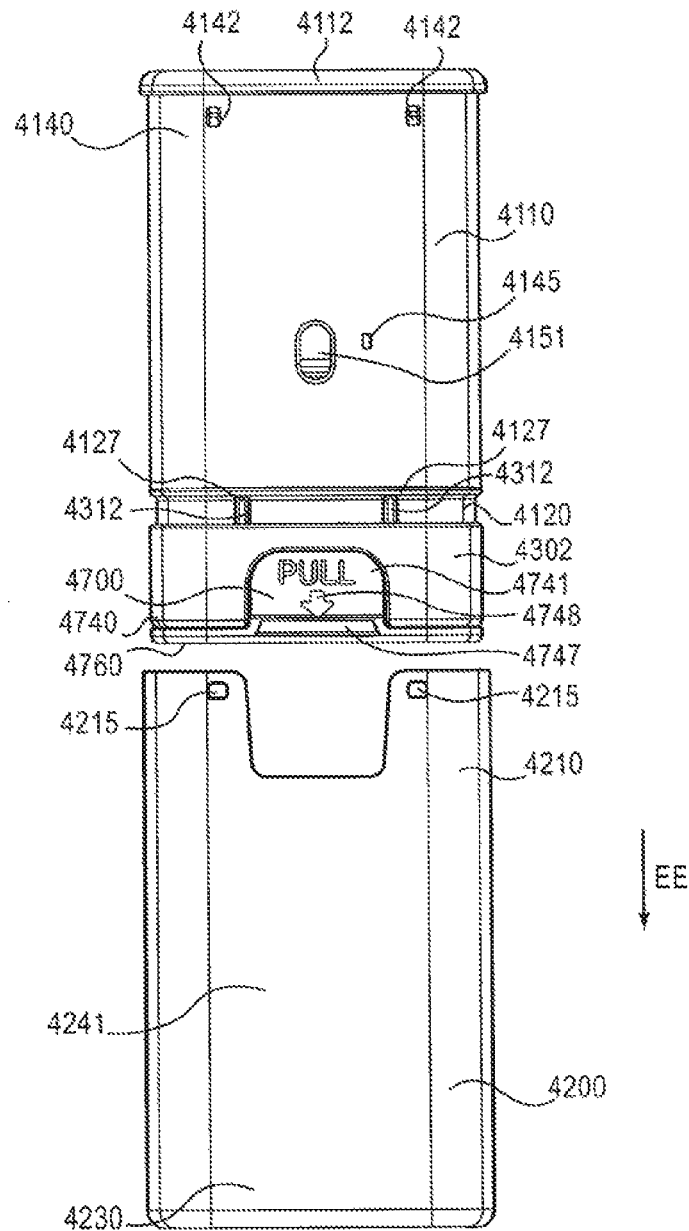
FIG. 37 is a back view of the medical injector illustrated in FIG. 4 in a second configuration.
Figure 38:
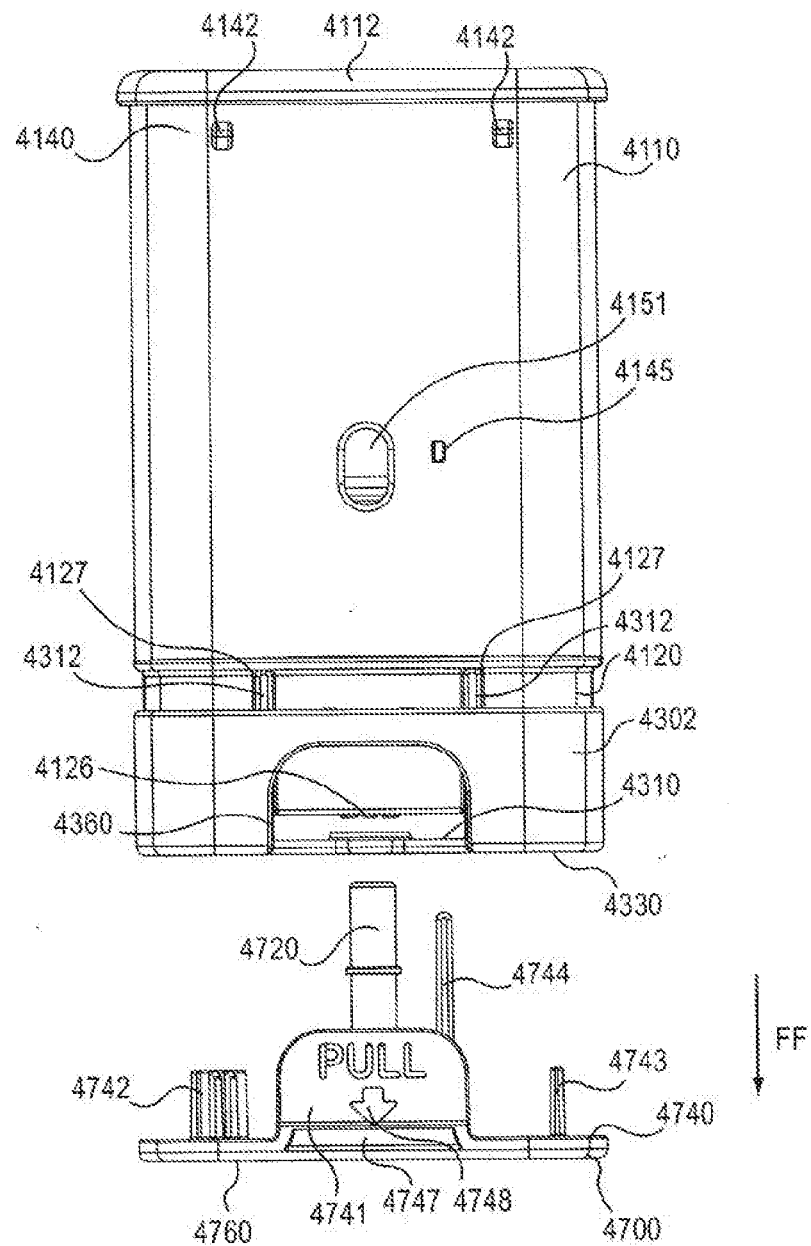
FIG. 38 is a back view of the medical injector illustrated in FIG. 4 in a third configuration.

As shown in FIG. 37, the medical injector 4000 is first enabled by moving the medicament delivery device 4000 from a first configuration to a second configuration by moving the cover 4200 from a first position to a second position. The cover 4200 is moved from the first position to the second position by moving it with respect to the housing 4110 in the direction shown by the arrow EE in FIG. 37. When the cover 4200 is moved with respect to the housing 4110 in the direction EE, the battery isolation protrusion 4235 is removed from the area between the battery clip 4910 and the second surface 4966 of the battery assembly 4962. In this manner, the battery assembly 4962 can be operatively coupled to the electronic circuit system 4900 when the cover 4200 is removed, thereby providing power to the electronic circuit system 4900. Similarly stated, this arrangement allows the electronic circuit system 4900 to be actuated when the cover 4200 is removed.

When power is provided, as described above, the electronic circuit system 4900 can output one or more predetermined electronic outputs. For example, in some embodiments, the electronic circuit system 4900 can output an electronic signal associated with recorded speech to the audible output device 4956. Such an electronic signal can be, for example, associated with a .WAV file that contains a recorded instruction instructing the user in the operation of the medical injector 4000. Such an instruction can state, for example, "remove the safety tab near the base of the auto-injector." The electronic circuit system 4900 can simultaneously output an electronic signal to one and/or both of the LEDs 4958A, 4958B thereby causing one and/or both of the LEDs 4958A, 4958B to flash a particular color. In this manner, the electronic circuit system 4900 can provide both audible and visual instructions to assist the user in the initial operation of the medical injector 4000.

In other embodiments, the electronic circuit system 4900 can output an electronic output associated with a description and/or status of the medical injector 4000 and/or the naloxone composition 4420 contained therein. For example, in some embodiments, the electronic circuit system 4900 can output an audible message indicating the symptoms for which the naloxone composition should be administered, the expiration date of the naloxone composition, the dosage of the naloxone composition or the like.

As described above, the medical injector 4000 can be can be repeatedly moved between the first configuration and the second configuration when the cover 4200 is moved repeatedly between the first position and the second position respectively. Said another way, the cover 4200 can be removed and replaced about the housing 4110 any number of times. When the cover 4200 is moved from the second position to the first position, the battery isolation protrusion 4235 is inserted between the battery clip 4910 and the second surface 4966 of the battery assembly 4962, deactivating the electronic circuit system 4900. When the cover is moved from the first position to the second position a second time, the electronic circuit system 4900 is once again activated. In this manner, the cover 4200 can be removed and the electronic circuit system 4900 can output an electronic output without compromising the sterility of the needle 4452.

After the cover 4200 is removed from the housing 4110, the medical injector 4000 can be moved from the second configuration to a third configuration by moving the safety lock 4700 from a first position to a second position. The safety lock 4700 is moved from a first position to a second position by moving the safety lock 4700 with respect to the housing 4110 in the direction shown by the arrow FF in FIG. 38. When the safety lock 4700 is moved from the first position to the second position, the safety lock protrusion 4742 is removed from between the extensions 4343 of the release member 4340, thereby enabling the medicament delivery member 4500. Moreover, as shown in FIGS. 26 and 27, when the safety lock 4700 is moved from the housing 4110, the actuator 4744 of the safety lock 4700 moves in the direction CC as shown in FIG. 27, irreversibly moving the first switch 4972 from a first state (e.g., a state of electrical continuity) to a second state (e.g., a state of electrical discontinuity). When the actuator 4744 of the safety lock 4700 moves irreversibly the first switch 4972 of the electronic circuit system 4900 to the second state, the electronic circuit system 4900 can output one or more predetermined electronic outputs. For example, in some embodiments, a processor (not shown) can output an electronic signal associated with recorded speech to the audible output device 4956. Such an electronic signal can be, for example, associated with a recorded message notifying the user of the status of the medical injector 4000. Such a status message can state, for example, "If ready to use the naloxone medical injector, pull off the red safety guard." The electronic circuit system 4900 can also simultaneously output an electronic signal to one and/or both of the LEDs 4958A, 4958B, thereby causing one and/or both of the LEDs 4958A, 4958B to stop flashing, change color or the like.

In some embodiments, the first actuation portion 4926 and the actuator 4744 can be configured such that the actuator 4744 must move a predetermined distance before the actuator 4744 engages the boundary 4929 of the opening 4928. For example, in some embodiments, the actuator 4744 must move approximately 0.200 inches before the actuator 4744 engages the boundary 4929 of the opening 4928. In this manner, the safety lock 4700 can be moved slightly without irreversibly moving the first switch 4972 of the electronic circuit system 4900 to the second state. Accordingly, this arrangement will permit the user to inadvertently and/or accidentally move the safety lock 4700 without actuating the electronic circuit system 4900.

In some embodiments, the electronic circuit system 4900 can be configured to output the status message for a predetermined time period, such as, for example, five seconds. After the predetermined time period has elapsed, the electronic circuit system 4900 can output an audible message further instructing the user in the operation of the medical injector 4000. Such an instruction can state, for example, "Place the base of the auto-injector against the patient's thigh. To complete the injection, press the base firmly against the patient's thigh." In some embodiments, the electronic circuit system 4900 can simultaneously output an electronic signal to one and/or both of the LEDs 4958A, 4958B, thereby causing one and/or both of the LEDs 4958A, 4958B to flash a particular color. In this manner, the electronic circuit system 4900 can provide both audible and/or visual instructions to assist the user in the placement and actuation of the medical injector 4000. In some embodiments, the electronic circuit system 4900 can be configured to repeat the instructions after a predetermined time period has elapsed.

As described above, in other embodiments, the medical injector 4000 can have a network interface device (not shown) configured to operatively connect the electronic circuit system 4900 to a remote device (not shown) and/or a communications network (not shown). In this manner, the electronic circuit system 4900 can send a wireless signal notifying a remote device that the safety lock 4700 of the medical injector 4000 has been removed and that the medical injector 4000 has been armed. In other embodiments, the electronic circuit system 4900 can send a wireless signal (e.g., a wireless 911 call) notifying an emergency responder that the medical injector 4000 has been armed.

After the safety lock 4700 is moved from the first position to the second position, the medical injector 4000 can be moved from the third configuration to a fourth configuration by moving the base 4302 from a first position to a second position. Similarly stated, the medical injector 4000 can be actuated by the system actuator assembly 4300 by moving the base 4302 distally relative to the housing 4110. The base 4302 is moved from its first position to its second position by placing the medical injector 4000 against the body of the patient and moving the base 4302 with respect to the housing 4110 in the direction shown by the arrow GG in FIG. 39. Moving the base 4302 from the first position to the second position causes the protrusions 4313 on the proximal surface 4310 of the base 4302 to engage the tapered surfaces 4349 of the extensions 4343 of the release member 4340, thereby moving the extensions 4313 together. The inward movement of the extensions 4343 causes the release member 4340 to become disengaged from the distal end portion of the housing 4110, thereby allowing the release member 4340 to be moved proximally along its longitudinal axis as the spring 4370 expands.

Figure 39:
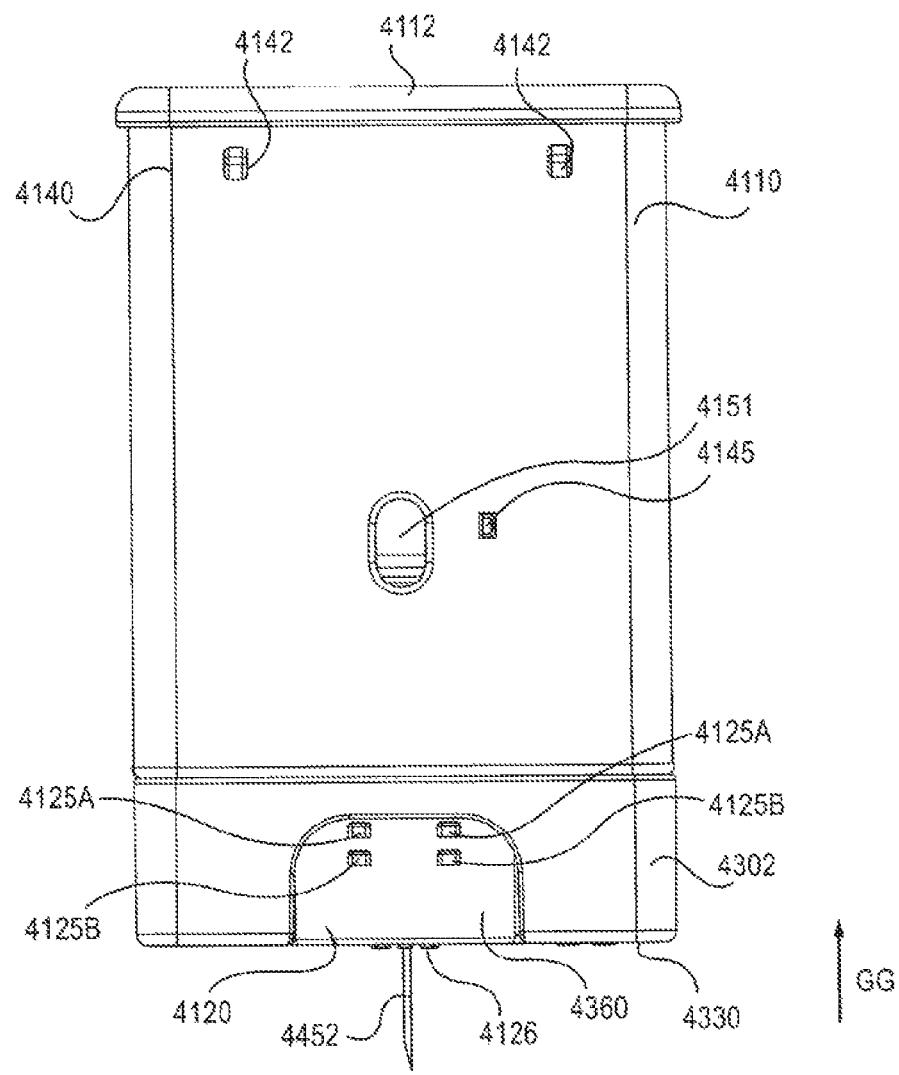
FIG. 39 is a back view of the medical injector illustrated in FIG. 4 in a fourth configuration (i.e., the needle insertion configuration).
Figure 40:
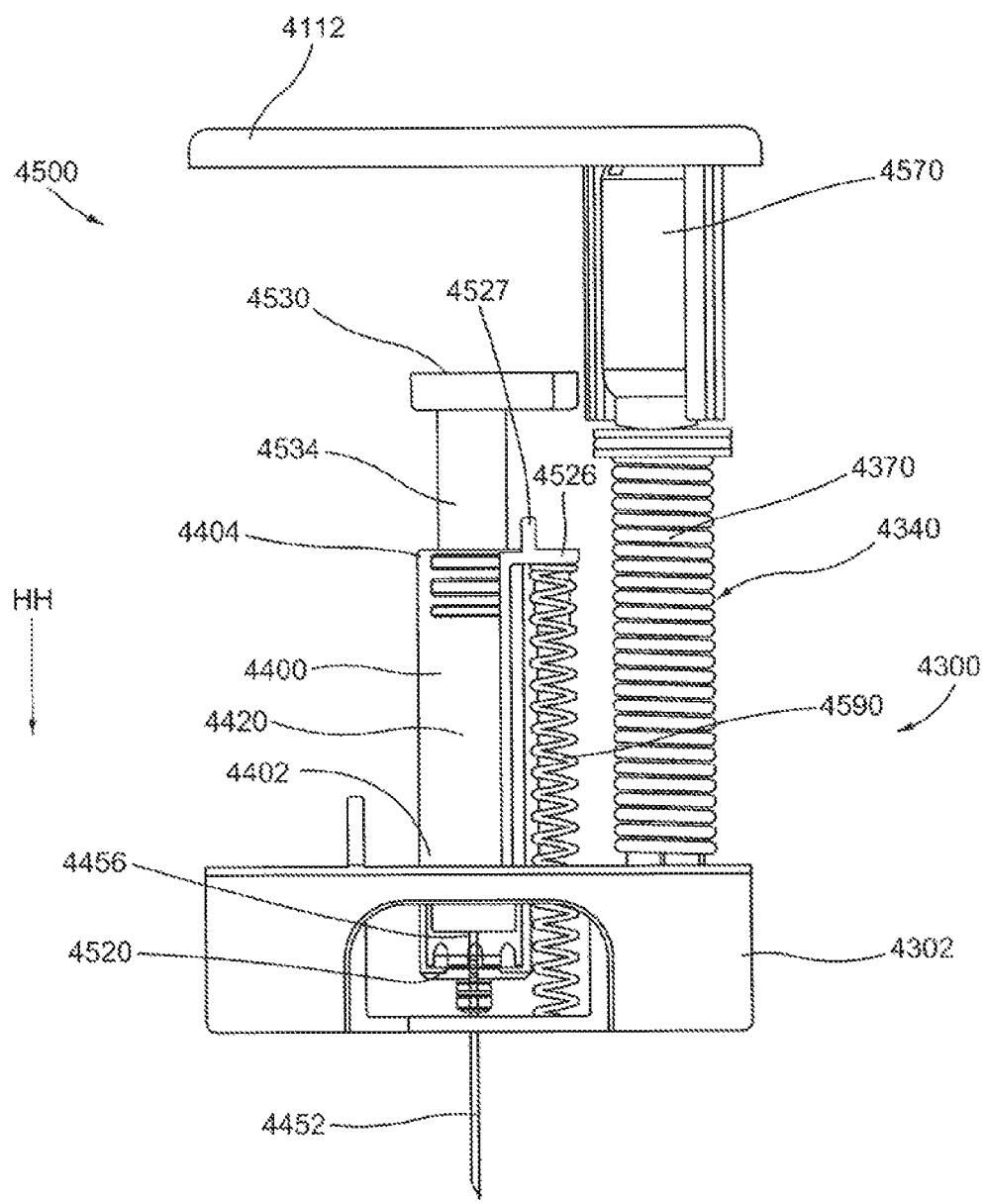
FIG. 40 is a front view of the medical injector illustrated in FIG. 4 in the fourth configuration (i.e., the needle insertion configuration).

When the base 4302 is moved from the first position to the second position, the system actuator 4300 actuates the medicament delivery mechanism 4500, thereby placing the medical injector 4500 in its fourth configuration (i.e., the needle insertion configuration), as shown in FIGS. 39 and 40. More particularly, when the medical injector is in its fourth configuration, the puncturer 4341 of the release member 4340 is in contact with and/or disposed through the frangible seal 4573 of the gas container 4570.

After the frangible seal 4573 has been punctured, an actuating portion of a compressed gas can escape from the gas container 4570 and flow via the gas passageway 4144 into the medicament cavity 4157. The gas applies gas pressure to the movable member 4530 causing the movable member 4530 and the carrier 4520 to move in a distal direction within the medicament cavity 4157, as shown by the arrow HH in FIG. 40. When the carrier 4520 moves distally within the medicament cavity 4157, the carrier 4520 and the medicament container 4400 are in a first configuration. Accordingly, as described above, the medicament container 4400 is connected to the carrier 4520 by a "snap fit" connection. In this manner, the medicament container 4400 and the needle 4452 contemporaneously move with movable member 4530 and/or the carrier 4520 in a distal direction. As described above, the proximal end portion 4456 of the needle 4452 is connected to the distal end portion 4522 of the carrier 4520 and is spaced from the seal 4406 of the medicament container 4400 when the carrier 4520 is in its first configuration. Said another way, the medicament container 4400 and the needle 4452 do not define a medicament delivery path when the carrier 4520 is in the first configuration. The movement of the needle 4452 in a distal direction causes the distal end portion of the needle 4452 to exit the housing 4110 and enter the body of a patient prior to administering the naloxone composition 4420.

After the carrier 4520 and/or the needle 4452 have moved within the medicament cavity 4157 a predetermined distance, the carrier 4520 and the medicament container 4400 are moved from the first configuration to a second configuration. In the second configuration of the carrier 4520, the medicament container 4400 is released from the "snap-fit" allowing the medicament container 4400 and the movable member 4530 to continue to move in a distal direction relative to the carrier 4520. Said another way, the medicament container 4400 is configured to slidably move within the carrier 4520 when the carrier is moved from the first configuration to the second configuration. As the medicament container 4400 continues to move within the carrier 4520, the proximal end portion 4456 of the needle 4452 contacts and punctures the seal 4406 of the medicament container 4400. This allows the medicament contained in the medicament container 4400 to flow into the lumen (not shown) defined by the needle 4452, thereby defining a medicament delivery path.

After the medicament container 4400 contacts the distal end of the carrier 4520, the medicament container 4400 stops moving within the carrier 4520 while the movable member 4530 continues to move in a distal direction, as shown by the arrow II in FIG. 41. This causes the piston portion 4534 of the movable member 4530 to move within the medicament container 4400 containing the naloxone composition 4420. As the piston portion 4534 of the movable member 4530 moves within the medicament container 4400, the piston portion 4534 contacts the elastomeric member 4410 and generates a pressure upon the naloxone composition 4420 contained within the medicament container 4400, thereby allowing at least a portion of the naloxone composition 4420 to flow out of the medicament container 4400 and into the lumen defined by the needle 4452. The medicament is delivered to a body of a user via the medicament delivery path defined by the medicament container 4400 and the needle 4452.

Figure 42:
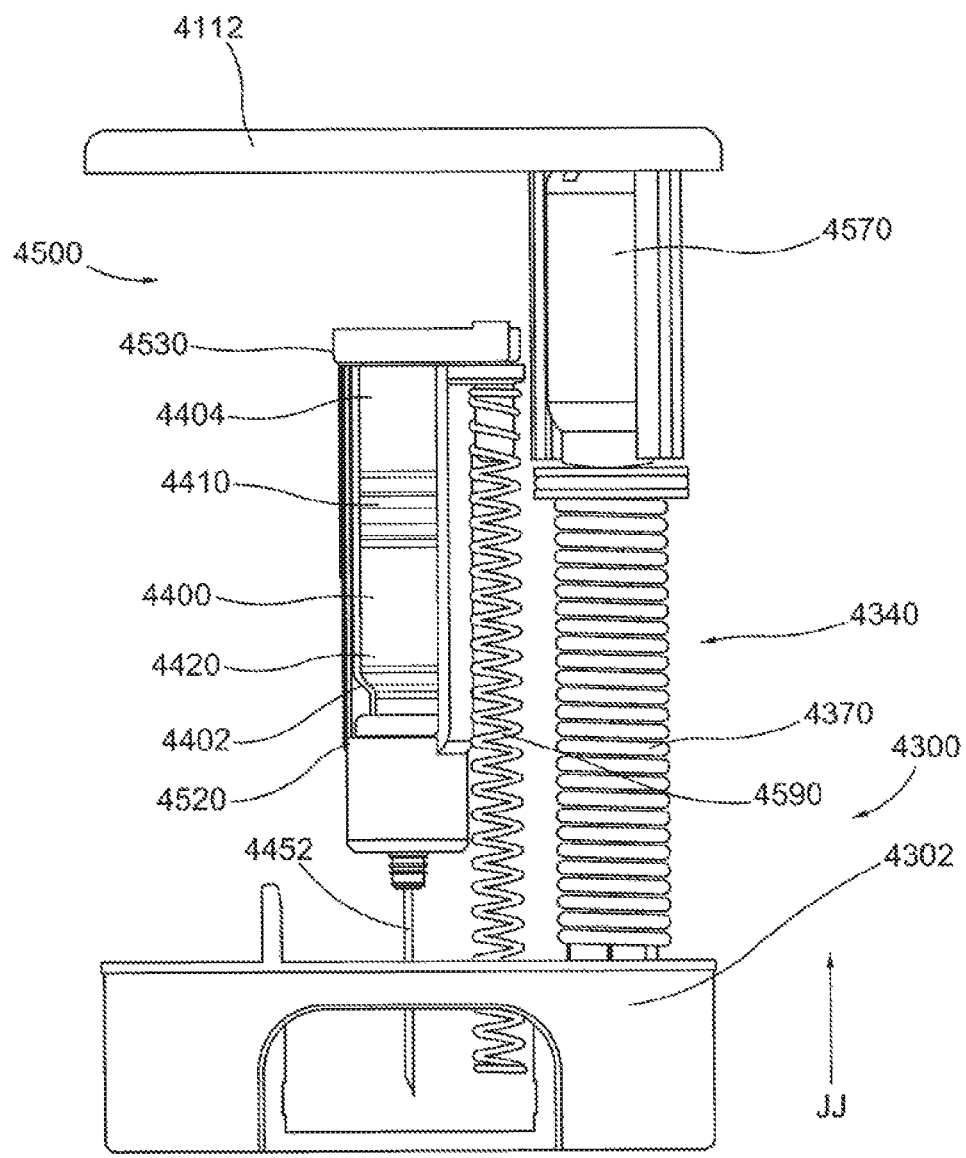
FIG. 42 is a front view of the medical injector illustrated in FIG. 4 in a sixth configuration (i.e., the retraction configuration).

As shown in FIG. 42, after the movable member 4530 moves a predetermined distance within the medicament container 4400, the gas valve actuator 4527 of the carrier 4520 engages the gas relief valve (not shown in FIG. 42) of the movable member 4530 thereby allowing the pressurized gas contained within the gas chamber (i.e., the volume within the medicament cavity 4157 between the proximal end of the housing 4110 and the proximal end of the movable member 5530) to escape. Similarly stated, the gas valve actuator 4527 of the carrier 4520 engages the gas relief valve of the movable member 4530, the pressure within the housing 4110 is reduced, thereby ending the injection event. In this manner, the pre-injection distance between the proximal end portion of the movable member 4530 and the gas valve actuator 4527 of the carrier 4520 can be adjusted to control the amount of the naloxone composition 4420 to be injected. After the gas pressure within the medicament cavity 4157 decreases below a certain level, the force exerted by the retraction spring 4590 on the carrier 4520 can be sufficient to cause the carrier 4520 to move proximally within the housing 4110 (i.e., to retract), as shown by the arrow JJ in FIG. 42.

As described above, the actuator 4311 of the base 4302 actuates the electronic circuit 4900 to trigger a predetermined output or sequence of outputs when the base 4302 is moved from its first position to its second position (see, e.g., FIGS. 24-28). When the actuator 4311 is moved in a proximal direction relative to the opening 4945, as shown by the arrow DD in FIG. 28, the electronic circuit system 4900 is actuated to output one or more predetermined electronic outputs. For example, in some embodiments, the electronic circuit system 4900 can output an electronic signal associated with recorded speech to the audible output device 4956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 4000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 4900 can also simultaneously output an electronic signal to one and/or both LEDs 4958A, 4958B, thereby causing one and/or both LEDs 4958A, 4958B to stop flashing, change color or the like, to provide a visual indication that the injection is complete. In other embodiments, the electronic circuit system 4900 can send a wireless signal notifying a remote device that the injection is complete. In this manner, a patient's compliance can be monitored.

In some embodiments, the second actuation portion 4946 and the actuator 4311 can be configured such that the base 4500 and/or the actuator 4311 must move a predetermined distance before the actuator 4311 engages the boundary 4949 of the opening 4945. For example, in some embodiments, the actuator 4311 must move approximately 0.200 inches before the actuator 4311 engages the boundary 4949 of the opening 4945. In this manner, the base 4700 can be moved slightly without irreversibly moving the second switch 4973 of the electronic circuit system 4900 to the second state. Accordingly, this arrangement will permit the user to inadvertently and/or accidentally move the base 4500 without actuating the electronic circuit system 4900.

Although the electronic circuit system 4900 is shown and described above as having two irreversible switches (e.g., switch 4972 and switch 4973), in other embodiments, an electronic circuit system can have any number of switches. Moreover, such switches can be either reversible or irreversible. For example, FIGS. 43-48 show portions of a medicament delivery device 5000 having an electronic circuit system 5900 having three irreversible switches.

Figure 43:
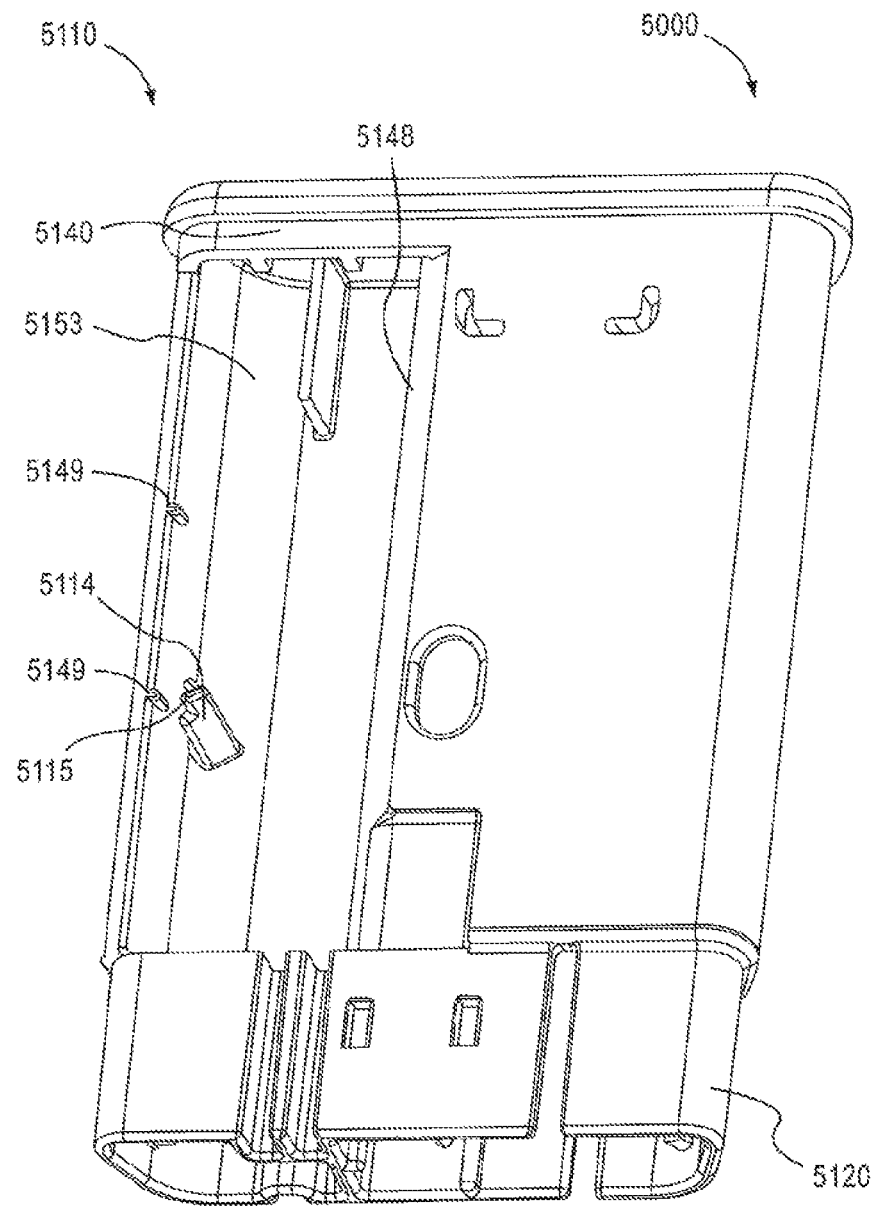
FIG. 43 is a perspective view of a housing of a medical injector according to an embodiment.
Figure 44:
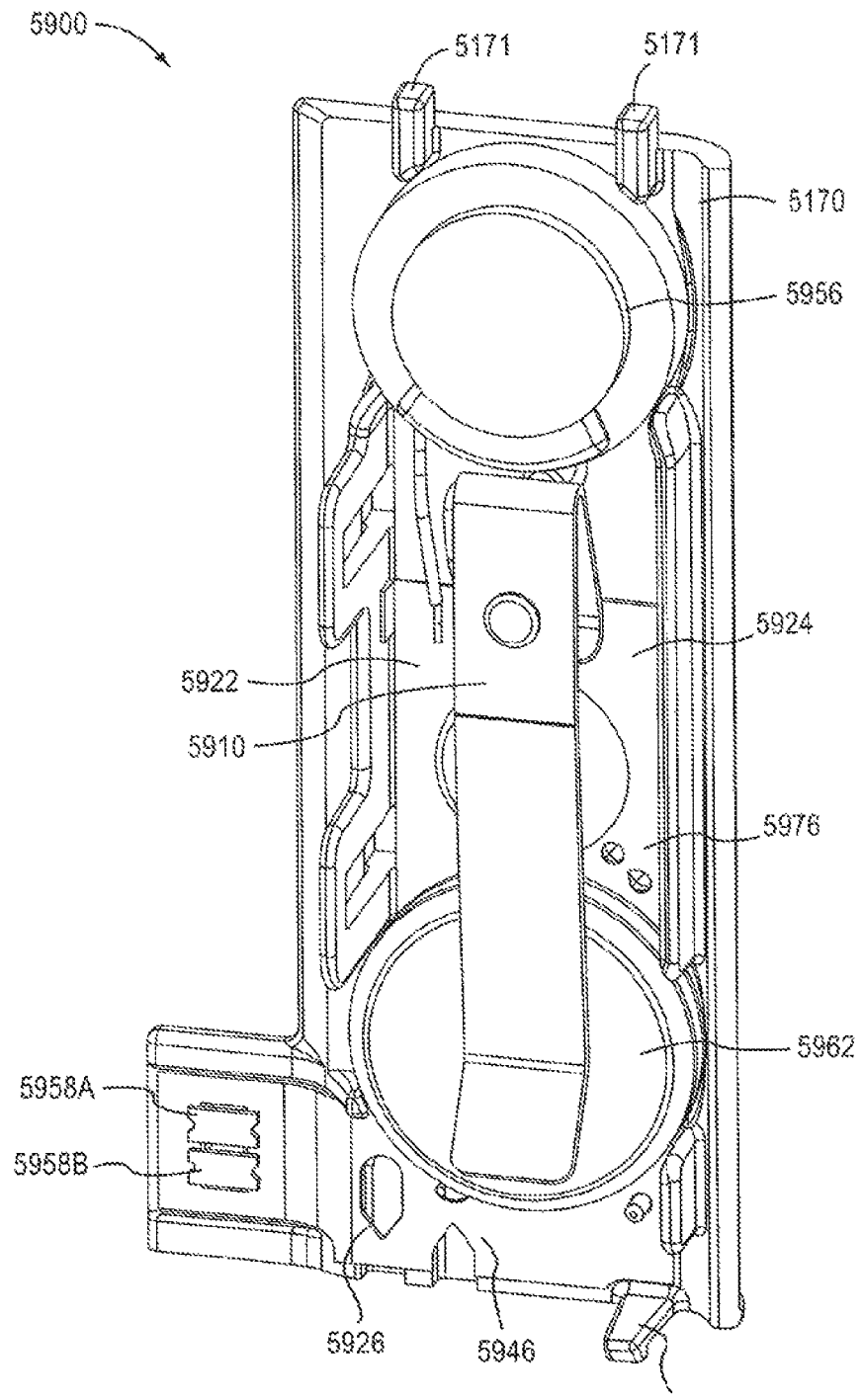
FIG. 44 is a perspective view of an electronic circuit system of a medical injector according to an embodiment.

The medicament delivery device 5000 is similar to the medical injector 4000 described above. As shown in FIGS. 43 and 44 (which show only portions of the medicament delivery device 5000), the medicament delivery device 5000 includes a housing 5110, a delivery mechanism (not shown), an electronic circuit system 5900, a cover (not shown), a safety lock (not shown, similar to safety lock 4700) and a base (not shown, similar to base 4302). The structure and operation of the delivery mechanism, the cover, the safety lock and the base are similar to the structure and operation of the delivery mechanism 4500, the cover 4200, the safety lock 4700 and the base 4302, respectively. Accordingly, only the electronic circuit system 5900 and the housing 5110 are described in detail below.

As shown in FIG. 43, the housing 5110 has a proximal end portion 5140 and a distal end portion 5120. The housing 5110 defines a gas cavity (not shown), a medicament cavity (not shown) and an electronic circuit system cavity 5153. The gas cavity and medicament cavity of the housing 5110 of the medicament delivery device 5000 are similar to the gas cavity 4154 and the medicament cavity 4157, shown and described above with reference to FIGS. 10 and 11.

The electronic circuit system cavity 5153 is configured to receive the electronic circuit system 5900. As described above, the electronic circuit system cavity 5153 is fluidically and/or physically isolated from the gas cavity and/or the medicament cavity by a sidewall 5148. The housing 5110 has protrusions 5149 configured to stabilize the electronic circuit system 5900 when the electronic circuit system 5900 is disposed within the electronic circuit system cavity 5153. The housing 5110 also defines connection apertures (not shown) configured to receive connection protrusions 5171 of the electronic circuit system 5900 (see e.g., FIG. 44). In this manner, the electronic circuit system 5900 can be coupled to the housing 5110 within the electronic circuit system cavity 5153 (see e.g., FIG. 47). In other embodiments, the electronic circuit system 5900 can be coupled within the electronic circuit system cavity 5153 by any other suitable means, such as an adhesive, a clip and/or the like.

The housing 5110 includes an actuation protrusion 5114 disposed within the electronic circuit system cavity 5153. As described in more detail herein, an angled end portion 5115 of the actuation protrusion 5114 of the housing 5110 is configured to engage a third actuation portion 5976 of a substrate 5924 of the electronic circuit system 5900 when the electronic circuit system 5900 is coupled to the housing 5110.

Figure 47:
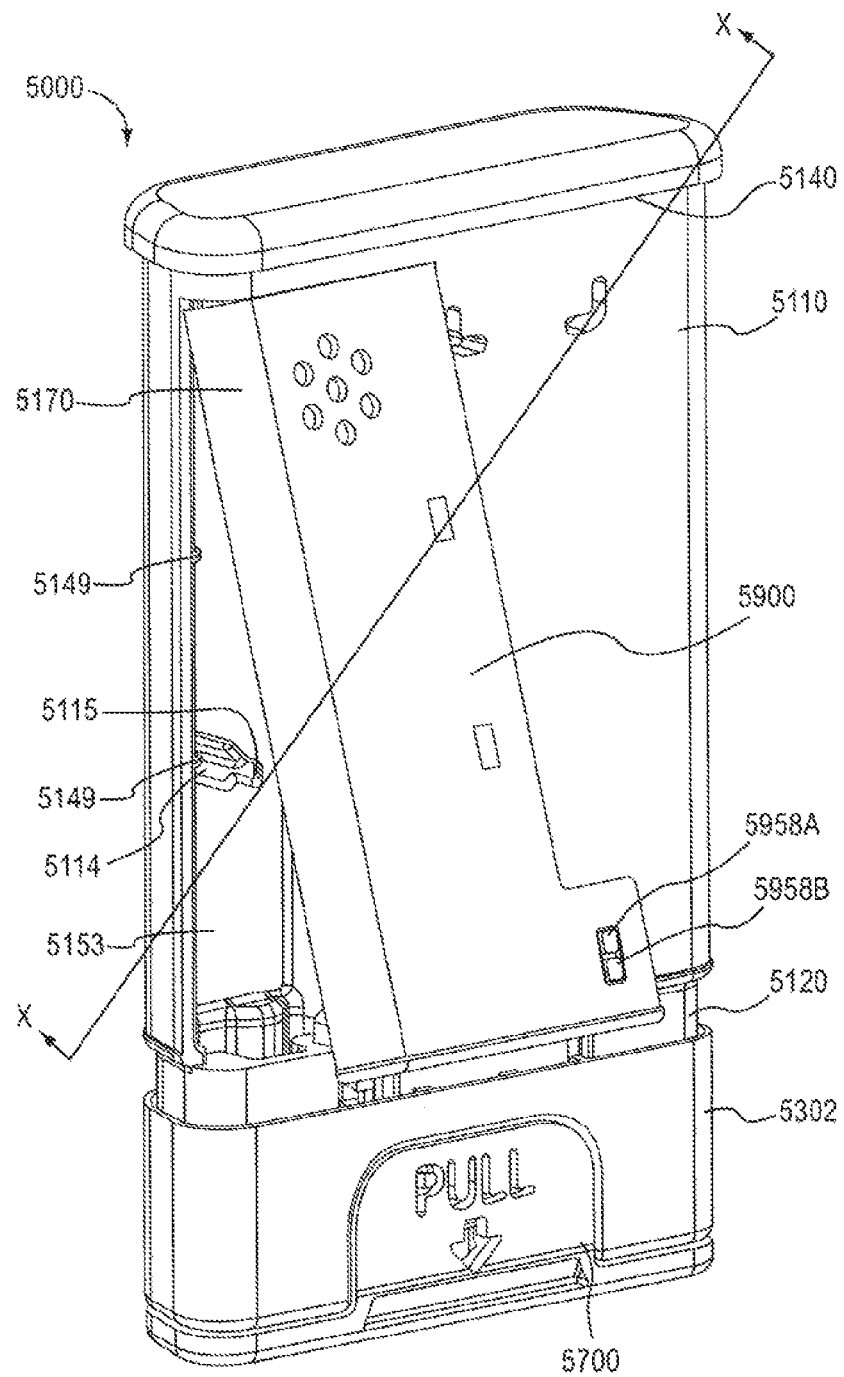
FIG. 47 is a perspective cross-sectional view of the housing and the electronic circuit system illustrated in FIG. 43 and FIG. 44 respectively.

As shown in FIG. 47, the electronic circuit system 5900 is configured to fit within the electronic circuit system cavity 5153 of the housing 5110. Accordingly, as described above, the electronic circuit system 5900 is physically and/or fluidically isolated from the medicament cavity, the gas cavity and/or the medicament delivery path within the medicament delivery device 5000 (not shown). As described herein, the electronic circuit system 5900 is configured to output an electronic output associated with a use of the medicament delivery device 5000.

As shown in FIG. 44, the electronic circuit system 5900 is similar to the electronic circuit system 4900 described above. The electronic circuit system 5900 of the medicament delivery device 5000 includes an electronic circuit system housing 5170, a printed circuit board 5922, a battery assembly 5962, an audio output device 5956, two light emitting diodes (LEDs) 5958A, 5958B and a battery clip 5910. The electronic circuit system housing 5170, the battery assembly 5962, the audio output device 5956, the two light emitting diodes (LEDs) 5958A, 5958B and the battery clip 5910 are similar to the electronic circuit system housing 4170, the battery assembly 4962, the audio output device 4956, the two light emitting diodes (LEDs) 4958A, 4958B and the battery clip 4910 of the electronic circuit system 4900 described above. Thus, a detailed discussion of these components is omitted.

The electronic circuit system 5900 also includes a processor 5950 configured to process electronic inputs (e.g., from input switches) and produce electronic outputs. As described herein, such electronic outputs can include audio or visual outputs associated with a use of the medicament delivery device 5000. The processor 5950 can be a commercially-available processing device dedicated to performing one or more specific tasks. For example, in some embodiments, the processor 5950 can be a commercially-available microprocessor, such as the Sonix SNC 12060 or the SNC 26120 voice synthesizers. Alternatively, the processor 5950 can be an application-specific integrated circuit (ASIC) or a combination of ASICs, which are designed to perform one or more specific functions. In yet other embodiments, the processor 5950 can be an analog or digital circuit, or a combination of multiple circuits.

The processor 5950 can include a memory device (not shown) configured to receive and store information, such as a series of instructions, processor-readable code, a digitized signal, or the like. The memory device can include one or more types of memory. For example, the memory device can include a read only memory (ROM) component and a random access memory (RAM) component. The memory device can also include other types of memory suitable for storing data in a form retrievable by the processor 5950, for example, electronically-programmable read only memory (EPROM), erasable electronically-programmable read only memory (EEPROM), or flash memory.

Figure 45:
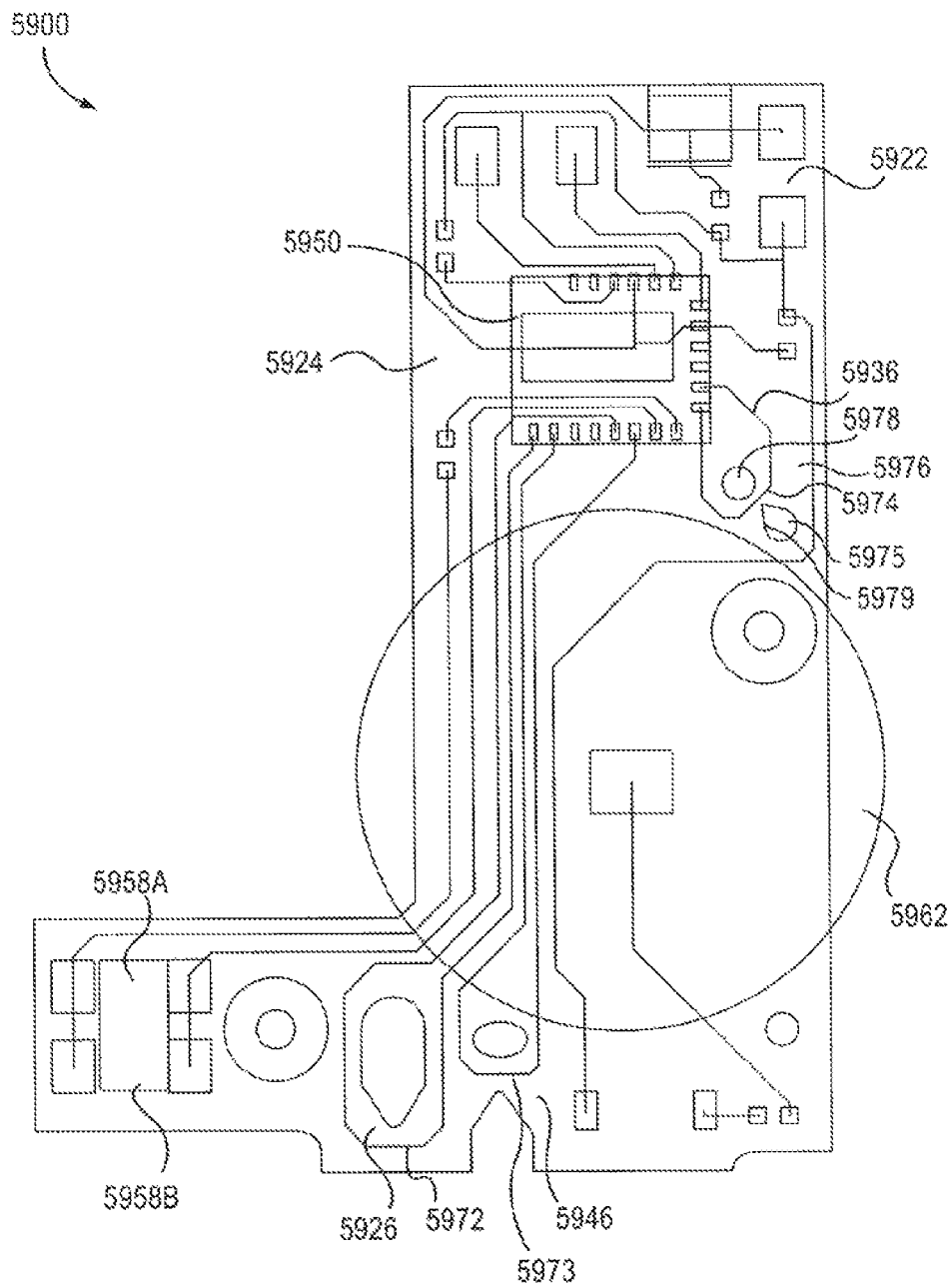
FIG. 45 is a back view of a printed circuit board of the electronic circuit system shown in FIG. 44.
Figure 46:
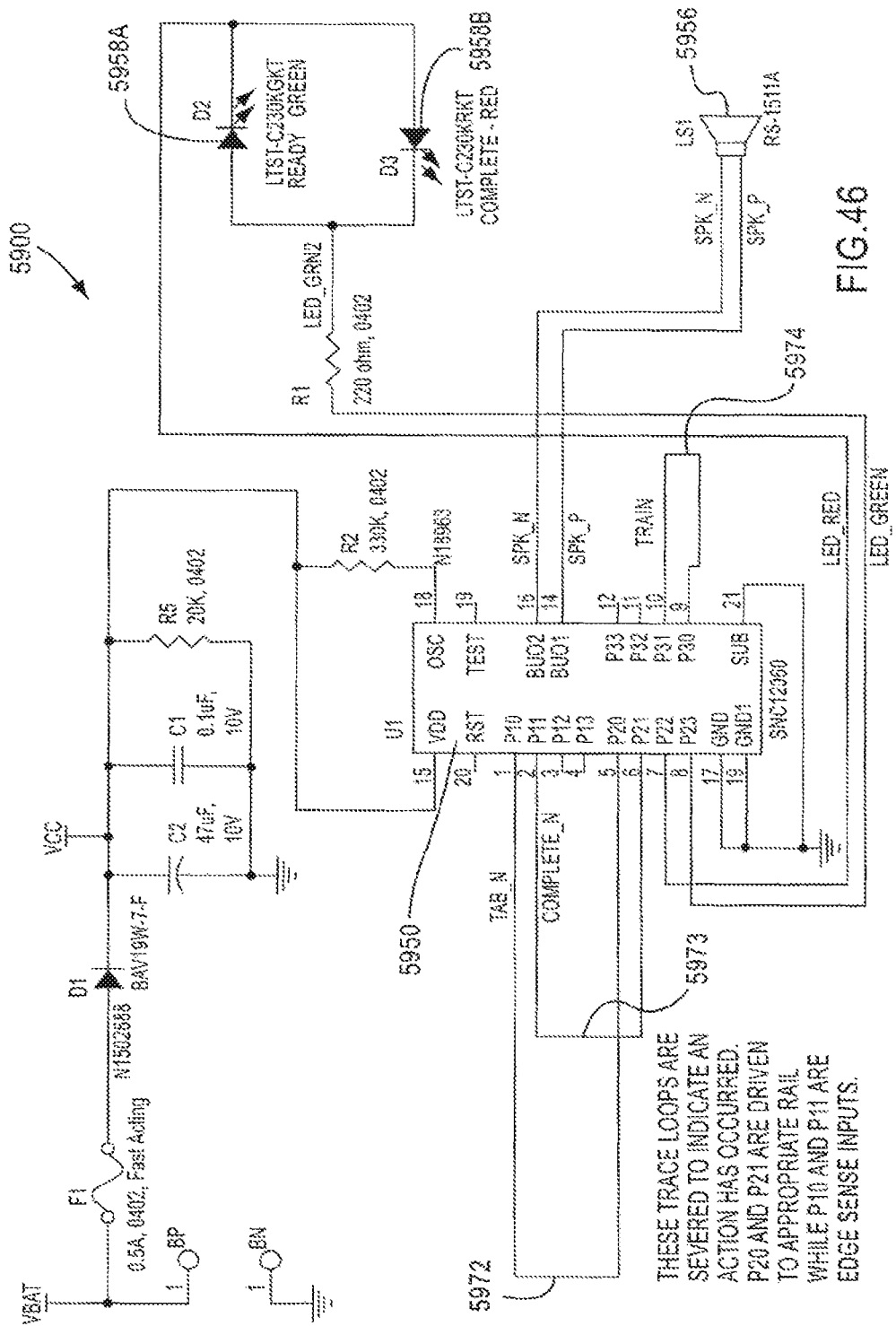
FIG. 46 is a schematic illustration of the electronic circuit system shown in FIG. 44.

FIG. 45 shows the printed circuit board 5922 of the electronic circuit system 5900. FIG. 46 is a schematic illustration of the electronic circuit system 5900. The printed circuit board 5922 of the electronic circuit system 5900 includes a substrate 5924, a first actuation portion 5926 (including a first switch 5972), a second actuation portion 5946 (including a second switch 5973), and a third actuation portion 5976 (including an electronic circuit system configuration switch 5974). The substrate 5924 of the printed circuit board 5922 includes the electrical components necessary for the electronic circuit system 5900 to operate as desired. For example, the electrical components can include resistors, capacitors, inductors, switches, microcontrollers, microprocessors and/or the like.

Figure 48:
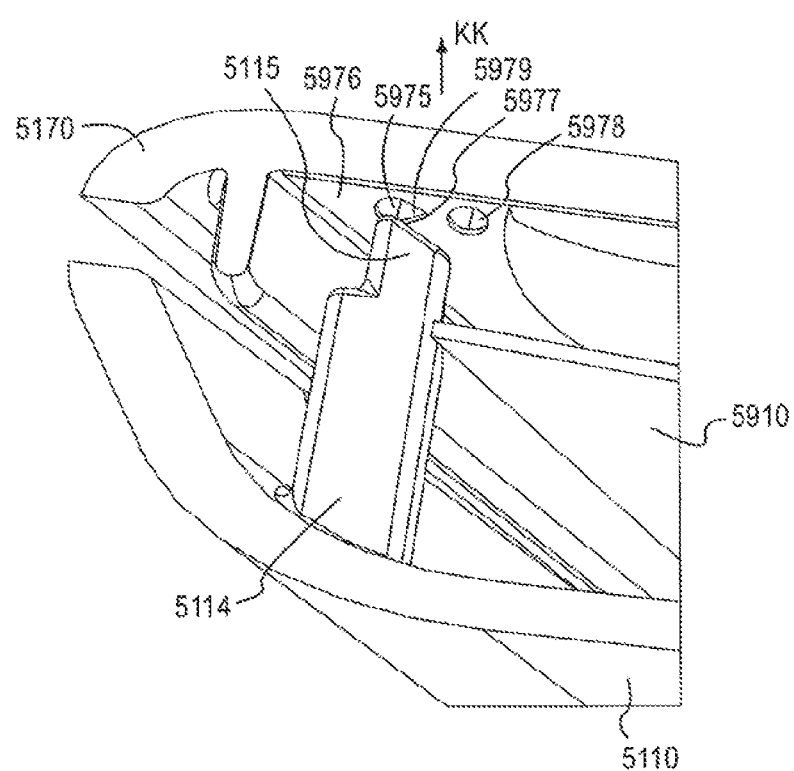
FIG. 48 is a cross-sectional perspective view of a portion of the electronic circuit system illustrated in FIG. 36, taken along line X-X in FIG. 47.

The first actuation portion 5926 and the second actuation portion 5946 are similar to the first actuation portion 4926 and the second actuation portion 4946 of the electronic circuit system 4900, described above (see e.g., FIG. 44), and are therefore not described or labeled in detail. The third actuation portion 5976 includes a third electrical conductor 5936 (see e.g., FIG. 45) and defines an actuation aperture 5975 having a boundary 5979, and a tear propagation limit aperture 5978. As shown in FIGS. 44 and 48, the actuation aperture 5975 of the third actuation portion 5976 is configured to receive the angled end portion 5115 of the actuation protrusion 5114 of the housing 5110 when the electronic circuit system 5900 is disposed within the electronic circuit system cavity 5153. The boundary 5979 of the actuation aperture 5975 has a discontinuous shape, such as, for example, a teardrop shape, that includes a stress concentration riser 5977. The discontinuity and/or the stress concentration riser 5977 of the boundary 5979 can be of any suitable shape to cause the substrate 5924 to deform in a predetermined direction when the angled end portion 5115 of the actuation protrusion 5114 of the housing 5110 is inserted into the actuation aperture 5975 (see e.g., FIG. 48), as described below.

The third electrical conductor 5936 includes the electronic circuit system configuration switch 5974 (see e.g., FIG. 45) disposed between the actuation aperture 5975 and the tear propagation limit aperture 5978, which can be, for example, a frangible portion of the third electrical conductor 5436. As shown in FIGS. 47 and 48, when the electronic circuit system 5900 is attached to the housing 5110, a portion of the angled portion 5115 of the actuation protrusion 5114 is disposed within the actuation aperture 5975 of the third actuation portion 5976, as shown by the arrow KK in FIG. 48. Continued movement of the angled portion 5115 of the actuation protrusion 5114 within the third actuation portion 5976 of the substrate 5924 causes the third actuation portion 5976 of the substrate 5924 to tear, thereby separating the portion of the third electrical conductor 5936 including the electronic circuit system configuration switch 5974. Said another way, when the electronic circuit system 5900 is attached to the housing 5110, the actuation protrusion 5114 moves irreversibly the electronic circuit system configuration switch 5974 from a first state (e.g., a state of electrical continuity) to a second state (e.g., a state of electrical discontinuity).

The tear propagation limit aperture 5978 is configured to limit the propagation of the tear in the substrate 5924. Said another way, the tear propagation limit aperture 5978 is configured to ensure that the tear in the substrate 5924 does not extend beyond the tear propagation limit aperture 5978. The tear propagation limit aperture 5978 can be any shape configured to limit the propagation of a tear and/or disruption of the substrate 5924. For example, the tear propagation limit aperture 5978 can be oval shaped. In other embodiments, the boundary of the tear propagation limit aperture 5978 can be reinforced to ensure that the tear in the substrate 5924 does not extend beyond the tear propagation limit aperture 5978. The angled end portion 5115 of the actuation protrusion 5114 ensures that the tear in the substrate 5924 propagates in the desired direction. Said another way, the angled end portion 5115 of the actuation protrusion 5114 ensures that the tear in the substrate 5924 occurs between the actuation aperture 5975 and the tear propagation limit aperture 5978.

When the actuation protrusion 5114 of the housing 5110 moves irreversibly the electronic circuit system configuration switch 5974 of the electronic circuit system 5900 from the first state to the second state, the electronic circuit system 5900 can be moved between a first configuration and a second configuration. For example, in some embodiments, irreversibly moving the electronic circuit system configuration switch 5974 of the electronic circuit system 5900 to the second state places the electronic circuit system 5900 in the second configuration such that when power is applied to the electronic circuit system 5900, the electronic circuit system 5900 recognizes that the medicament delivery device 5000 is a certain type of medicament delivery device and/or is in a certain configuration. In some embodiments, the housing can be devoid of the actuation protrusion 5114, thus the electronic circuit system configuration switch 5974 is maintained in its first state when the electronic circuit system 5900 is attached to the housing 5110. In this manner, the electronic circuit system configuration switch 5974 can enable the electronic circuit system 5900 to be used in different types and/or configurations of medicament delivery devices. The dual functionality of the electronic circuit system 5900 enables production of the same electronic circuit system 5900 for multiple devices, thereby permitting mass production and decreasing the cost of production of the electronic circuit system 5900.

For example, in some embodiments the electronic circuit system 5900 can be used in either an actual medicament delivery device or a simulated medicament delivery device. A simulated medicament delivery device can, for example, correspond to an actual medicament delivery device and can be used, for example, to train a user in the operation of the corresponding actual medicament delivery device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

The actuation of the medicament delivery device configuration switch 5974 can configure the electronic circuit system 5900 to output a different electronic output when the medicament delivery device 5000 is a simulated medical injector than when the medicament delivery device 5000 is an actual medical injector. Said yet another way, the electronic circuit system 5900 can be configured to output a first series of electronic outputs when the electronic circuit system configuration switch 5974 is in the first state and a second series of electronic outputs when the electronic circuit system configuration switch 5974 is in the second state. In this manner, the electronic circuit system configuration switch 5974 can enable the same electronic circuit system 5900 to be used in both simulated medicament delivery devices and actual medicament delivery devices. When used on an actual medicament delivery device, for example, the housing can be devoid of the actuation protrusion 5114. The dual functionality of the electronic circuit system 5900 can decrease the cost of production of the electronic circuit system 5900 of the medicament delivery device 5000.

In other embodiments, moving the electronic circuit system configuration switch 5974 to the second state can place the electronic circuit system 5900 in any number of different functional configurations. For example, moving the electronic circuit system configuration switch 5974 from the first state to the second state can indicate the type of medicament in the medicament container, the dosage of the medicament and/or the language of the audible electronic outputs output by the electronic circuit system 5900.

In still other embodiments, any number of electronic circuit system configuration switches can be used. For example, multiple switches can be used to configure the electronic circuit system 5900 to output usage instructions in any number of languages. For example, if an electronic circuit system contained three configuration switches (e.g., switches A, B and C), switch A can correspond to English instructions, switch B to Spanish instructions and switch C to German instructions. Further, moving both switch A and B to the second state might correspond to French instructions. In this manner, a single electronic circuit system 5900 can be configured to output instructions in multiple languages.

The needle 4452, as well as any other needles shown and described herein, can have any diameter and/or length to facilitate the injection of the naloxone composition 4420. For example, the needle can have a length suitable to penetrate clothing and deliver the naloxone via a subcutaneous injection and/or an intramuscular injection. In some embodiments, the needle 4452 (and any needle disclosed herein) can have a length of greater than 1 inch, greater than 1.5 inches, greater than 2 inches, greater than 2.5 inches or greater than 3 inches. In some embodiments, the needle 4452 (and any needle disclosed herein) can have a lumen diameter of approximately between 19 gauge and 31 gauge.

Although the medical injectors 4000 and 5000 are shown and described above as being auto-injectors configured to deliver the naloxone compositions described herein via injection through a needle (e.g., needle 4452), in other embodiments, a medicament delivery device can be configured to deliver the naloxone compositions described herein via any suitable delivery member, and in any suitable manner. For example, in some embodiments, a medicament delivery device can include a delivery member that delivers the naloxone composition into the body via inhalation and/or intranasal delivery.

Figure 49:
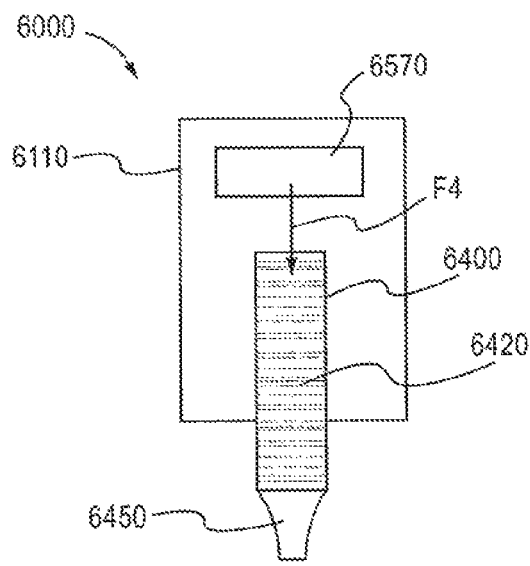
FIG. 49 is a schematic illustration of a medicament delivery device according to an embodiment.

For example, FIG. 49 is a schematic illustration of a medicament delivery device 6000 according to an embodiment that is configured to deliver a naloxone composition intranasally and/or via inhalation. The medicament delivery device 6000 includes a housing 6110, a medicament container 6400, a delivery member 6450 and an energy storage member 6570. The medicament container 6400 is at least partially disposed within the housing 6110, and contains (i.e., is filled or partially filled with) a naloxone composition 6420. The delivery member 6450 is coupled to the medicament container 6400, and, as described herein, is configured to delivery the naloxone composition from the medicament container 6400 intranasally and/or via inhalation. The energy storage member 6570 is disposed within the housing 6110, and is configured to produce a force F4 to deliver the naloxone composition 6420 (e.g., from the medicament container 6400 to a body).

The naloxone composition 6420 can be any of the naloxone compositions described herein. In particular, the naloxone composition 6420 can include an effective amount of naloxone or salts thereof, a tonicity-adjusting agent, and a pH adjusting agent. The naloxone composition 6420 can be formulated such that the osmolality of the naloxone composition 6420 ranges from about 250-350 mOsm and the pH ranges from about 3-5.

In some embodiments, the naloxone composition 6420 can include any suitable concentration of 4,5-epoxy-3,14-dihydroxy-17-(2-propenyl) morphinan-6-one. In some embodiments, for example, the naloxone composition 6420 has a concentration of 4,5-epoxy-3,14-dihydroxy-17-(2-propenyl)morphinan-6-one between approximately 0.01 mg/mL and approximately 60 mg/mL. In other embodiments, the naloxone composition 6420 has a concentration of 4,5-epoxy-3,14-dihydroxy-17-(2-propenyl)morphinan-6-one between approximately 0.05 mg/mL and approximately 2 mg/mL.

The tonicity-adjusting agent can be any of the tonicity-adjusting agents described herein, and can be included within the naloxone composition 6420 in any suitable amount and/or concentration. For example, in some embodiments, the tonicity-adjusting agent includes at least one of dextrose, glycerin, mannitol, potassium chloride or sodium chloride. In other embodiments, the tonicity-adjusting agent includes sodium chloride in an amount such that a concentration of sodium chloride is between approximately 0.1 mg/mL and approximately 20 mg/mL.

The pH adjusting agent can be any of the pH adjusting agents described herein, and can be included within the naloxone composition 6420 in any suitable amount and/or concentration. For example, in some embodiments, the pH adjusting agent includes at least one of hydrochloric acid, citric acid, citrate salts, acetic acid, acetate salts, phosphoric acid or phosphate salts. In other embodiments, the pH adjusting agent includes a dilute hydrochloric acid.

The medicament container 6400 can be any container suitable for storing the naloxone composition 6420. In some embodiments, the medicament container 6400 can be, for example, a pre-filled syringe, a pre-filled cartridge, a vial, an ampule or the like. In other embodiments, the medicament container 6400 can be a container having a flexible wall, such as, for example, a bladder. Although shown and described as being partially disposed within the housing 6110, in other embodiments, the medicament container 6400 can be disposed entirely within the housing 6110. Moreover, in some embodiments, the medicament container 6400 can be movably disposed within the housing 6110, such as, for example, in a manner similar to the medicament container 4400 shown and described above.

The delivery member 6450 is coupled to the medicament container 6400 and defines, at least in part, a flow path through which the naloxone composition 6420 can be delivered into a body. Although shown as being directly coupled to a distal end portion of the medicament container 6400, in other embodiments, the delivery member 6450 can be indirectly coupled to the medicament container 6400, (e.g., via the housing 6110).

Moreover, in some embodiments, the delivery member 6450 can be coupled to, but fluidically isolated from, the medicament container 6400 prior to actuation of the energy storage member 6570. In this manner, the medicament delivery device 6000 can be stored for extended periods of time while maintaining the sterility of the naloxone composition 6420 contained within the medicament container 6400, reducing (or eliminating) any leakage of the naloxone composition 6420 from the medicament container 6400 or the like. This arrangement also reduces and/or eliminates the assembly operations (e.g., the operation of coupling the delivery member 6450 to the medicament container 6400) before the medicament delivery device 6000 can be used to administer the naloxone composition 6200. In this manner, the medicament delivery device 6000 produces a quick and accurate mechanism for delivering the naloxone composition 6420. Similarly stated by reducing and/or eliminating the assembly operations prior to use, this arrangement reduces likelihood that performance of medicament delivery device 6000 and/or the delivery member 6450 will be compromised (e.g., by an improper coupling, a leak or the like).

In some embodiments, the delivery member 6450 can be coupled to the medicament container 6400 via a coupling member (not shown in FIG. 49) having similar functionality to the carrier 4520 shown and described above with respect to the medicament delivery device 4000. In such an embodiment, the medicament container 6400 and/or the delivery member 6450 can be configured to move relative to the coupling member when the energy storage member 6570 is actuated. Such movement can fluidically couple the delivery member 6450 and the medicament container 6400, thereby defining a flow path through which the naloxone composition 6420 can be delivered to the patient.

In some embodiments, the delivery member 6450 can enhance the delivery of the naloxone composition 6420 thereby improving the efficacy of the naloxone composition 6420. Similarly stated, in some embodiments, the delivery member 6450 can produce a flow of the naloxone composition 6420 having desired characteristics to enhance the absorption rate of the naloxone composition 6420, to minimize the delivery of the naloxone composition 6420 to regions of the body in which such delivery is less effective (e.g., the throat, etc.) or the like.

For example, in some embodiments, the delivery member 6450 can produce a controlled flow rate of the naloxone composition 6420. In such embodiments, the delivery member 6450 can include one or more flow orifices, a tortuous flow path or the like, to produce a desired pressure drop and/or to control the flow through the delivery member

6450. For example, in some embodiments, the delivery member 6450 can be configured to minimize excessive delivery of the naloxone composition 6420. For example, for intranasal applications, the delivery member 6450 can reduce the likelihood of excess deposition of the naloxone composition 6420 on the mucosal membrane, which can result in a portion of the naloxone composition 6420 being nonabsorbed (e.g., running out of the nose or into the throat).

In some embodiments, the delivery member 6450 can be configured to atomize the naloxone composition 6420 to produce a spray for intransal administration. For example, in some embodiments, the delivery member 6450 can produce an atomized spray of the naloxone composition having a desired spray geometry (e.g., spray angle and/or plume penetration) and/or droplet size distribution. In some embodiments, for example, the delivery member 6450 can include two chambers to allow substantially simultaneous deliver o the naloxone composition 6420 into both nostrils of a patient. Moreover, the delivery member 6450 can be cooperatively configured with the energy storage member 6570 to produce an atomized spray of the naloxone composition having a desired spray geometry and/or droplet size distribution. In this manner, the medicament delivery device 6000 can produce a consistent spray to enhance the efficacy of the naloxone composition 6420 under a wide variety of conditions.

In some embodiments, for example, the delivery member 6450 and the energy storage member 6570 can be cooperatively configured such that, when the energy storage member 6570 is actuated, the medicament delivery device 6000 produces an atomized spray of the naloxone composition 6420 having a substantial portion of the droplets therein having size distribution of between about 10 microns and about 20 microns. In this manner, the amount of the naloxone composition 6420 delivered to the lungs (e.g., the amount of smaller droplets that bypass the mucosal membrane) and/or the amount of the naloxone composition 6420 that runs into the throat (e.g., the amount of larger droplets) is minimized. In some embodiments, the delivery member 6450 and the energy storage member 6570 are cooperatively configured to produce a spray of the naloxone composition 6420 having a droplet size distribution wherein approximately 85 percent of the droplets have a size of between approximately 10 microns and 150 microns.

As described above, in some embodiments, the energy storage member 6570 is configured to "match" the delivery member 6450. Said another way, in some embodiments, the energy storage member 6570 is configured to produce the force F4 within a predetermined range to ensure the desired functionality of the delivery member 6450. Accordingly, the energy storage member 6570 can be any suitable device or mechanism that, when actuated, produces the desired force F4 to deliver the naloxone composition 6420 as described herein. By employing the energy storage member 6570 to produce the force F4, rather than relying on a user to manually produce the delivery force, the naloxone composition 6420 can be delivered into the body at the desired pressure and/or flow rate, and with the desired characteristics, as described above. Moreover, this arrangement reduces the likelihood of partial delivery (e.g., that may result if the user is interrupted or otherwise rendered unable to complete the delivery).

In some embodiments, the energy storage member 6570 can be a mechanical energy storage member, such as a spring, a device containing compressed gas, a device containing a vapor pressure-based propellant or the like. In other embodiments, the energy storage member 6570 can be an electrical energy storage member, such as a battery, a capacitor, a magnetic energy storage member or the like. In yet other embodiments, the energy storage member 6570 can be a chemical energy storage member, such as a container containing two substances that, when mixed, react to produce energy.

Figure 50:
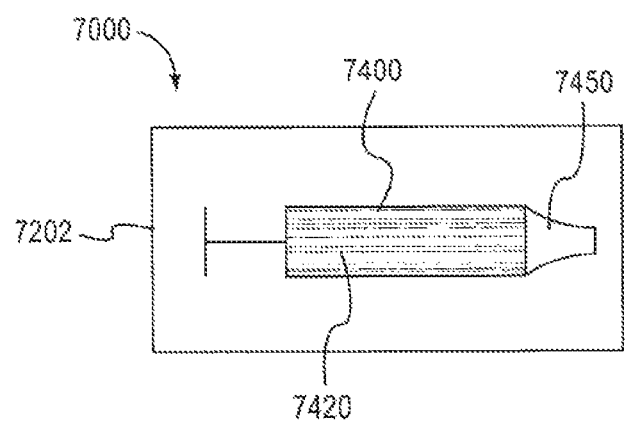
FIG. 50 is a schematic illustration of a kit including a medicament container according to an embodiment.

Although the medicament delivery device 6000 is shown and described above as including an energy storage member 6570, in other embodiments, a kit can include a medicament container containing a naloxone composition that is delivered by a manually-produced force. For example, FIG. 50 is a schematic illustration of a kit 7000 according to an embodiment. The kit 7000 includes a case 7202, a medicament container 7400 that contains (i.e., is filled or partially filled with) a naloxone composition 7420, and a delivery member 7450. The naloxone composition 7420 can be any of the naloxone compositions shown and described herein. The medicament container 7400 is movably disposed within the case 7202. More particularly, the medicament container 7400 can be removed from the case 7202 to deliver the naloxone composition 7420 contained therein.

Although the medicament container 7400 is shown as being substantially enclosed by and/or disposed within the case 7202, in other embodiments, the medicament container 7400 can be only partially enclosed by and/or disposed within the case 7202. In some embodiments, the case 7202 blocks an optical pathway between the medicament container 7400 and a region outside of the case 7202. Similarly stated, when the medicament container 7400 is disposed within the case 7202, the case 7202 is obstructs the medicament container 7400 to reduce the amount of light transmitted to the naloxone composition 7420 within the medicament container 7400.

The delivery member 7450, which can be a needle, an atomizer (e.g., for intranasal delivery, as described above), a mouthpiece or the like, is coupled to the medicament container 7400 and defines, at least in part, a flow path through which the naloxone composition 7420 can be delivered into a body. Although shown as being directly coupled to a distal end portion of the medicament container 7400, in other embodiments, the delivery member 7450 can be indirectly coupled to the medicament container 7400, (e.g., via a housing, not shown in FIG. 50).

Moreover, in some embodiments, the delivery member 7450 can be coupled to, but fluidically isolated from, the medicament container 7400 prior to actuation of the medicament container 7400 (e.g., by manually depressing a plunger, squeezing a trigger, or the like). In this manner, the medicament delivery device 7000 can be stored for extended periods of time while maintaining the sterility of the naloxone composition 7420 contained within the medicament container 7400, reducing (or eliminating) any leakage of the naloxone composition 7420 from the medicament container 7400 or the like. This arrangement also reduces and/or eliminates the assembly operations (e.g., the operation of coupling the delivery member 7450 to the medicament container 7400) before the medicament delivery device 7000 can be used to administer the naloxone composition 7200. In this manner, the medicament delivery device 7000 produces a quick and accurate mechanism for delivering the naloxone composition 7420. Similarly stated by reducing and/or eliminating the assembly operations prior to use, this arrangement reduces likelihood that performance of medicament delivery device 7000 and/or the delivery member 7450 will be compromised (e.g., by an improper coupling, a leak or the like).

In some embodiments, the delivery member 7450 can be coupled to the medicament container 7400 via a coupling member (not shown in FIG. 50) having similar functionality to the carrier 4520 shown and described above with respect to the medicament delivery device 4000. In such an embodiment, the medicament container 7400 and/or the delivery member 7450 can be configured to move relative to the coupling member when the medicament container 7400 is actuated. For example, in use, upon depressing a plunger to actuate the medicament container 7400, the coupling member can move relative to the medicament container 7400 before a substantial portion of the energy produced by movement of the plunger is exerted on the naloxone composition 7420. Such movement can fluidically couple the delivery member 7450 and the medicament container 7400, thereby defining a flow path through which the naloxone composition 7420 can be delivered to the patient.

In some embodiments, at least one of the medicament container 7400 and the case 7202 can include an electronic circuit system (not shown in FIG. 50) similar to the electronic circuit systems shown and described herein. In such embodiments, the electronic circuit system can be actuated when the medicament container is removed from the case 7202. Any suitable mechanism can be used to actuate the electronic circuit system when the medicament container 7400 is removed from the case 7202. Such mechanisms include those mechanisms disclosed in U.S. Patent Publication No. 2007/0129708, entitled "Devices, Systems and Methods for Medicament Delivery," filed on Feb. 5, 2007, which is incorporated herein by reference in its entirety.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although the medical injector 4000 includes the electronic circuit system cavity 4153, the gas cavity 4154 and/or the medicament cavity 4157 that are shown and described as being fluidically and/or physically isolated from each other, in other embodiments, any of the electronic circuit system cavity 4153, the gas cavity 4154 and/or the medicament cavity 4157 can be fluidically coupled to and/or share a common boundary with each other. In some embodiments, for example, a housing can define a single cavity within which a medicament container, an energy storage member and an electronic circuit system are disposed.

Although the medical injector 4000 discloses a gas-powered delivery device, in other embodiments, any of the medicament delivery devices disclosed herein can include any suitable energy storage member. Such energy storage members can be, for example, a mechanical energy storage member, such as a spring, a device containing compressed gas, a device containing a vapor pressure-based propellant or the like. In other embodiments, the energy storage member can be an electrical energy storage member, such as a battery, a capacitor, a magnetic energy storage member or the like. In yet other embodiments, the energy storage member can be a chemical energy storage member, such as a container containing two substances that, when mixed, react to produce energy.

The medicament containers and/or medicament delivery devices disclosed herein can contain any suitable amount of any of the naloxone compositions disclosed herein. For example, in some embodiments, a medicament delivery device as shown herein can be a single-dose device containing an amount of the naloxone composition to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like). In some embodiments, an electronic circuit system can include "configuration switch" (similar to the configuration switch 5974 shown and described above) that, when actuated during the assembly of the delivery device, can select an electronic output corresponding to the dose contained within the medicament container.

Although the electronic circuit system 4900 is shown and described above as having two irreversible switches (e.g., switch 4972 and switch 4973), in other embodiments, an electronic circuit system can have any number of switches. Such switches can be either reversible or irreversible.

Although the electronic circuit system 4900 is shown and described above as producing an electronic output in response to the actuation of two switches (e.g., switch 4972 and switch 4973), in other embodiments, an electronic circuit system can produce an electronic output in response to any suitable input, command or prompt. Suitable input for prompting an output can include, for example, an audible input by the user (e.g., the user's response to a voice prompt produced by the electronic circuit system), an input from a "start button" depressed by the user, an input from a sensor (e.g., a proximity sensor, a temperature sensor or the like), movement of (e.g., shaking) of the medicament delivery device, or the like. In some embodiments, an electronic circuit system can include a microphone and/or a voice recognition module to detect a user's vocal input.

Although medical devices having two LEDs and an audio output device have been shown, in other embodiments the medical device might have any number of LEDs and/or audio output devices. Additionally, other types of output devices, such as haptic output devices, can be used. In some embodiments, outputs from an electronic circuit system can include, for example, an audible or visual output related to the naloxone composition (e.g., an indication of the expiration date, the symptoms requirement treatment with naloxone or the like), the use of the medicament delivery device, and/or post-administration procedures (e.g., a prompt to call 911, instructions for the disposal of the device or the like).

Although various embodiments have been described as having particular features and/or combinations of components, other embodiments are possible having a combination of any features and/or components from any of embodiments where appropriate. For example, any of the devices shown and described herein can include an electronic circuit system as described herein. For example, although the medicament delivery device 6000 shown in FIG. 49 is not shown as including an electronic circuit system, in other embodiments, a medicament delivery device similar to the device 6000 can include an electronic circuit system similar to the electronic circuit system 4900 shown and described above.

Any of the medicament containers described herein can include any of the elastomeric members described herein. For example, the medicament container 7400 can include an elastomeric member that is formulated to be compatible with the naloxone composition contained therein, similar to the elastomeric member 2410 shown and described above.

Any of the medicament containers described herein can contain any of the naloxone compositions and/or formulations described herein.

What is claimed is:

1. A method, comprising:
removing a medicament delivery device containing a naloxone composition from a case, the medicament delivery device including a housing, a medicament container, and a delivery member, the medicament container disposed within the housing and defining an internal volume containing the naloxone composition, the naloxone composition including a tonicity-adjusting agent, the pH of the naloxone composition ranging from 3 to 5, the delivery member coupled to the medicament container before the removing;
receiving an instruction associated with a use of the medicament delivery device; and
actuating the medicament delivery device to (1) cause the medicament container to move distally within the housing to place the delivery member in fluid communication with the internal volume of the medicament container and (2) convey a single dose of the naloxone composition from the internal volume via the delivery member.

2. The method of claim 1, wherein:
the medicament delivery device is an auto-injector; and
the delivery member is a needle, the needle being coupled to the medicament container via a coupling member, the needle being fluidically isolated from the internal volume when the coupling member and the medicament container are in a first configuration, the needle in fluid communication with the internal volume when the coupling member and the medicament container are in a second configuration.

3. The method of claim 1, wherein:
the medicament delivery device is an intranasal spray device; and
the delivery member is associated with an atomizer defining an orifice through which the naloxone composition is delivered, the atomizer being coupled to the medicament container via a coupling member, the coupling member including a needle, the coupling member and the medicament container being in a first configuration prior to the medicament delivery device being removed from the case, an end portion of the needle being disposed outside of the internal volume when the coupling member and the medicament container are in the first configuration, the end portion of the needle disposed within the internal volume when the coupling member and the medicament container are in a second configuration.

4. The method of claim 1; further comprising:
storing, before the removing, the medicament delivery device within the case for at least six months.

5. The method of claim 1, further comprising:
sending a wireless signal in response to the removing the medicament delivery device from the case.

6. The method of claim 1, wherein the instruction is a written instruction coupled to at least one of the case or the medicament delivery device.

7. The method of claim 1, wherein the instruction is a recorded speech output produced by at least one of the case or the medicament delivery device.

8. The method of claim 1, wherein:
the medicament delivery device is stored within the case for at least six months before the removing; and
the actuating the medicament delivery device causes movement of an elastomeric member within the medicament container to convey the single dose of the naloxone composition from the internal volume, the elastomeric member including a silicone-based material.

9. The method of claim 1, wherein:
the tonicity-adjusting agent includes sodium chloride in an amount such that a concentration of sodium chloride is between 0.1 mg/mL and 20 ng/mL.

10. The method of claim 1, wherein the medicament delivery device is a medical injector and the delivery member is a needle covered by a needle sheath, the method further comprising:
removing, before the actuating, a safety lock coupled to a distal end portion of the housing, the safety lock including an engagement portion that engages the needle sheath and removes the needle sheath from about the needle in response to the removing the safety lock.

11. The method of claim 1, wherein:
the actuating the medicament delivery device includes placing, by a first person, a distal end portion of the housing against a target location of a second person,
the instructions received by the first person,
the single dose of the naloxone composition conveyed to the target location of the second person.

12. The method of claim 1, wherein the naloxone composition includes 4,5-epoxy-3,14-di hydroxy-17-(2-propenyl)morphinan-6-one in a concentration of between about 0.01 mg/mL and about 60 mg/mL.

13. The method of claim 12, wherein the concentration of the 4,5-epoxy-3,14-dihydroxy-17-(2-propenyl)morphinan-6-one is about 10 mg/mL.

14. The method of claim 12, wherein the single dose of the naloxone composition conveyed from the internal volume contains between 3 mg and 24 mg of the naloxone composition.

15. The method of claim 14, wherein the single dose of the naloxone composition conveyed from the internal volume contains between 4 mg and 18 mg of the naloxone composition.

16. A method of delivering a single dose of a naloxone composition to a patient, comprising:
removing a medical injector containing the naloxone composition from a case, the medical injector including a housing, a prefilled medicament container assembly, and a needle, the prefilled medicament container assembly disposed within the housing and including a container body, the naloxone composition contained within the container body, and an elastomeric member that seals the naloxone composition within the container body, the naloxone composition including a tonicity-adjusting agent and a pH adjusting agent, the pH of the naloxone composition ranging from 3 to 5, the needle coupled to the prefilled medicament container assembly before the removing;
receiving an instruction associated with a use of the medical injector;
placing a portion of the medical injector into contact with the patient; and
actuating the medical injector to cause the elastomeric member to move within the container body to convey the single dose of the naloxone composition from the container body via the needle.

17. The method of claim 16, wherein the actuating includes moving an actuator coupled to an end portion of the housing to cause a force to be applied to a rod that moves the elastomeric member within the container body.

18. The method of claim 16, wherein the prefilled medicament container assembly is a prefilled syringe.

19. The method of claim 16, wherein:
the medical injector is stored within the case for at least six months before the removing; and
the elastomeric member includes a silicone-based material.

20. The method of claim 16, wherein the elastomeric member is formulated to be compatible with the naloxone composition when in contact with the naloxone composition for a time period of at least two years.

21. The method of claim 20, wherein the elastomeric member is formulated to include a polymer and a curing agent, the polymer including at least one of bromobutyl or chlorobutyl, the curing agent including at least one of sulfur or a metal oxide.

22. The method of claim 16, wherein:
the pH of the naloxone composition ranges from about 3.2-3.6;
the tonicity-adjusting agent includes at least one of dextrose, glycerin, mannitol, potassium chloride or sodium chloride; and
the elastomeric member includes a polymer and a curing agent, the elastomeric member is formulated to be compatible with the naloxone composition when in contact with the naloxone composition for a time period of at least two years.

23. The method of claim 16, wherein the naloxone composition includes 4,5-epoxy-3,14-dihydroxy-17-(2-propenyl)morphinan-6-one in a concentration of between about 0.01 mg/mL and about 60 mg/mL.

24. The method of claim 23, wherein the concentration of the 4,5-epoxy-3,14-dihydroxy-17-(2-propenyl)morphinan-6-one is about 10 mg/mL.

25. The method of claim 23, wherein the single dose of the naloxone composition conveyed from the internal volume contains between 3 mg and 24 rig of the naloxone composition.

26. The method of claim 25, wherein the single dose of the naloxone composition conveyed from the internal volume contains between mg and 18 mg of the naloxone composition.

* * * * *

UNITED STATES PATENT AND TRADEMARK OFFICE
CERTIFICATE OF CORRECTION

Page 1 of 1

PATENT NO. : 10,143,792 B2
APPLICATION NO. : 15/331073
DATED : December 4, 2018
INVENTOR(S) : Eric S. Edwards et al.

It is certified that error appears in the above-identified patent and that said Letters Patent is hereby corrected as shown below:

In the Specification

Column 4, Line 23: the phrase "FIG. 36 is a front view of the medical injector" should be -- FIG. 36 is a front view of the base of the medical injector --

In the Claims

Column 49, Line 50 (Claim 4): the phrase "The method of claim 1;" should be -- The method of claim 1, --

Column 50, Line 7 (Claim 9): the phrase "and 20ng/mL." should be -- and 20mg/mL. --

Column 52, Line 15 (Claim 25): the phrase "contains between 3 mg and 24 rig" should be -- contains between 3 mg and 24 mg --

Column 52, Line 19 (Claim 26): the phrase "contains between mg and 18 mg" should be -- contains between 4 mg and 18 mg --

Signed and Sealed this
Seventh Day of May, 2019

Andrei Iancu
*Director of the United States Patent and Trademark Office*